(12) United States Patent
Merio et al.

(10) Patent No.: US 8,008,466 B2
(45) Date of Patent: Aug. 30, 2011

(54) USE OF UNTRANSLATED REGION OF OSMOTIN GENE TO ENHANCE TRANSGENE EXPRESSION IN PLANTS

(75) Inventors: Donald Joseph Merio, Carmel, IN (US); Dong Liu, Carmel, IN (US); Stephanie Love Burton, Indianapolis, IN (US); Todd Philip Glancy, Fairmount, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 568 days.

(21) Appl. No.: 11/448,061

(22) Filed: Jun. 6, 2006

(65) Prior Publication Data

US 2007/0089202 A1    Apr. 19, 2007

Related U.S. Application Data

(62) Division of application No. 10/703,280, filed on Nov. 7, 2003, now abandoned.

(60) Provisional application No. 60/416,142, filed on Oct. 4, 2002.

(51) Int. Cl.
    *C07H 21/04*    (2006.01)
    *C12N 15/00*    (2006.01)
    *C12N 15/113*   (2006.01)
    *C12N 15/63*    (2006.01)

(52) U.S. Cl. ...... 536/24.1; 536/23.1; 800/278; 800/279; 435/320.1

(58) Field of Classification Search .................. None
    See application file for complete search history.

(56) References Cited

U.S. PATENT DOCUMENTS 5,874,626 A * 2/1999 Bressan et al. ............. 800/279
6,590,142 B1 * 7/2003 Petell et al. ................ 800/302

OTHER PUBLICATIONS

Rombauts et al 2003 Plant Physiology 132:1162-1176.*

Liu et al 2003 Nature Biotechnology 21:1222-1228, provided by Applicant.*
USPTO Office Communication dated Mar. 1, 2005 regarding U.S. Appl. No. 10/703,280 filed Nov. 7, 2003 (including Office communication and Notice of References cited).
USPTO Notice of Allowability dated Mar. 19, 2006 regarding U.S. Appl. No. 10/703,280 filed Nov. 7, 2003 (including Notice of Allowability, Examiner's Amendment and Notice of References cited).
Dong Liu, Insect resistance conferred by 283-kDa Photorhabdus Luminescens protein TcdA in *Arabidopsis thaliana*, Nature Biotechnology, Oct. 2003, pp. 1222-1228,vol. 21, No. 10, Dow AgroSciences LLC, vol. 21, No. 10, Indianapolis, Indiana.
Donald E. Nelson, Analysis of structure and transcriptional activation of an osmotin gene, Plant Molecular Biology 1992, pp. 577-588, vol. 19, 1992 Kluwer Academic Publisher, printed in Belgium.
Andrzej K. Kononowicz, Regulation of the Osmotin Gene Promoter, the Plant Cell, 1992, vol. 4, 513-524. The American Society of Plant Physiologists.
John C. Ingersoll, Effect of promoter-leader sequences on transient expression of reporter gene chimeras biolistically transferred into sugarbeet (Beta vulgaris) suspension cells, Plant Cell Reports, Spring 1996, pp. 836-840, Plant Molecular Biology Laboratory, United State Department of Agriculture, Beltsville, Maryland.
Japanese Patent Office Communication, dated Jan. 12, 2010, regarding JP 2004-023901.
Australian Patent Office Communication, dated Jun. 29, 2009, regarding AU 2004200330.

* cited by examiner

*Primary Examiner* — Brent Page
(74) *Attorney, Agent, or Firm* — James Daly, IV; Kenneth B. Ludwig; Marcia I. Rosenfeld

(57) ABSTRACT

The present invention provides methods, vectors and gene constructs for enhancing expression of a recombinant nucleic acid sequence in transgenic plants and plant tissues. According to the present invention, nucleic acid sequences are obtained and/or derived from the 5' and 3' untranslated regions of genes encoding osmotin proteins and engineered to flank respective portions of a selected coding region of a vector. The vector construct may be introduced into plants and/or plant tissues through conventional procedures, resulting in enhanced expression of the selected coding region. In a preferred embodiment, the selected coding region is a chimeric gene or gene fragment expressing one or more proteins known to impart a level of insecticidal activity to a transgenic plant and/or plant tissue.

8 Claims, 38 Drawing Sheets

A.
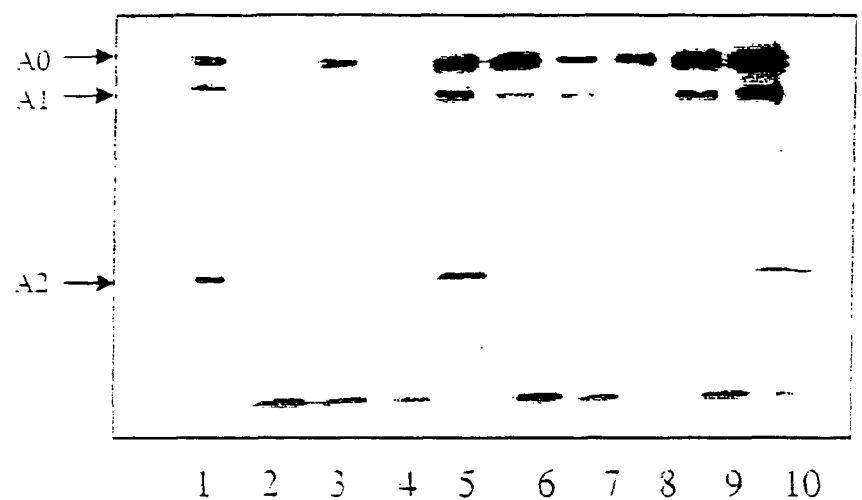
B.
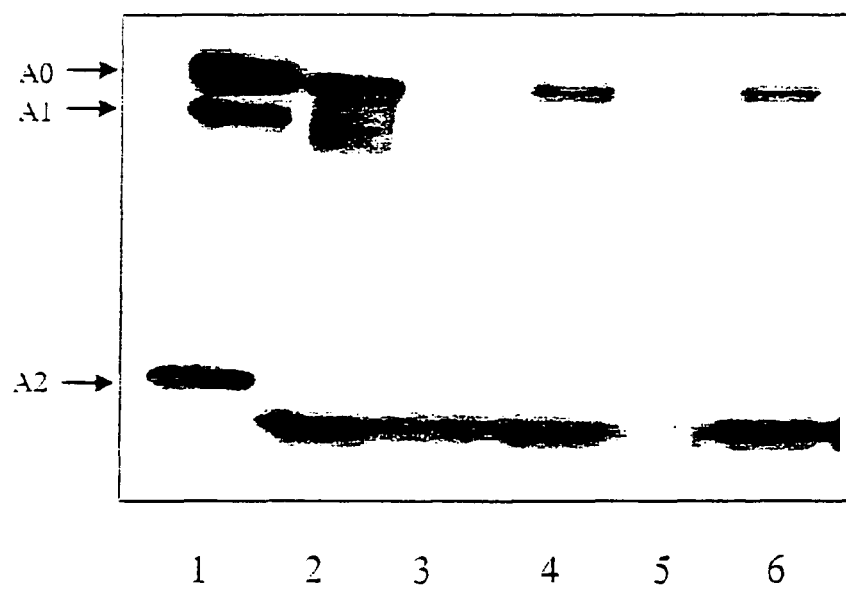
Figure 4

A. 5'-TCCAACAACCCAACTTGTTAAAAAATGTCCAACAAC-3'

A/T content: 25/38=67%

```
   1 ccatggctaa cgagtccgtc aaggagatcc cagacgtcct caagtcccaa tgcggtttca
  61 actgcctcac tgacatctcc cacagctcct tcaacgagtt cagacaacaa gtctctgagc
 121 acctctcctg gtccgagacc catgacctct accatgacgc tcagcaagct cagaaggaca
 181 acaggctcta cgaggctagg atcctcaaga gggctaaccc acaactccag aacgctgtcc
 241 acctcgccat cttggctcca aacgctgagt tgattggtta caacaaccag ttctctggca
 301 gagctagcca gtacgtggct cctggtacag tctcctccat gttcagccca gccgcttacc
 361 tcactgagtt gtaccgcgag gctaggaacc ttcatgcttc tgactccgtc tactacttgg
 421 acacacgcag accagacctc aagagcatgg ccctcagcca acagaacatg gacattgagt
 481 tgtccaccct ctccttgagc aacgagcttc tcttggagtc catcaagact gagagcaagt
 541 tggagaacta caccaaggtc atggagatgc tctccacctt cagaccaagc ggtgcaactc
 601 cataccatga tgcctacgag aacgtcaggg aggtcatcca acttaagac cctggtcttg
 661 agcaactcaa cgcttctcca gccattgctg gtttgatgca ccaggcatcc ttgctcggta
 721 tcaacgcctc catctctcct gagttgttca acatcttgac tgaggagatc actgagggca
 781 acgctgagga gttgtacaag aagaacttcg caacattga ccagcctct cttgcaatgc
 841 ctgagtacct caagaggtac tacaacttgt ctgatgagga gctttctcaa ttcattggca
 901 aggcttccaa cttcggtcaa caggagtaca gcaacaacca gctcatcact ccagttgtga
 961 actcctctga tggcactgtg aaggtctacc gcatcacacg tgagtacacc acaaacgcct
1021 accaaatgga tgttgagttg ttcccattcg gtggtgagaa ctacagactt gactacaagt
1081 tcaagaactt ctacaacgcc tcctacctct ccatcaagtt gaacgacaag agggagcttg
1141 tcaggactga gggtgctcct caagtgaaca ttgagtactc tgccaacatc accctcaaca
1201 cagctgacat ctctcaacca ttcgagattg gtttgaccag agtccttccc tctggctcct
1261 gggcctacgc tgcagccaag ttcactgttg aggagtacaa ccagtactct ttcctcttga
1321 agctcaacaa ggcaattcgt ctcagcagag ccactgagtt gtctcccacc atcttggagg
1381 gcattgtgag gtctgtcaac cttcaacttg acatcaacac tgatgtgctt ggcaaggtct
1441 tcctcaccaa gtactacatg caacgctacg ccatccatgc tgagactgca ctcatcctct
1501 gcaacgcacc catctctcaa cgctcctacg acaaccagcc ttcccagttc gacaggctct
1561 tcaacactcc tctcttgaac ggccagtact tctccactgg tgatgaggag attgacctca
1621 actctggctc cacaggtgac tggagaaaga ccattcgtga gagggccttc aacattgatg
1681 atgtctctct cttccgtctc ttgaagatca cagatcgaca caacaaggat ggcaagatca
1741 agaacaactt gaagaacctt tccaacctct acattggcaa gttgcttgca gacatccacc
1801 aactcaccat tgatgagttg gacctcttgc tcattgcagt cggtgagggc aagaccaacc
1861 tctctgcaat ctctgacaag cagttggcaa ccctcatcag gaagttgaac accatcacct
1921 cctggcttca cacccagaag tggtctgtct tccaactctt catcatgacc agcacctcct
1981 acaacaagac cctcactcct gagatcaaga acctcttgga cacagtctac cacggtctcc
2041 aaggcttcga caaggacaag gctgacttgc ttcatgtcat ggctccctac attgcagcca
2101 ccctccaact ctcctctgag aacgtggctc actctgtctt gctctgggct gacaagctcc
2161 aacctggtga tggtgccatg actgctgaga agttctggga ctggctcaac accaagtaca
2221 caccaggctc ctctgaggct gttgagactc aagagcacat tgtgcaatac tgccaggctc
2281 ttgcacagtt ggagatggtc taccactcca ctggcatcaa cgagaacgct ttcagactct
2341 tcgtcaccaa gcctgagatg ttcggtgctg ccacaggtgc tgcacctgct catgatgctc
2401 tctccctcat catgttgacc aggttcgctg actgggtcaa cgctcttggt gagaaggctt
2461 cctctgtctt ggctgccttc gaggccaact ccctcactgc tgagcaactt gctgatgcca
2521 tgaaccttga tgccaacctc ttgctccaag cttccattca agctcagaac accaacaccc
2581 tcccacctgt cactccagag aacgctttct cctgctggac ctccatcaac accatcctcc
2641 aatgggtcaa cgtggctcag caactcaacg tggctccaca aggtgtctct gctttggtcg
2701 gtcttgacta catccagtcc atgaaggaga caccaaccta cgctcaatgg gagaacgcag
2761 ctggtgtctt gactgctggt ctcaactcca aacaggccaa caccctccat gcttttcttgg
2821 atgagtctcg ctctgctgcc ctctccacct actacatcag gcaagtcgcc aaggcagctg
2881 ctgccatcaa gtctcgcgat gacctctacc aataccctcct cattgacaac caggtctctg
2941 ctgccatcaa gaccaccagg atcgctgagg ccatcgcttc catccaactc tacgtcaacc
3001 gcgctcttga aacgttgag gagaacgcca actctggtgt catctctcgc caattcttca
3061 tcgactggga caagtacaac aagaggtact ccacctgggc tggtgtctct caacttgtct
3121 actaccagaa gaactacatt gacccaacca tgaggattgg tcagaccaag atgatggatg
3181 ctctcttgca atctgtctcc caaagccaac tcaacgctga cactgtggag gatgccttca
3241 tgagctacct cacctccttc gagcaagttc caacctcaa ggtcatctct gcttaccatg
3301 acaacatcaa caacgaccaa ggtctcacct acttcattgg tctctctgag actgatgctg
3361 gtgagtacta ctggagcatc gtggaccaca gcaagttcaa cgatggcaag ttcgctgcaa
3421 acgcttggtc tgagtggcac aagattgact gcccatacaa cccatacaag tccaccatca
3481 gacctgtcat ctacaagagc cgcctctact gctctggct tgagcagaag gagatcacca
3541 agcaaactgg caactccaag gatggttacc aaactgagac tgactaccgc tacgagttga
3601 agttggctca catccgctac gatggtacct ggaacactcc aatcaccttc gatgtcaaca
3661 agaagatcag cgagttgaag ttggagaaga ccgtgctcc tggtctctac tgcgctggtt
3721 accaaggtga ggacaccctc ttggtcatgt ctacaaccgg gcaagacacc cttgactcct
```

Figure 21 (cont.)

```
3781 acaagaacgc ttccatgcaa ggtctctaca tcttcgctga catggcttcc aaggacatga
3841 ctccagagca aagcaacgtc taccgtgaca actcctacca acagttcgac accaacaacg
3901 tcaggcgtgt caacaacaga tacgctgagg actacgagat cccaagctct gtcagctctc
3961 gcaaggacta cggctggggt gactactacc tcagcatggt gtacaacggt gacatcccaa
4021 ccatcaacta caaggctgcc tcttccgacc tcaaaatcta catcagccca aagctcagga
4081 tcatccacaa cggctacgag ggtcagaaga ggaaccagtg caacttgatg aacaagtacg
4141 gcaagttggg tgacaagttc attgtctaca cctctcttgg tgtcaaccca acaacagct
4201 ccaacaagct catgttctac ccagtctacc aatactctgg caacacctct ggtctcaacc
4261 agggtagact cttgttccac agggacacca cctacccaag caaggtggag gcttggattc
4321 ctggtgccaa gaggtccctc accaaccaga acgctgccat ggtgatgac tacgccacag
4381 actccctcaa caagcctgat gacctcaagc agtacatctt catgactgac tccaagggca
4441 cagccactga tgtctctggt ccagtggaga tcaacactga aatcagccca gccaaggtcc
4501 aaatcattgt caaggctggt ggcaaggagc aaaccttcac agctgacaag gatgtctcca
4561 tccagccaag cccatccttc gatgagatga actaccaatt caacgctctt gagattgatg
4621 gttctggcct caacttcatc aacaactctg cttccattga tgtcaccttc actgccttcg
4681 ctgaggatgg ccgcaagttg ggttacgaga gcttctccat cccagtcacc cttaaggttt
4741 ccactgacaa cgcactcacc cttcatcaca acgagaacgg tgctcagtac atgcaatggc
4801 aaagctaccg caccaggttg aacaccctct tcgcaaggca acttgtggcc cgtgccacca
4861 caggcattga caccatcctc agcatggaga cccagaacat ccaagagcca cagttgggca
4921 agggtttcta cgccaccttc gtcatcccac cttacaacct cagcactcat ggtgatgaga
4981 ggtggttcaa gctctacatc aagcacgtgg ttgacaacaa ctcccacatc atctactctg
5041 gtcaactcac tgacaccaac atcaacatca ccctcttcat cccacttgac gatgtcccac
5101 tcaaccagga ctaccatgcc aaggtctaca tgaccttcaa gaagtctcca tctgatggca
5161 cctggtgggg tccacacttc gtccgtgatg acaagggcat cgtcaccatc aacccaaagt
5221 ccatcctcac ccacttcgag tctgtcaacg ttctcaacaa catctcctct gagccaatgg
5281 acttctctgg tgccaactcc ctctacttct gggagttgtt ctactacaca ccaatgcttg
5341 tggctcaaag gttgctccat gagcagaact tcgatgaggc caacaggtgg ctcaagtacg
5401 tctggagccc atctggttac attgtgcatg gtcaaatcca gaactaccaa tggaacgtca
5461 ggccattgct tgaggacacc tcctggaact ctgacccact tgactctgtg gaccctgatg
5521 ctgtggctca acatgaccca atgcactaca aggtctccac cttcatgagg accttggacc
5581 tcttgattgc cagaggtgac catgcttacc gccaattgga gagggacacc ctcaacgagg
5641 caaagatgtg gtacatgcaa gctctccacc tcttgggtga caagccatac ctcccactca
5701 gcaccacttg gtccgaccca aggttggacc gtgctgctga catcaccact cagaacgctc
5761 atgactctgc cattgttgct ctcaggcaga acatcccaac tcctgctcca ctctccctca
5821 gatctgctaa caccctcact gacttgttcc tccacagat caacgaggtc atgatgaact
5881 actggcaaac cttggctcaa agggtctaca acctcagaca caacctctcc attgatggtc
5941 aaccactcta cctcccaatc tacgccacac cagctgaccc aaaggctctt ctctctgctg
6001 ctgtggctac cagccaaggt ggtggcaagc tcccagagtc cttcatgtcc ctctggaggt
6061 tcccacacat gttggagaac gcccgtggca tggtctccca actcacccag ttcggttcca
6121 ccctccagaa catcattgag aggcaagatg ctgaggctct caacgctttg ctccagaacc
6181 aggcagctga gttgatcctc accaacttgt ccatccaaga caagaccatt gaggagcttg
6241 atgctgagaa gacagtcctt gagaagagca aggctggtgc ccaatctcgc ttcgactcct
6301 acggcaagct ctacgatgag aacatcaacg ctggtgagaa ccaggccatg accctcaggg
6361 cttccgcagc tggtctcacc actgctgtcc aagcctctcg cttggctggt gcagctgctg
6421 acctcgttcc aaacatcttc ggtttcgctg gtggtggctc cagatggggt gccattgctg
6481 aggctaccgg ttacgtcatg gagttctctg ccaacgtcat gaacactgag gctgacaaga
6541 tcagccaatc tgagacctac agaaggcgcc gtcaagagtg ggagatccaa aggaacaacg
6601 ctgaggcaga gttgaagcaa atcgatgctc aactcaagtc cttggctgtc agaagggagg
6661 ctgctgtcct ccagaagacc tccctcaaga cccaacagga gcaaacccag tcccagttgg
6721 ctttcctcca aaggaagttc tccaaccagg ctctctacaa ctggctcaga ggccgcttgg
6781 ctgccatcta cttccaattc tacgaccttg ctgtggccag gtgcctcatg gctgagcaag
6841 cctaccgctg ggagttgaac gatgactccg ccaggttcat caagccaggt gcttggcaag
6901 gcacctacgc tggtctcctt gctggtgaga ccctcatgct ctccttggct caaatggagg
6961 atgctcacct caagagggac aagagggctt tggaggtgga gaggacagtc tcccttgctg
7021 aggtctacgc tggtctccca aaggacaacg tccattctc ccttgctcaa gagattgaca
7081 agttggtcag ccaaggttct ggttctgctg gttctggtaa caacaacttg gctttcggcg
7141 ctggtactga caccaagacc tccctccaag cctctgtctc cttcgctgac ctcaagatca
7201 gggaggacta cccagcttcc cttggcaaga tcaggcgcat caagcaaatc tctgtcaccc
7261 tccagctctc cttgggtcca taccaagatg tccaagcaat cctctcctac ggtgacaagg
7321 ctggtttggc gaacggttgc gaggctcttg ctgtctctca tggcatgaac gactctggtc
7381 aattccaact tgacttcaac gatggcaagt tcctcccatt cgagggcatt gccattgacc
7441 aaggcaccct cacccctctc ttcccaaacg cttccatgcc agagaaggga aagcaagcca
7501 ccatgctcaa gaccctcaac gatatcatcc tccacatcag gtacaccatc aagtgagctc
```

Figure 22

```
   1 ccatggctga gttgattggt tacaacaacc agttctctgg cagagctagc cagtacgtgg
  61 ctcctggtac agtctcctcc atgttcagcc cagccgctta cctcactgag ttgtaccgcg
 121 aggctaggaa ccttcatgct tctgactccg tctactactt ggacacacgc agaccagacc
 181 tcaagagcat ggccctcagc aacagaaca tggacattga gttgtccacc ctctccttga
 241 gcaacgagct tctcttggag tccatcaaga ctgagagcaa gttggagaac tacaccaagg
 301 tcatggagat gctctccacc ttcagaccaa gcggtgcaac tccataccat gatgcctacg
 361 agaacgtcag ggaggtcatc aacttcaag accctggtct tgagcaactc aacgcttctc
 421 cagccattgc tggtttgatg caccaggcat ccttgctcgg tatcaacgcc tccatctctc
 481 ctgagttgtt caacatcttg actgaggaga tcactgaggg caacgctgag gagttgtaca
 541 agaagaactt cggcaacatt gagccagcct ctcttgcaat gcctgagtac ctcaagaggt
 601 actacaactt gtctgatgag gagctttctc aattcattgg caaggcttcc aacttcggtc
 661 aacaggagta cagcaacaac cagctcatca ctccagttgt gaactcctct gatggcactg
 721 tgaaggtcta ccgcatcaca cgtgagtaca ccacaaacgc ctaccaaatg gatgttgagt
 781 tgttcccatt cggtggtgag aactacagac ttgactacaa gttcaagaac ttctacaacg
 841 cctcctacct ctccatcaag ttgaacgaca gagggagct tgtcaggact gagggtgctc
 901 ctcaagtgaa cattgagtac tctgccaaca tcaccctcaa cacagctgac atctctcaac
 961 cattcgagat tggtttgacc agagtccttc cctctggctc tgggcctac gctgcagcca
1021 agttcactgt tgaggagtac aaccagtact cttccctctt gaagctcaac aaggcaattc
1081 gtctcagcag agccactgag ttgtctccca ccatcttgga gggcattgtg aggtctgtca
1141 accttcaact tgacatcaac actgatgtgc ttggcaaggt cttcctcacc aagtactaca
1201 tgcaacgcta cgccatccat gctgagactg cactcatcct ctgcagcgca cccatctctc
1261 aacgctccta cgacaaccag ccttcccagt tcgacaggct cttcaaccct cctctcttga
1321 acggccagta cttctccact ggtgatgagg agattgacct caactctggc tccacaggtg
1381 actggagaaa gaccatcttg aagagggcct tcaacattga tgatgtctct ctcttccgtc
1441 tcttgaagat cacagatcac gacaacaagg atggcaagat caagaacaac ttgaagaacc
1501 tttccaacct ctacattggc aagttgcttg cagacatcca ccaactcacc attgatgagt
1561 tggacctctt gctcattgca gtcggtgagg caagaccaa cctctctgca atctctgaca
1621 agcagttggc aaccctcatc aggaagttga acaccatcac ctcctggctt cacacccaga
1681 agtggtctgt cttccaactc ttcatcatga ccagcacctc ctacaacaag accctcactc
1741 ctgagatcaa gaacctcttg gacacagtct accacggtct ccaaggcttc gacaaggaca
1801 aggctgactt gcttcatgtc atggctccct acattgcagc caccctccaa ctctcctctg
1861 agaacgtgcc tcactctgtc ttgctctggg ctgacaagct caacctggt gatggtgcca
1921 tgactgctga gaagttctgg gactggctca acaccaagta cacaccaggc tcctctgagg
1981 ctgttgagac tcaagagcac attgtgcaat actgccaggc tcttgcacag ttggagatgg
2041 tctaccactc cactggcatc aacgagaacg ctttcagact cttcgtcacc aagcctgaga
2101 tgttcggtgc tgccacaggt gctgcacctg ctcatgatgc tctctccctc atcatgttga
2161 ccaggttcgc tgactgggtc aacgctcttg gtgagaaggc ttcctctgtc ttggctgcct
2221 tcgaggccaa ctccctcact gctgagcaac ttgctgatgc catgaacctt gatgccaacc
2281 tcttgctcca agcttccatt caagctcaga accaccaaca cctcccacct gtcactccag
2341 agaacgcttt ctcctgctgg acctccatca acaccatcct ccaatgggtc aacgtggctc
2401 agcaactcaa cgtggctcca caaggtgtct ctgctttggt cggtcttgac tacatccagt
2461 ccatgaagga gacaccaacc tacgctcaat gggagaacgc agctggtgtc ttgactgctg
2521 gtctcaactc ccaacaggcc aacaccctcc atgctttctt ggatgagtct cgctctgctg
2581 ccctctccac ctactacatc aggcaagtcg ccaaggcagc tgctgccatc aagtctcgcg
2641 atgacctcta ccaataccte ctcattgaca ccaggtctc tgctgccatc aagaccacca
2701 ggatcgctga ggccatcgct tccatccaac tctacgtcaa ccgcgctctt gagaacgttg
2761 aggagaacgc caactctggt gtcatctctc gccaattctt catcgactgg acaagtaca
2821 acaagaggta ctccacctgg gctggtgtct ctcaacttgt ctactaccca gagaactaca
2881 ttgacccaac catgaggatt ggtcagacca agatgatgga tgctctcttg caatctgtct
2941 cccaaagcca actcaacgct gacactgtgg aggatgcctt catgagctac ctcacctcct
3001 tcgagcaagt tgccaacctc aaggtcatct ctgcttacca tgacaacatc aacaacgacc
3061 aaggtctcac ctacttcatt ggtctctctg agactgatgc tggtgagtac tactggagat
3121 ccgtggacca cagcaagttc aacgatgca agttcgctgc aaacgcttgg tctgagtggc
3181 acaagattga ctgccctatc aacccataca agtccaccat cagactgtc atctacaaga
3241 gccgcctcta cttgctctgg cttgagcaga aggagatcac caagcaaact ggcaactcca
3301 aggatggtta ccaaactgag actgactacc gctacgagtt gaagttggct cacatccgct
3361 acgatggtac ctggaacact ccaatcacct tcgatgtcaa caagaagatc agcgagttga
3421 agttggagaa gaaccgtgct cctggtctct actgcgctgg ttaccaaggt gaggacaccc
3481 tcttggtcat gttctacaac cagcaagaca cccttgactc ctacaagaac gcttccatgc
3541 aaggtctcta catcttcgct gacatggctt ccaaggacat gactccagag caaagcaacg
3601 tctaccgtga caactcctac caacagttcg acaccaacaa cgtcaggcgt gtcaacaaca
3661 gatacgctga ggactacgag atcccaagct ctgtcagctc tcgcaaggac tacggctggg
3721 gtgactacta ccctcagcat gtgtacaacg gtgacatccc aaccatcaac tacaaggctg
```

Figure 22 (cont)

```
3781 cctcttccga cctcaaaatc tacatcagcc caaagctcag gatcatccac aacggctacg
3841 agggtcagaa gaggaaccag tgcaacttga tgaacaagta cggcaagttg ggtgacaagt
3901 tcattgtcta cacctctctt ggtgtcaacc caaacaacag ctccaacaag ctcatgttct
3961 acccagtcta ccaatactct ggcaacacct ctggtctcaa ccagggtaga ctcttgttcc
4021 acagggacac cacctaccca agcaaggtgg aggcttggat tcctggtgcc aagaggtccc
4081 tcaccaacca gaacgctgcc attggtgatg actacgccac agactccctc aacaagcctg
4141 atgacctcaa gcagtacatc ttcatgactg actccaaggg cacagccact gatgtctctg
4201 gtccagtgga gatcaacact gcaatcagcc cagccaaggt ccaaatcatt gtcaaggctg
4261 gtggcaagga gcaaaccttc acagctgaca aggatgtctc catccagcca agcccatcct
4321 tcgatgagat gaactaccaa ttcaacgctc ttgagattga tggttctggc ctcaacttca
4381 tcaacaactc tgcttccatt gatgtcacct tcactgcctt cgctgaggat ggccgcaagt
4441 tgggttacga gagcttctcc atcccagtca cccttaaggt ttccactgac aacgcactca
4501 cccttcatca caacgagaac ggtgctcagt acatgcaatg caaagctac cgcaccaggt
4561 tgaacaccct cttcgcaagg caacttgtgg cccgtgccac cacaggcatt gacaccatcc
4621 tcagcatgga gacccagaac atccaagagc cacagttggg caagggtttc tacgccacct
4681 tcgtcatccc accttacaac ctcagcactc atggtgatga gaggtggttc aagctctaca
4741 tcaagcacgt ggttgacaac aactcccaca tcatctactc tggtcaactc actgacacca
4801 acatcaacat caccctcttc atcccacttg acgatgtccc actcaaccag gactaccatg
4861 ccaaggtcta catgaccttc aagaagtctc catctgatgg cacctggtgg ggtccacact
4921 tcgtccgtga tgacaagggc atcgtcacca tcaacccaaa gtccatcctc acccacttcg
4981 agtctgtcaa cgttctcaac aacatctcct ctgagccaat ggacttctct ggtgccaact
5041 ccctctactt ctgggagttg ttctactaca caccaatgct tgtggctcaa aggttgctcc
5101 atgagcagaa cttcgatgag gccaacaggt ggctcaagta cgtctggagc ccatctggtt
5161 acattgtgca tggtcaaatc cagaactacc aatggaacgt caggccattg cttgaggaca
5221 cctcctggaa ctctgaccca cttgactctg tggaccctga tgctgtggct caacatgacc
5281 caatgcacta caaggtctcc accttcatga ggaccttgga cctcttgatt gccagaggtg
5341 accatgctta ccgccaattg gagagggaca ccctcaacga ggcaaagatg tggtacatgc
5401 aagctctcca cctcttgggt gacaagccat acctcccact cagcaccact tggtccgacc
5461 caaggttgga ccgtgctgct gacatcacca ctcagaacgc tcatgactct gccattgttg
5521 ctctcaggca gaacatccca actcctgctc cactctccct cagatctgct aacaccctca
5581 ctgacttgtt cctcccacag atcaacgagg tcatgatgaa ctactggcaa accttggctc
5641 aaagggtcta caacctcaga cacaacctct ccattgatgg tcaaccactc tacctcccaa
5701 tctacgccac accagctgac ccaaaggctc ttctctctgc tgctggtgct accagccaag
5761 gtggtggcaa gctcccagag tccttcatgt ccctctggag gttcccacac atgttggaga
5821 acgcccgtgg catggtctcc caactcaccc agttcggttc caccctccag aacatcattg
5881 agaggcaaga tgctgaggct ctcaacgctt tgctccagaa ccaggcagct gagttgatcc
5941 tcaccaactt gtccatccaa gacaagacca ttgaggagct tgatgctgag aagacagtcc
6001 ttgagaagag caaggctggt gcccaatctc gcttcgactc ctacggcaag ctctacgatg
6061 agaacatcaa cgctggtgag aaccaggcca tgaccctcag ggcttccgca gctggtctca
6121 ccactgctgt ccaagcctct cgcttggctg gtgcagctgc tgacctcgtt ccaaacatct
6181 tcggtttcgc tggtggtggc tccagatggg gtgccattgc tgaggctacc ggttacgtca
6241 tggagttctc tgccaacgtc atgaacactg aggctgacaa gatcagccaa tctgagacct
6301 acagaaggcg ccgtcaagag tgggagatcc aaaggaacaa cgctgaggca gagttgaagc
6361 aaatcgatgc tcaactcaag tccttggctg tcagaaggga ggctgctgtc ctccagaaga
6421 cctccctcaa gacccaacag gagcaaaccc agtcccagtt ggctttcctc caaaggaagt
6481 tctccaacca ggctctctac aactggctca gaggccgctt ggctgccatc tacttccaat
6541 tctacgacct tgctgtggcc aggtgcctca tggctgagca agcctaccgc tgggagttga
6601 acgatgactc cgccaggttc atcaagccag gtgcttggca aggcacctac gctggtctcc
6661 ttgctggtga gaccctcatg ctctccttgg ctcaaatgga ggatgctcac ctcaagaggg
6721 acaagagggc tttggaggtg gagaggacag tctcccttgc tgaggtctac gctggtctcc
6781 caaaggacaa cggtccattc tcccttgctc aagagattga caagttggtc agccaaggtt
6841 ctggttctgc tggttctggt aacaacaact tggctttcgg cgctggtact gacaccaaga
6901 cctccctcca agcctctgtc tccttcgctg acctcaagat cagggaggac tacccagctt
6961 cccttggcaa gatcaggcgc atcaagcaaa tctctgtcac cctcccagct ctcttgggtc
7021 cataccaaga tgtccaagca atcctctcct acggtgacaa ggctggtttg gcgaacggtt
7081 gcgaggctct tgctgtctct catggcatga acgactctgg tcaattccaa cttgacttca
7141 acgatggcaa gttcctccca ttcgagggca ttgccattga ccaaggcacc ctcaccctct
7201 ccttcccaaa cgcttccatg ccagagaagg gaaagcaagc caccatgctc aagaccctca
7261 acgatatcat cctccacatc aggtacacca tcaagtgagc tc
```

Figure 23

```
   1 ccatggctaa cgagtccgtc aaggagatcc cagacgtcct caagtcccaa tgcggtttca
  61 actgcctcac tgacatctcc cacagctcct tcaacgagtt cagacaacaa gtctctgagc
 121 acctctcctg gtccgagacc catgacctct accatgacgc tcagcaagct cagaaggaca
 181 acaggctcta cgaggctagg atcctcaaga gggctaaccc acaactccag aacgctgtcc
 241 acctcgccat cttggctcca aacgctgagt tgattggtta caacaaccag ttctctggca
 301 gagctagcca gtacgtggct cctggtacag tctcctccat gttcagccca gccgcttacc
 361 tcactgagtt gtaccgcgag gctaggaacc ttcatgcttc tgactccgtc tactacttgg
 421 acacacgcag accagacctc aagagcatgg ccctcagcca acagaacatg gacattgagt
 481 tgtccaccct ctccttgagc aacgagcttc tcttggagtc catcaagact gagagcaagt
 541 tggagaacta caccaaggtc atggagatgc tctccacctt cagaccaagc ggtgcaactc
 601 cataccatga tgcctacgag aacgtcaggg aggtcatcca acttcaagac cctggtcttg
 661 agcaactcaa cgcttctcca gccattgctg gtttgatgca ccaggcatcc ttgctcggta
 721 tcaacgcctc catctctcct gagttgttca acatcttgac tgaggagatc actgagggca
 781 acgctgagga gttgtacaag aagaacttcg gcaacattga gccagcctct cttgcaatgc
 841 ctgagtacct caagaggtac tacaacttgt ctgatgagga gctttctcaa ttcattggca
 901 aggcttccaa cttcggtcaa caggagtaca gcaacaacca gctcatcact ccagttgtga
 961 actcctctga tggcactgtg aaggtctacc gcatcacacg tgagtacacc acaaacgcct
1021 accaaatgga tgttgagttg ttcccattcg gtggtgagaa ctacagactt gactacaagt
1081 tcaagaactt ctacaacgcc tcctacctct ccatcaagtt gaacgacaag agggagcttg
1141 tcaggactga gggtgctcct caagtgaaca ttgagtactc tgccaacatc accctcaaca
1201 cagctgacat ctctcaacca ttcgagattg gtttgaccag agtccttccc tctggctcct
1261 gggcctacgc tgcagccaag ttcactgttg aggagtacaa ccagtactct ttcctctgga
1321 agctcaacaa ggcaattcgt ctcagcagag ccactgagtt gtctcccacc atcttggagg
1381 gcattgtgag gtctgtcaac cttcaacttg acatcaacac tgatgtgctt ggcaaggtct
1441 tcctcaccaa gtactacatg caacgctacg ccatccatgc tgagactgca ctcatcctct
1501 gcaacgcacc catctctcaa cgctcctacg acaaccagcc ttcccagttc gacaggctct
1561 tcaacactcc tctcttgaac ggccagtact ctccactgg tgatgaggag attgacctca
1621 actctggctc cacaggtgac tggagaaaga ccatcttgaa gagggccttc aacattgatg
1681 atgtctctct cttccgtctc ttgaagatca cagatcacga caacaaggat ggcaagatca
1741 agaacaactt gaagaacctt tccaacctct acattggcaa gttgcttgca gacatccacc
1801 aactcaccat tgatgagttg gacctcttgc tcattgcagt cggtgagggc aagaccaacc
1861 tctctgcaat ctctgacaag cagttggcaa ccctcactgc gaagttgaac accatccact
1921 cctggcttca cacccagaag tggtctgtct tccaactctt catcatgacc agcacctcct
1981 acaacaagac cctcactcct gagatcaaga acctcttgga cacagtctac cacggtctcc
2041 aaggcttcga caaggacaag gctgacttgc ttcatgtcat ggctccctac attgcagcca
2101 ccctccaact ctcctctgag aacgtggctc actctgtctt gctctgggct gacaagctcc
2161 aacctggtga tggtgccatg actgctgaga gttctggga ctggctcaac accaagtaca
2221 caccaggctc ctctgaggct gttgagactc aagagcacat tgtgcaatac tgccaggctc
2281 ttgcacagtt ggagatggtc taccactcca ctggcatcaa cgagaacgct ttcagactct
2341 tcgtcaccaa gcctgagatg ttcggtgctg ccacaggtgc tgcacctgct catgatgctc
2401 tctccctcat catgttgacc aggttcgctg actgggtcaa cgctcttggt gagaaggctt
2461 cctctgtctt ggctgcccttc gaggccaact ccctcactgc tgagcaactt gctgatgcca
2521 tgaaccttga tgccaacctc ttgctccaag cttccattca agctcagaac caccaacacc
2581 tcccacctgt cactccagag aacgctttct cctgctggac ctccatcaac accatcctcc
2641 aatgggtcaa cgtggctcag caactcaacg tggctccaca aggtgtctct gctttggtcg
2701 gtcttgacta catccagtcc atgaaggaga caccaaccta cgctcaatgg gagaacgcag
2761 ctggtgtctt gactgctggt ctcaactccc aacaggccaa caccctccat gctttcttgg
2821 atgagtctcg ctctgctgcc ctctccacct actacatcag gcaagtcgcc aaggcagctg
2881 ctgccatcaa gtctcgcgat gacctctacc aatacctcct cattgacaac aggtctctg
2941 ctgccatcaa gaccaccagg atcgctgagg ccatcgcttc catccaactc tacgtcaacc
3001 gcgctcttga aacgttgag gagaacgcca actctggtgt catctctcgc caattcttca
3061 tcgactggga caagtacaac aagaggtact ccacctgggc tggtgtctct caacttgtct
3121 actcccaga gaactacatt gacccaacca tgaggattgg tcagaccaag atgatggatg
3181 ctctcttgca atctgtctcc caaagccaac tcaacgctga cactgtggag gatgccttca
3241 tgagctacct cacctccttc gagcaagttg ccaacctcaa ggtcatctct gcttaccatg
3301 acaacatcaa caacgaccaa ggtctcacct acttcattgg tctctctgag actgatgctg
3361 gtgagtacta ctggagatcc gtggaccaca gcaagttcaa cgatggcaag ttcgctgcaa
3421 acgcttggtc tgagtggcac aagattgact gccctatcaa cccatacaag tccaccatca
3481 gacctgtcat ctacaagagc cgcctctact gctctggct tgagcagaag agatcacca
3541 agcaaactgg caactccaag gatggttacc aaactgagac tgactaccgc tacgagttga
3601 agttggctca catccgctac gatggtacct ggaacactcc aatcaccttc gatgtcaaca
3661 agaagatcag cgagttgaag ttggagaaga ccgtgctcc tggtctctac tgcgctggtt
3721 accaaggtga ggacacctc ttggtcatgt tctacaacca gcaagacacc cttgactcct
```

Figure 23 (cont.)

```
3781 acaagaacgc ttccatgcaa ggtctctaca tcttcgctga catggcttcc aaggacatga
3841 ctccagagca aagcaacgtc taccgtgaca actcctacca acagttcgac accaacaacg
3901 tcaggcgtgt caacaacaga tacgctgagg actacgagat cccaagctct gtcagctctc
3961 gcaaggacta cggctggggt gactactacc tcagcatggt gtacaacggt gacatcccaa
4021 ccatcaacta caaggctgcc tcttccgacc tcaaaatcta catcagccca aagctcagga
4081 tcatccacaa cggctacgag ggtcagaaga ggaaccagtg caacttgatg aacaagtacg
4141 gcaagttggg tgacaagttc attgtctaca cctctcttgg tgtcaaccca acaacagct
4201 ccaacaagct catgttctac ccagtctacc aatactctgg caacacctct ggtctcaacc
4261 agggtagact cttgttccac agggacacca cctacccaag caaggtggag cttggattc
4321 ctggtgccaa gaggtccctc accaaccaga acgctgccat tggtgatgac tacgccacag
4381 actccctcaa caagcctgat gacctcaagc agtacatctt catgactgac tccaagggca
4441 cagccactga tgtctctggt ccagtggaga tcaacactgc aatcagccca gccaaggtcc
4501 aaatcattgt caaggctggt ggcaaggagc aaaccttcac agctgacaag gatgtctcca
4561 tccagccaag cccatccttc gatgagatga actaccaatt caacgctctt gagattgatg
4621 gttctggcct caacttcatc aacaactctg cttccattga tgtcaccttc actgccttcg
4681 ctgaggatgg ccgcaagttg ggttacgaga gcttctccat cccagtcacc cttaaggttt
4741 ccactgacaa cgcactcacc cttcatcaca acgagaacgg tgctcagtac atgcaatggc
4801 aaagctaccg caccaggttg aacaccctct tcgcaaggca acttgtggcc cgtgccacca
4861 caggcattga caccatcctc agcatggaga cccagaacat ccaagagcca cagttgggca
4921 agggtttcta cgccaccttc gtcatcccac cttacaacct cagcactcat ggtgatgaga
4981 ggtggttcaa gctctacatc aagcacgtgg ttgacaacaa ctcccacatc atctactctg
5041 gtcaactcac tgacaccaac atcaacatca ccctcttcat cccacttgac gatgtcccac
5101 tcaaccagga ctaccatgcc aaggtctaca tgaccttcaa gaagtctcca tctgatggca
5161 cctggtgggg tccacacttc gtccgtgatg acaagggcat cgtcaccatc aacccaaagt
5221 ccatcctcac ccacttcgag tctgtcaacg ttctcaacaa catctcctct gagccaatgg
5281 acttctctgg tgccaactcc ctctacttct gggagttgtt ctactacaca ccaatgcttg
5341 tggctcaaag gttgctccat gagcagaact tcgatgaggc caacaggtgg ctcaagtacg
5401 tctggagccc atctggttac attgtgcatg gtcaaatcca gaactaccaa tggaacgtca
5461 ggccattgct tgaggacacc tcctggaact ctgacccact tgactctgtg gaccctgatg
5521 ctgtggctca acatgaccca atgcactaca agtaggagct c
```

Figure 24

```
   1 ccatggctaa cgagtccgtc aaggagatcc cagacgtcct caagtcccaa tgcggtttca
  61 actgcctcac tgacatctcc cacagctcct tcaacgagtt cagacaacaa gtctctgagc
 121 acctctcctg gtccgagacc catgacctct accatgacgc tcagcaagct cagaaggaca
 181 acaggctcta cgaggctagg atcctcaaga gggctaaccc acaactccag aacgctgtcc
 241 acctcgccat cttggctcca aacgctgagt tgattggtta caacaaccag ttctctggca
 301 gagctagcca gtacgtggct cctggtacag tctcctccat gttcagccca gccgcttacc
 361 tcactgagtt gtaccgcgag gctaggaacc ttcatgcttc tgactccgtc tactacttgg
 421 acacacgcag accagacctc aagagcatgg ccctcagcca acagaacatg gacattgagt
 481 tgtccaccct ctccttgagc aacgagcttc tcttggagtc catcaagact gagagcaagt
 541 tggagaacta caccaaggtc atggagatgc tctccacctt cagaccaagc ggtgcaactc
 601 cataccatga tgcctacgag aacgtcaggg aggtcatcca acttcaagac cctggtcttg
 661 agcaactcaa cgcttctcca gccattgctg gtttgatgca ccaggcatcc ttgctcggta
 721 tcaacgcctc catctctcct gagttgttca acatcttgac tgaggagatc actgagggca
 781 acgctgagga gttgtacaag aagaacttcg gcaacattga gccagcctct cttgcaatgc
 841 ctgagtacct caagaggtac tacaacttgt ctgatgagga gctttctcaa ttcattggca
 901 aggcttccaa cttcggtcaa caggagtaca gcaacaacca gctcatcact ccagttgtga
 961 actcctctga tggcactgtg aaggtctacc gcatcacacg tgagtacacc acaaacgcct
1021 accaaatgga tgttgagttg ttcccattcg gtggtgagaa ctacagactt gactacaagt
1081 tcaagaactt ctacaacgcc tcctacctct ccatcaagtt gaacgacaag agggagcttg
1141 tcaggactga gggtgctcct caagtgaaca ttgagtactc tgccaacatc accctcaaca
1201 cagctgacat ctctcaacca ttcgagattg gttgaccag agtccttccc tctggctcct
1261 gggcctacgc tgcagccaag ttcactgttg aggagtacaa ccagtactct ttcctcttga
1321 agctcaacaa ggcaattcgt ctcagcagag ccactgagtt gtctcccacc atcttggagg
1381 gcattgtgag gtctgtcaac cttcaacttg acatcaacac tgatgtgctt ggcaaggtct
1441 tcctcaccaa gtactacatg caacgctacg ccatccatgc tgagactgca ctcatcctct
1501 gcaacgcacc catctctcaa cgctcctacg acaaccagcc ttcccagttc gacaggctct
1561 tcaacactcc tctcttgaac ggccagtact ctccactgg tgatgaggag attgacctca
1621 actctggctc cacaggtgac tggagaaaga ccatcttgaa gagggccttc aacattgatg
1681 atgtctctct cttccgtctc ttgaagatca cagatcacga caacaaggat ggcaagatca
1741 agaacaactt gaagaacctt tccaacctct acattggcaa gttgcttgca gacatccacc
1801 aactcaccat tgatgagttg gacctcttgc tcattgcagt cggtgagggc aagccaacc
1861 tctctgcaat ctctgacaag cagttggcaa ccctcatcag gaagttgaac accatcacct
1921 cctggcttca cacccagaag tggtctgtct tccaactctt catcatgacc agcacctcct
1981 acaacaagac cctcactcct gagatcaaga acctcttgga cacagtctac cacggtctcc
2041 aaggcttcga caaggacaag gctgacttgc ttcatgtcat ggctccctac attgcagcca
2101 ccctccaact ctcctctgag aacgtggctc actctgtctt gctctgggct gacaagctcc
2161 aacctggtga tggtgccatg actgctgaga agttctggga ctggctcaac accaagtaca
2221 caccaggctc tctgaggct gttgagactc aagagcacat tgtgcaatac tgccaggctc
2281 ttgcacagtt ggagatggtc taccactcca ctggcatcaa cgagaacgct ttcagactct
2341 tcgtcaccaa gcctgagatg ttcggtgctg ccacaggtgc tgcacctgct catgatgctc
2401 tctccctcat catgttgacc aggttcgctg actgggtcaa cgctcttggt gagaaggctt
2461 cctctgtctt ggctgccttc gaggccaact ccctcactgc tgagcaactt gctgatgcca
2521 tgaaccttga tgccaacctc ttgctccaag cttccattca agctcagaac caccaacacc
2581 tcccacctgt cactccagag aacgctttct cctgctggac ctccatcaac accatcctcc
2641 aatgggtcaa cgtggctcag caactcaacg tggctccaca aggtgtctct gctttggtcg
2701 gtcttgacta catccagtcc atgaaggaga caccaaccta cgctcaatgg gagaacgcag
2761 ctggtgtctt gactgctggt ctcaactccc aacaggccaa caccctccat gcttttcttgg
2821 atgagtctcg ctctgctgcc ctctccacct actacatcag gcaagtcgcc aaggcagctg
2881 ctgccatcaa gtctcgcgat gacctctacc aatacctcct cattgacaac caggtctctg
2941 ctgccatcaa gaccaccagg atcgctgagg ccatcgcttc catccaactc tacgtcaacc
3001 gcgctcttga aacgttgag gagaacgcca actctggtgt catctctcgc caattcttca
3061 tcgactggga caagtacaac aagaggtact ccacctgggc tggtgtctct caacttgtct
3121 actacccaga gaactacatt gacccaacca tgaggattgg tcagaccaag atgatggatg
3181 ctctcttgca atctgtctcc caaagccaac tcaacgctga cactgtggag gatgccttca
3241 tgagctacct cacctccttc gagcaagttg ccaacctcaa ggtcatctct gcttaccatg
3301 acaacatcaa caacgaccaa ggtctcacct acttcattgg tctctctgag actgatgctg
3361 gtgagtacta ctggagatcc gtggaccaca gcaagttcaa cgatggcaag ttcgctgcaa
3421 acgcttggtc tgagtggcac aagattgact gccctatcaa cccatacaag tccaccatca
3481 gacctgtcat ctacaagagc cgcctctact gctctggct tgagcagaag gagatcacca
3541 agcaaactgg caactccaag gatggttacc aaactgagac tgactaccgc tacgagttga
3601 agttggctca catccgctac gatggtacct ggaacactcc aatcaccttc gatgtcaaca
3661 agaagatcag cgagttgaag ttggagaaga ccgtgctcc tggtctctac tgcgctggtt
3721 accaaggtga ggacaccctc ttggtcatgt ctacaaccaa gcaagacacc cttgactcct
```

Figure 24 (cont.)

```
3781 acaagaacgc ttccatgcaa ggtctctaca tcttcgctga catggcttcc aaggacatga
3841 ctccagagca aagcaacgtc taccgtgaca actcctacca acagttcgac accaacaacg
3901 tcaggcgtgt caacaacaga tacgctgagg actacgagat cccaagctct gtcagctctc
3961 gcaaggacta cggctggggt gactactacc tcagcatggt gtacaacggt gacatcccaa
4021 ccatcaacta caaggctgcc tcttccgacc tcaaaatcta catcagccca aagctcagga
4081 tcatccacaa cggctacgag ggtcagaaga ggaaccagtg caacttgatg aacaagtacg
4141 gcaagttggg tgacaagttc attgtctaca cctctcttgg tgtcaaccca aacaacagct
4201 ccaacaagct catgttctac ccagtctacc aatactctgg caacacctct ggtctcaacc
4261 agggtagact cttgttccac agggacacca cctacccaag caaggtggag gcttggattc
4321 ctggtgccaa gaggtccctc accaaccaga acgctgccat tggtgatgac tacgccacag
4381 actccctcaa caagcctgat gacctcaagc agtacatctt catgactgac tccaagggca
4441 cagccactga tgtctctggt ccagtggaga tcaacactgc aatcagccca gccaaggtcc
4501 aaatcattgt caaggctggt ggcaaggagc aaaccttcac agctgacaag gatgtctcca
4561 tccagccaag cccatccttc gatgagatga actaccaatt caacgctctt gagattgatg
4621 gttctggcct caacttcatc aacaactctg cttccattga tgtcaccttc actgccttcg
4681 ctgaggatgg ccgcaagttg ggttacgaga gcttctccat cccagtcacc cttaaggttt
4741 ccactgacaa cgcactcacc cttcatcaca acgagaacgg tgctcagtac atgcaatggc
4801 aaagctaccg caccaggttg aacaccctct tcgcaaggca acttgtggcc cgtgccacca
4861 caggcattga caccatcctc agcatggaga cccagaacat ccaagagcca cagttgggca
4921 agggttttcta cgccaccttc gtcatcccac cttacaacct cagcactcat ggtgatgaga
4981 ggtggttcaa gctctacatc aagcacgtgg ttgacaacaa ctcccacatc atctactctg
5041 gtcaactcac tgacaccaac atcaacatca ccctcttcat cccacttgac gatgtcccac
5101 tcaaccagga ctaccatgcc aaggtctaca tgaccttcaa gaagtctcca tctgatggca
5161 cctggtgggg tccacacttc gtccgtgatg acaagggcat cgtcaccatc aacccaaagt
5221 ccatcctcac ccacttcgag tctgtcaacg ttctcaacaa catctcctct gagccaatgg
5281 acttctctgg tgccaactcc ctctacttct gggagttgtt ctactacaca ccaatgcttg
5341 tggctcaaag gttgctccat gagcagaact tcgatgaggc caacaggtgg ctcaagtacg
5401 tctggagccc atctggttac attgtgcatg gtcaaatcca gaactaccaa tggaacgtca
5461 ggccattgct tgaggacacc tcctggaact ctgacccact tgactctgtg gaccctgatg
5521 ctgtggctca acatgaccca atgcactaca aggtctccac cttcatgagg accttggacc
5581 tcttgattgc cagaggtgac catgcttacc gccaattgga gagggacacc ctcaacgagg
5641 caaagatgtg gtacatgcaa gctctccacc tcttgggtga caagccatac ctcccactca
5701 gcaccacttg gtccgaccca aggttggacc gtgctgctga catcaccact cagaacgctc
5761 atgactctgc cattgttgct ctcaggcaga acatcccaac tcctgctcca ctctcc
```

Figure 25

```
   1 ccatggctga gttgattggt tacaacaacc agttctctgg cagagctagc cagtacgtgg
  61 ctcctggtac agtctcctcc atgttcagcc cagccgctta cctcactgag ttgtaccgcg
 121 aggctaggaa ccttcatgct tctgactccg tctactactt ggacacacgc agaccagacc
 181 tcaagagcat ggccctcagc caacagaaca tggacattga gttgtccacc ctctccttga
 241 gcaacgagct tctcttggag tccatcaaga ctgagagcaa gttggagaac tacaccaagg
 301 tcatggagat gctctccacc ttcagaccaa gcggtgcaac tccataccat gatgcctacg
 361 agaacgtcag ggaggtcatc caacttcaag accctggtct tgagcaactc aacgcttctc
 421 cagccattgc tggtttgatg caccaggcat ccttgctcgg tatcaacgcc tccatctctc
 481 ctgagttgtt caacatcttg actgaggaga tcactgaggg caacgctgag gagttgtaca
 541 agaagaactt cggcaacatt gagccagcct ctcttgcaat gcctgagtac ctcaagaggt
 601 actacaactt gtctgatgag gagctttctc aattcattgg caaggcttcc aacttcggtc
 661 aacaggagta cagcaacaac cagctcatca ctccagttgt gaactcctct gatggcactg
 721 tgaaggtcta ccgcatcaca cgtgagtaca ccacaaacgc ctaccaaatg gatgttgagt
 781 tgttcccatt cggtggtgag aactacagac ttgactacaa gttcaagaac ttctacaacg
 841 cctcctacct ctccatcaag ttgaacgaca agagggagct tgtcaggact gagggtgctc
 901 ctcaagtgaa cattgagtac tctgccaaca tcaccctcaa cacagctgac atctctcaac
 961 cattcgagat tggtttgacc agagtccttc cctctggctc ctgggcctac gctgcagcca
1021 agttcactgt tgaggagtac aaccagtact cttttcctctt gaagctcaac aaggcaattc
1081 gtctcagcag agccactgag ttgtctccca ccatcttgga gggcattgtg aggtctgtca
1141 accttcaact tgacatcaac actgatgtgc ttggcaaggt cttcctcacc aagtactaca
1201 tgcaacgcta cgccatccat gctgagactg cactcatcct gcaacgca cccatctctc
1261 aacgctccta cgacaaccag ccttcccagt cgacaggct cttcaacact cctctcttga
1321 acggccagta cttctccact ggtgatgagg agattgacct caactctggc tccacaggtg
1381 actggagaaa gaccatcttg aagagggcct tcaacattga tgatgtctct ctcttccgtc
1441 tcttgaagat cacagatcac gacaacaagg atggcaagat caagaacaac ttgaagaacc
1501 tttccaacct ctacattggc aagttgcttg cagacatcca ccaactcacc attgatgagt
1561 tggacctctt gctcattgca gtcggtgagg gcaagaccaa cctctctgca atctctgaca
1621 agcagttggc aaccctcatc aggaagttga acaccatcac ctcctggctt cacacccaga
1681 agtggtctgt cttccaactc ttcatcatga ccagcacctc ctacaacaag accctcactc
1741 ctgagatcaa gaaccttctg acacagtct accacggtct ccaaggcttc gacaaggaca
1801 aggctgactt gcttcatgtc atggctccct acattgcagc caccctccaa ctctcctctg
1861 agaacgtggc tcactctgtc ttgctctggg ctgacaagct ccaacctggt gatggtgcca
1921 tgactgctga gaagttctgg gactggctca caccaagta caccaggc cctctgagg
1981 ctgttgagac tcaagagcac attgtgcaat actgccaggc tcttgcacag ttggagatgg
2041 tctaccactc cactggcatc aacgagaacg ctttcagact cttcgtcacc aagcctgaga
2101 tgttcggtgc tgccacaggt gctgcacctg ctcatgatgc tctctccctc atcatgttga
2161 ccaggttcgc tgactgggtc aacgctcttg gtgagaaggc ttcctctgtc ttggctgcct
2221 tcgaggccaa ctcccctcact gctgagcaac ttgctgatgc catgaacctt gatgccaacc
2281 tcttgctcca agcttccatt caagctcaga accaccaaca cctcccacct gtcactccag
2341 agaacgcttt ctcctgctgg acctccatca acaccatcct ccaatgggtc aacgtggctc
2401 agcaactcaa cgtggctcca caaggtgtct ctgctttggt cggtcttgac tacatccagt
2461 ccatgaagga gacaccaacc tacgctcaat gggagaacgc agctggtgtc ttgactgctg
2521 gtctcaactc ccaacaggcc aacacccctcc atgctttctt ggatgagtct cgctctgctg
2581 ccctctccac ctactacatc aggcaagtcg ccaaggcagc tgctgccatc aagtctgcg
2641 atgacctcta ccaataccctc ctcattgaca ccaggtctc tgctgccatc aagaccacca
2701 ggatcgctga ggccatcgct tccatccaac tctacgtcaa ccgcgctctt gagaacgttg
2761 aggagaacgc caactctggt gtcatctctc gccaattctt catcgactgg gacaagtaca
2821 acaagaggta ctccacctgg gctggtgtct ctcaacttgt ctactaccca gagaactaca
2881 ttgacccaac catgaggatt ggtcagacca agatgatgga tgctctcttg caatctgtct
2941 cccaaagcca actccagctg gacactgtgg aggatgcctt catgagctac ctcacctcct
3001 tcgagcaagt tgccaacctc aaggtcatct ctgcttacca tgacaacatc aacaacgacc
3061 aaggtctcac ctacttcatt ggtctctctg agactgatgc tggtgagtac tactggagat
3121 ccgtggacca cagcaagttc aacgatggca gttcgctgc aaacgcttgg tctgagtggc
3181 acaagattga ctgccctatc aacccataca gtccaccat cagacctgtc atctacaaga
3241 gccgcctcta cttgctctgg cttgagcaga aggagatcac caagcaaact ggcaactcca
3301 aggatggtta ccaaactgag actgactacc gctacgagtt gaagttggct cacatccgct
3361 acgatggtac ctggaacact ccaatcacct tcgatgtcaa caagaagatc agcgagttga
3421 agttggagaa gaaccgtgct cctggtctct actgcgctgg ttaccaaggt gaggacaccc
3481 tcttggtcat gttctacaac cagcaagaca cccttgactc ctacaagaac gcttccatgc
3541 aaggtctcta catcttcgct gacatggctt ccaaggacat gactccagag caaagcaacg
3601 tctaccgtga caactcctac caacagttcg acaccaacaa cgtcaggcgt gtcaacaaca
3661 gatacgctga ggactacgag atcccaagct ctgtcagctc tcgcaaggac tacggctggg
3721 gtgactacta cctcagcatg gtgtacaacg gtgacatccc aaccatcaac tacaaggctg
```

Figure 25 (cont.)

```
3781 cctcttccga cctcaaaatc tacatcagcc caaagctcag gatcatccac aacggctacg
3841 agggtcagaa gaggaaccag tgcaacttga tgaacaagta cggcaagttg ggtgacaagt
3901 tcattgtcta caccctctctt ggtgtcaacc caaacaacag ctccaacaag ctcatgttct
3961 acccagtcta ccaatactct ggcaacacct ctggtctcaa ccagggtaga ctcttgttcc
4021 acagggacac cacctaccca agcaaggtgg aggcttggat tcctggtgcc aagaggtccc
4081 tcaccaacca gaacgctgcc attggtgatg actacgccac agactccctc aacaagcctg
4141 atgacctcaa gcagtacatc ttcatgactg actccaaggg cacagccact gatgtctctg
4201 gtccagtgga gatcaacact gcaatcagcc cagccaaggt ccaaatcatt gtcaaggctg
4261 gtggcaagga gcaaaccttc acagctgaca aggatgtctc catccagcca agcccatcct
4321 tcgatgagat gaactaccaa ttcaacgctc ttgagattga tggttctggc ctcaacttca
4381 tcaacaactc tgcttccatt gatgtcacct tcactgcctt cgctgaggat ggccgcaagt
4441 tgggttacga gagcttctcc atcccagtca cccttaaggt ttccactgac aacgcactca
4501 cccttcatca caacgagaac ggtgctcagt acatgcaatg gcaaagctac cgcaccaggt
4561 tgaacaccct cttcgcaagg caacttgtgg cccgtgccac cacaggcatt gacaccatcc
4621 tcagcatgga gacccagaac atccaagagc acagttggg caagggtttc tacgccacct
4681 tcgtcatccc accttacaac ctcagcactc atggtgatga gaggtggttc aagctctaca
4741 tcaagcacgt ggttgacaac aactcccaca tcatctactc tggtcaactc actgacacca
4801 acatcaacat caccctcttc atcccacttg acgatgtccc actcaaccag gactaccatg
4861 ccaaggtcta catgaccttc aagaagttctc catctgatgg cacctggtgg ggtccacact
4921 tcgtccgtga tgacaagggc atcgtcacca tcaacccaaa gtccatcctc acccacttcg
4981 agtctgtcaa cgttctcaac aacatctcct ctgagccaat ggacttctct ggtgccaact
5041 ccctctactt ctgggagttg ttctactaca caccaatgct tgtggctcaa aggttgctcc
5101 atgagcagaa cttcgatgag gccaacaggt ggctcaagta cgtctggagc ccatctggtt
5161 acattgtgca tggtcaaatc cagaactacc aatggaacgt caggccattg cttgaggaca
5221 cctcctggaa ctctgaccca cttgactctg tggaccctga tgctgtggct caacatgacc
5281 caatgcacta caagtgagct c
```

Figure 26

```
   1 ccatggctca gatctgctaa caccctcact gacttgttcc tcccacagat caacgaggtc
  61 atgatgaact actggcaaac cttggctcaa agggtctaca acctcagaca caacctctcc
 121 attgatggtc aaccactcta cctcccaatc tacgccacac cagctgaccc aaaggctctt
 181 ctctctgctg ctgtggctac cagccaaggt ggtggcaagc tcccagagtc cttcatgtcc
 241 ctctggaggt tcccacacat gttggagaac gcccgtggca tggtctccca actcacccag
 301 ttcggttcca ccctccagaa catcattgag aggcaagatg ctgaggctct caacgctttg
 361 ctccagaacc aggcagctga gttgatcctc accaacttgt ccatccaaga caagaccatt
 421 gaggagcttg atgctgagaa gacagtcctt gagaagagca aggctggtgc ccaatctcgc
 481 ttcgactcct acggcaagct ctacgatgag aacatcaacg ctggtgagaa ccaggccatg
 541 accctcaggg cttccgcagc tggtctcacc actgctgtcc aagcctctcg cttggctggt
 601 gcagctgctg acctcgttcc aaacatcttc ggtttcgctg gtggtggctc cagatggggt
 661 gccattgctg aggctaccgg ttacgtcatg gagttctctg ccaacgtcat gaacactgag
 721 gctgacaaga tcagccaatc tgagacctac agaaggcgcc gtcaagagtg ggagatccaa
 781 aggaacaacg ctgaggcaga gttgaagcaa atcgatgctc aactcaagtc cttggctgtc
 841 agaagggagg ctgctgtcct ccagaagacc tccctcaaga cccaacagga gcaaacccag
 901 tcccagttgg cttttcctcca aaggaagttc tccaaccagg ctctctacaa ctggctcaga
 961 ggccgcttgg ctgccatcta cttccaattc tacgaccttg ctgtggccag gtgcctcatg
1021 gctgagcaag cctaccgctg ggagttgaac gatgactccg ccaggttcat caagccaggt
1081 gcttggcaag cacctacgc tggtctcctt gctggtgaga ccctcatgct ctccttggct
1141 caaatggagg atgctcacct caagagggac aagagggctt tggaggtgga gaggacagtc
1201 tcccttgctg aggtctacgc tggtctccca aaggacaacg gtccattctc ccttgctcaa
1261 gagattgaca agttggtcag ccaaggttct ggttctgctg gttctggtaa caacaacttg
1321 gctttcggcg ctggtactga caccaagacc tccctccaag cctctgtctc cttcgctgac
1381 ctcaagatca gggaggacta cccagcttcc cttggcaaga tcaggcgcat caagcaaatc
1441 tctgtcaccc tcccagctct cttgggtcca taccaagatg tccaagcaat cctctcctac
1501 ggtgacaagg ctggtttggc gaacggttgc gaggctcttg ctgtctctca tggcatgaac
1561 gactctggtc aattccaact tgacttcaac gatggcaagt tcctcccatt cgagggcatt
1621 gccattgacc aaggcaccct caccctctcc ttcccaaacg cttccatgcc agagaaggga
1681 aagcaagcca ccatgctcaa gaccctcaac gatatcatcc tccacatcag gtacaccatc
1741 aagtgagctc
```

NCBI Sequence Viewer

FIG. 27

```
   1 mnesvkeipd vlksqcgfnc ltdishssfn efrqqvsehl swsethdlyh daqqaqkdnr
  61 lyearilkra npqlqnavhl ailapnaeli gynnqfsgra sqyvapgtvs smfspaaylt
 121 elyrearnlh asdsvyyldt rrpdlksmal sqqnmdiels tlslsneill esikteskle
 181 nytkvmemls tfrpsgatpy hdayenvrev iqlqdpgleq lnaspaiagl mhqasllgin
 241 asispelfni lteeitegna eelykknfgn iepaslampe ylkryynisd eeisqfigka
 301 snfgqqeysn nqlitpvvns sdgtvkvyri treyttnayq mdvelfpfgg enyrldykfh
 361 nfvnasvisi kindkrelvr tegapqvnie ysanitlnta disqpfeigl trvlpsgswa
 421 yaaakftvee ynqysfllki nkairlsrat elsptilegi vrsvnlqldi ntdvlgkvfl
 481 tkyymqryai haetalilcn apisqrsydn qpsqfdrlfn tpllngqyfs tgdeeidlns
 541 gstgdwrkti lkrafniddv slfrllkitd hdnkdgkikn nlknisnlyi gklladihql
 601 tideldllli avgegktnls aisdkqlatl irklntitsw lhtqkwsvfq lfimtstsyn
 661 ktltpeiknl ldtvyhglqg fdkdkadllh vmapyiaatl qlssenvahs vllwadklqp
 721 gdgamtaekf wdwlntkytp gsseavetqe hivqycqala qlemvyhstg inenafrlfv
 781 tkpemfgaat gaapahdais limltrfadw vnalgekass vlaafeansl taeqladamn
 841 ldanllllgas iqaqnhqhlp pvtpenafsc wtsintilqw vnvaqqlnva pqgvsalvgl
 901 dyiqsmketp tyaqwenaag vltaglnsqq antlhaflde srsaalstyy irqvakaaaa
 961 iksrddlyqy llidnqvsaa ikttriaeai asiqlyvnra lenveenans gvisrqffid
1021 wdkynkryst wagvsqlvyy penyidptmr icqtkmmdal lqsvscsqln adtvedafms
1081 yltsfeqvan lkvisayhdn inndqgltyf iglsetdage yywrsvdhsk fndgkfaana
1141 wsewhkidcp inpvksctirp viyksrlyll wleqkeitkq tgnskdgyqt etdyryelkl
1201 ahirydgtwn tpitfdvnkk iselkleknr apglycagyq gedtllvmfy nqqdtldsyk
1261 nasmqglyif admaskdmtp eqsnvyrdns yqqfdtnnvr rvnnryaedv eipssvssrk
1321 dygwqdyyls mvyngdipti nykaassdlk iyispklrii hngyeggkrn qcnlmnkygk
1381 lgdkfivyts lgvnpnnssn klmfypvyqy sgntsglnqq rllfhrdtty pskveawipq
1441 akrsltnqna aigddyatds lnkpddlkqy ifmtdskgta tdvsgpvein taispakvqi
1501 ivkaggkeqt ftadkdvsiq pspsfdemny qfnaleidgs glnfinnsas idvtftafae
1561 dgrklgyesf sipvtlkvst dnaltlhhne ngaqymqwqs yrtrlntlfa rqlvarattg
1621 idtilsmetq niqepqlgkg fyatfvippy nlsthgderw fklyikhvvd nnshiiysgq
1681 ltdtninitl fiplddvpln qdyhakvymt fkkspsdgtw wgphfvrddk givtinpksi
1741 lthfesvnvl nnissepmdf sganslyfwe lfyytpmlva qrllheqnfd eanrwlkyvw
1801 spsgyivhgq iqnyqwnvrp lledtswnsd pldsvdpdav aqhdpmhykv stfmrtldll
1861 iargdhayrq lerdtlneak mwymqalhll gdkpylplst twsdprldra adittqnahd
1921 saivalrqni ptpaplslrs antltdlflp qinevmmnyw qtlaqrrynl rhnlsidgqp
1981 lylpiyatpa dpkallsaav atsqgggklp esfmslwrfp hmlenargmv sqltqfgstl
2041 qniierqdae alnallqnqa aeliltnlsi qdktieelda ektvlekska gaqsrfdsyg
2101 klydeninag enqamtlras aaglttavqa srlagaaadl vpnifgfagg gsrwgaiaea
2161 tgyvmefsan vmnteadkis qsetyrrrrq eweiqrnnae aelkqidaql kslavrreaa
2221 vlqktslktq qeqtqsqlaf lqrkfsnqal ynwlrgrlaa iyfqfydlav arclmaeqay
2281 rwelnddsar fikpgawqgt yagllagetl mlslaqmeda hlkrdkrale vertvslaev
2341 yaglpkdngp fslaqeidkl vsqgsgsags gnnnlafgag tdtktslqas vsfadlkire
2401 dypaslgkir rikqisvtlp allgpyqdvq ailsygdkag langcealav shgmndsgqf
2461 qldfndgkfl pfegiaidqg tltlsfpnas mpekgkqatm lktlndiilh irytik
//
```

FIG. 28

Table 1. Quantitative analysis of protein expression of transgenic plants carrying various Toxin A construct

| Construct | No. of lines examined | No. of positive lines | Average level (ppm) | Highest level (ppm) |
|---|---|---|---|---|
| pDAB7031 | 60 | 37 (61%) | 90 | 1056 |
| pDAB7036 | 60 | 30 (50%) | 65 | 546 |
| pDAB7035 | 57 | 22 (38%) | 71 | 799 |
| pDAB7033 | 41 | 24 (58%) | 251 | 1594 |
| pDAB7034 | 42 | 29 (69%) | 135 | 1249 |
| pDAB7032 | 32 | 0 (0%) | 0 | 0 |

FIG 29

Table 2. Comparison of the protein expression and insecticidal activity between the transgenic plants carrying Toxin A and osmotin-Toxin A gene constructs

| Gene Construct | pDAB7031 (A0) | pDAB7026 (osm-A0) | pDAB7033 (A1/ ΔC) | pDAB7027 (osm-A1/ΔC) | pDAB7032 (A2) | pDAB7028 (osm-A2) |
|---|---|---|---|---|---|---|
| No. of plants examined | 340[a] | 274[b] | 41 | 32 | 32 | 25 |
| Average level of expressing plants | 78 (23%) | 106 (39%) | 24 (58%) | 29 (90%) | 0 (0%) | 10 (40%) |
| Average level of all examined plants (ppm) | 67 | 390 | 251 | 1131 | 0 | 33 |
| Highest expression level observed (ppm) | 15 | 152 | 146 | 1058 | 0 | 13 |
| No. of high expresser (>700 ppm) | 2 (0.6%) | 13 (4.8%) | 2 (4.8%) | 10 (31%) | 0 (0%) | 0 (0%) |
| No. of insect-resistant lines | 1 (0.3%) | 12 (4.4%) | ND | ND | ND | ND | a: Include 60 plants shown in Table 1. b: Bioassays were not performed on the first 15 plants.
ND: not determined

FIG. 30

Table 3. Summary of bioassay results of 274 transgenic Arabidopsis lines with construct pDAB7026

| Plant Line | T-DNA copy No.* | Protein (T₀) | No. of T₁ plants examined | No. of high expressers | Protein of high expressers (T₁) | No. of active T₁ plants |
|---|---|---|---|---|---|---|
| 7026-011 | 1 | 7161 | 71 | 71 (100.0%) | 761-7860 | 71 (100%) |
| 7026-294 | 1 | 1707 | 32 | 30 (90.6%) | 914-2400 | 30 (90.6%) |
| 7026-293 | 2 | 2133 | 32 | 22 (68.7%) | 985-5120 | 22 (68.7%) |
| 7026-150 | 1 | 2327 | 32 | 20 (62.5%) | 1219-3213 | 20 (62.5%) |
| 7026-190 | ND | 1505 | 32 | 19 (59.3%) | 1254-2271 | 19 (59.3%) |
| 7026-286 | 1 | 4265 | 32 | 19 (59.3%) | 468-3657 | 19 (59.3%) |
| 7026-122 | 3 | 1707 | 32 | 15 (46.8%) | 472-2388 | 15 (46.8%) |
| 7026-127 | 1 | 379 | 32 | 9 (28.1%) | 486-1969 | 8 (25.0%) |
| 7026-057 | 1 | 2725 | 38 | 9 (23.6%) | 670-1844 | 7 (18.4%) |
| 7026-195 | 1 | 1280 | 32 | 0 (0.0%) | - | 0 (0.0%) |
| Total | | | 333 | 214 (64.3%) | | 211 (63.3%) |

*: T-DNA copy number was determined by Southern blot analysis. ND, not determined

FIG. 31

Table 4. Average insect mortality of high and low expressers of T₁ transgenic plants with construct pDAB7026

| Plant Line | Average insect mortality for high expressers | Average insect mortality for low or non-expressers | Average insect mortality for the control plants |
| --- | --- | --- | --- |
| 7026-011 | 99.8% | - | 16.9% |
| 7026-294 | 93.8% | 15.6% | 7.8% |
| 7026-293 | 100.0% | 12.5% | 7.8% |
| 7026-150 | 97.0% | 8.3% | 12.0% |
| 7026-190 | 98.9% | 25.7% | 20.3% |
| 7026-286 | 93.8% | 15.6% | 12.0% |
| 7026-122 | 95.0% | 12.3% | 20.3% |
| 7026-127 | 100.0% | 20.2% | 16.3% |
| 7026-057 | 100.0% | 17.1% | 12.5% |
| Total | 97.2% | 15.9% | 14.4% |

*: plants transformed with GUS gene construct

FIG. 32

Table 5. Analysis of protein expression and insect resistance of $T_1$ progeny of transgenic line which showed high Toxin A expression, but low activity at $T_0$ generation. with construct pDAB7026

| Plant Line | Protein ($T_0$) (ppm) | Insect Mortality ($T_0$) | No. of $T_1$ plants examined | No. of high expressers ($T_1$) | Protein of high expressers | No. of active $T_1$ plants |
|---|---|---|---|---|---|---|
| 7026-101 | 2133 | 25.0% | 32 | 1 (3.1%) | 2312 | 1 (3.1%) |
| 7026-126 | 1829 | 62.5% | 32 | 2 (6.2%) | 2270-2312 | 2 (6.2%) |
| 7026-268 | 1228 | 37.5% | 32 | 0 (0.0%) | - | 0 (0.0%) |
| 7026-298 | 1224 | 40.0% | 32 | 8 (25.0%) | 1219-3213 | 8 (25.0%) |

FIG. 33

Table 6. Multi-generation analysis of insect-resistance of transgenic line 7026-011

| Plant generation | Toxin A protein expression (ppm) | No. of plants examined | No. of insects used in assays | No. of insects survived | Insect mortality for control plants |
|---|---|---|---|---|---|
| T0 | 7161 | 1 | ND | ND | ND |
| T1 | 761-7860 | 71 | 568 | 1 | 16.9% |
| T2 | 611-3662 | 76 | 608 | 1 | 14.0% |
| T3 | 639-31211 | 95 | 760 | 0 | 7.2% |
| T4 | 2000-10567 | 96

SEQUENCE LISTING

<160> NUMBER OF SEQ ID NOS: 10

<210> SEQ ID NO 1
<211> LENGTH: 40
<212> TYPE: DNA
<213> ORGANISM: Nicotiana tabacum

<400> SEQUENCE: 1
tatccaacaa cccaacttgt taaaaaaaat gtccaacaac                40

<210> SEQ ID NO 2
<211> LENGTH: 40
<212> TYPE: DNA
<213> ORGANISM: Nicotiana tabacum

<400> SEQUENCE: 2
tatccaacaa cccaacttgt taaaaaaaat ttccaacaac                40

<210> SEQ ID NO 3
<211> LENGTH: 260
<212> TYPE: DNA
<213> ORGANISM: Nicotiana tabacum

<400> SEQUENCE: 3
agtggctatt tctgtaataa gatccacctt ttggtcaaat tattctatcg acacgttagt      60
aagacaatct atttgactcg ttttatagt tacgtacttt gtttgaagtg atcaagtcat      120
gatctttgct gtaataaacc taagacctga ataagagtca catatgtatt tttgtcttga    180
tgttatatag atcaataatg catttggatt atcgttttta tattgttttt cttttgaagt    240
tttagtaaag tcttaagctt                                                260

<210> SEQ ID NO 4
<211> LENGTH: 2516
<212> TYPE: PRT
<213> ORGANISM: Photorabus luminescens

<400> SEQUENCE: 4

Met Asn Glu Ser Val Lys Glu Ile Pro Asp Val Leu Lys Ser Gln Cys
1               5                   10                  15

Gly Phe Asn Cys Leu Thr Asp Ile Ser His Ser Ser Phe Asn Glu Phe
                20                  25                  30

Arg Gln Gln Val Ser Glu His Leu Ser Trp Ser Glu Thr His Asp Leu
            35                  40                  45

Tyr His Asp Ala Gln Gln Ala Gln Lys Asp Asn Arg Leu Tyr Glu Ala
        50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
                100                 105                 110

Phe Ser Pro Ala Ala Tyr Leu Thr Glu Leu Tyr Arg Glu Ala Arg Asn
            115                 120                 125

Leu His Ala Ser Asp Ser Val Tyr Tyr Leu Asp Thr Arg Arg Pro Asp
        130                 135                 140

Leu Lys Ser Met Ala Leu Ser Gln Gln Asn Met Asp Ile Glu Leu Ser
145                 150                 155                 160

```
Thr Leu Ser Leu Ser Asn Glu Leu Leu Leu Glu Ser Ile Lys Thr Glu
            165                 170                 175
Ser Lys Leu Glu Asn Tyr Thr Lys Val Met Glu Met Leu Ser Thr Phe
        180                 185                 190
Arg Pro Ser Gly Ala Thr Pro Tyr His Asp Ala Tyr Glu Asn Val Arg
        195                 200                 205
Glu Val Ile Gln Leu Gln Asp Pro Gly Leu Glu Gln Leu Asn Ala Ser
    210                 215                 220
Pro Ala Ile Ala Gly Leu Met His Gln Ala Ser Leu Leu Gly Ile Asn
225                 230                 235                 240
Ala Ser Ile Ser Pro Glu Leu Phe Asn Ile Leu Thr Glu Glu Ile Thr
                245                 250                 255
Glu Gly Asn Ala Glu Glu Leu Tyr Lys Lys Asn Phe Gly Asn Ile Glu
            260                 265                 270
Pro Ala Ser Leu Ala Met Pro Glu Tyr Leu Lys Arg Tyr Tyr Asn Leu
        275                 280                 285
Ser Asp Glu Glu Leu Ser Gln Phe Ile Gly Lys Ala Ser Asn Phe Gly
    290                 295                 300
Gln Gln Glu Tyr Ser Asn Asn Gln Leu Ile Thr Pro Val Val Asn Ser
305                 310                 315                 320
Ser Asp Gly Thr Val Lys Val Tyr Arg Ile Thr Arg Glu Tyr Thr Thr
                325                 330                 335
Asn Ala Tyr Gln Met Asp Val Glu Leu Phe Pro Phe Gly Gly Glu Asn
            340                 345                 350
Tyr Arg Leu Asp Tyr Lys Phe Lys Asn Phe Tyr Asn Ala Ser Tyr Leu
        355                 360                 365
Ser Ile Lys Leu Asn Asp Lys Arg Glu Leu Val Arg Thr Glu Gly Ala
    370                 375                 380
Pro Gln Val Asn Ile Glu Tyr Ser Ala Asn Ile Thr Leu Asn Thr Ala
385                 390                 395                 400
Asp Ile Ser Gln Pro Phe Glu Ile Gly Leu Thr Arg Val Leu Pro Ser
                405                 410                 415
Gly Ser Trp Ala Tyr Ala Ala Lys Phe Thr Val Glu Tyr Asn
            420                 425                 430
Gln Tyr Ser Phe Leu Leu Lys Leu Asn Lys Ala Ile Arg Leu Ser Arg
        435                 440                 445
Ala Thr Glu Leu Ser Pro Thr Ile Leu Glu Gly Ile Val Arg Ser Val
    450                 455                 460
Asn Leu Gln Leu Asp Ile Asn Thr Asp Val Leu Gly Lys Val Phe Leu
465                 470                 475                 480
Thr Lys Tyr Tyr Met Gln Arg Tyr Ala Ile His Ala Glu Thr Ala Leu
                485                 490                 495
Ile Leu Cys Asn Ala Pro Ile Ser Gln Arg Ser Tyr Asp Asn Gln Pro
            500                 505                 510
Ser Gln Phe Asp Arg Leu Phe Asn Thr Pro Leu Leu Asn Gly Gln Tyr
        515                 520                 525
Phe Ser Thr Gly Asp Glu Glu Ile Asp Leu Asn Ser Gly Ser Thr Gly
    530                 535                 540
Asp Trp Arg Lys Thr Ile Leu Lys Arg Ala Phe Asn Ile Asp Val
545                 550                 555                 560
Ser Leu Phe Arg Leu Leu Lys Ile Thr Asp His Asp Asn Lys Asp Gly
                565                 570                 575
Lys Ile Lys Asn Asn Leu Lys Asn Leu Ser Asn Leu Tyr Ile Gly Lys
            580                 585                 590
```

```
        Leu Leu Ala Asp Ile His Gln Leu Thr Ile Asp Glu Leu Asp Leu Leu
                    595                 600                 605

Leu Ile Ala Val Gly Glu Gly Lys Thr Asn Leu Ser Ala Ile Ser Asp
                    610                 615                 620

Lys Gln Leu Ala Thr Leu Ile Arg Lys Leu Asn Thr Ile Thr Ser Trp
        625                 630                 635                 640

Leu His Thr Gln Lys Trp Ser Val Phe Gln Leu Phe Ile Met Thr Ser
                            645                 650                 655

Thr Ser Tyr Asn Lys Thr Leu Thr Pro Glu Ile Lys Asn Leu Leu Asp
                            660                 665                 670

Thr Val Tyr His Gly Leu Gln Gly Phe Asp Lys Asp Lys Ala Asp Leu
                            675                 680                 685

Leu His Val Met Ala Pro Tyr Ile Ala Ala Thr Leu Gln Leu Ser Ser
                            690                 695                 700

Glu Asn Val Ala His Ser Val Leu Leu Trp Ala Asp Lys Leu Gln Pro
        705                 710                 715                 720

Gly Asp Gly Ala Met Thr Ala Glu Lys Phe Trp Asp Trp Leu Asn Thr
                            725                 730                 735

Lys Tyr Thr Pro Gly Ser Ser Glu Ala Val Glu Thr Gln Glu His Ile
                            740                 745                 750

Val Gln Tyr Cys Gln Ala Leu Ala Gln Leu Glu Met Val Tyr His Ser
                            755                 760                 765

Thr Gly Ile Asn Glu Asn Ala Phe Arg Leu Phe Val Thr Lys Pro Glu
                            770                 775                 780

Met Phe Gly Ala Ala Thr Gly Ala Ala Pro Ala His Asp Ala Leu Ser
        785                 790                 795                 800

Leu Ile Met Leu Thr Arg Phe Ala Asp Trp Val Asn Ala Leu Gly Glu
                            805                 810                 815

Lys Ala Ser Ser Val Leu Ala Ala Phe Glu Ala Asn Ser Leu Thr Ala
                            820                 825                 830

Glu Gln Leu Ala Asp Ala Met Asn Leu Asp Ala Asn Leu Leu Leu Gln
                            835                 840                 845

Ala Ser Ile Gln Ala Gln Asn His Gln His Leu Pro Pro Val Thr Pro
                    850                 855                 860

Glu Asn Ala Phe Ser Cys Trp Thr Ser Ile Asn Thr Ile Leu Gln Trp
        865                 870                 875                 880

Val Asn Val Ala Gln Gln Leu Asn Val Ala Pro Gln Gly Val Ser Ala
                            885                 890                 895

Leu Val Gly Leu Asp Tyr Ile Gln Ser Met Lys Glu Thr Pro Thr Tyr
                            900                 905                 910

Ala Gln Trp Glu Asn Ala Ala Gly Val Leu Thr Ala Gly Leu Asn Ser
                            915                 920                 925

Gln Gln Ala Asn Thr Leu His Ala Phe Leu Asp Glu Ser Arg Ser Ala
                    930                 935                 940

Ala Leu Ser Thr Tyr Tyr Ile Arg Gln Val Ala Lys Ala Ala Ala Ala
        945                 950                 955                 960

Ile Lys Ser Arg Asp Asp Leu Tyr Gln Tyr Leu Leu Ile Asp Asn Gln
                            965                 970                 975

Val Ser Ala Ala Ile Lys Thr Thr Arg Ile Ala Glu Ala Ile Ala Ser
                    980                 985                 990

Ile Gln Leu Tyr Val Asn Arg Ala  Leu Glu Asn Val Glu  Glu Asn Ala
                    995                     1000                1005
```

```
Asn Ser Gly Val Ile Ser Arg Gln Phe Phe Ile Asp Trp Asp Lys
1010                1015                1020

Tyr Asn Lys Arg Tyr Ser Thr Trp Ala Gly Val Ser Gln Leu Val
1025                1030                1035

Tyr Tyr Pro Glu Asn Tyr Ile Asp Pro Thr Met Arg Ile Gly Gln
1040                1045                1050

Thr Lys Met Met Asp Ala Leu Leu Gln Ser Val Ser Gln Ser Gln
1055                1060                1065

Leu Asn Ala Asp Thr Val Glu Asp Ala Phe Met Ser Tyr Leu Thr
1070                1075                1080

Ser Phe Glu Gln Val Ala Asn Leu Lys Val Ile Ser Ala Tyr His
1085                1090                1095

Asp Asn Ile Asn Asn Asp Gln Gly Leu Thr Tyr Phe Ile Gly Leu
1100                1105                1110

Ser Glu Thr Asp Ala Gly Glu Tyr Tyr Trp Arg Ser Val Asp His
1115                1120                1125

Ser Lys Phe Asn Asp Gly Lys Phe Ala Ala Asn Ala Trp Ser Glu
1130                1135                1140

Trp His Lys Ile Asp Cys Pro Ile Asn Pro Tyr Lys Ser Thr Ile
1145                1150                1155

Arg Pro Val Ile Tyr Lys Ser Arg Leu Tyr Leu Leu Trp Leu Glu
1160                1165                1170

Gln Lys Glu Ile Thr Lys Gln Thr Gly Asn Ser Lys Asp Gly Tyr
1175                1180                1185

Gln Thr Glu Thr Asp Tyr Arg Tyr Glu Leu Lys Leu Ala His Ile
1190                1195                1200

Arg Tyr Asp Gly Thr Trp Asn Thr Pro Ile Thr Phe Asp Val Asn
1205                1210                1215

Lys Lys Ile Ser Glu Leu Lys Leu Glu Lys Asn Arg Ala Pro Gly
1220                1225                1230

Leu Tyr Cys Ala Gly Tyr Gln Gly Glu Asp Thr Leu Leu Val Met
1235                1240                1245

Phe Tyr Asn Gln Gln Asp Thr Leu Asp Ser Tyr Lys Asn Ala Ser
1250                1255                1260

Met Gln Gly Leu Tyr Ile Phe Ala Asp Met Ala Ser Lys Asp Met
1265                1270                1275

Thr Pro Glu Gln Ser Asn Val Tyr Arg Asp Asn Ser Tyr Gln Gln
1280                1285                1290

Phe Asp Thr Asn Asn Val Arg Arg Val Asn Asn Arg Tyr Ala Glu
1295                1300                1305

Asp Tyr Glu Ile Pro Ser Ser Val Ser Ser Arg Lys Asp Tyr Gly
1310                1315                1320

Trp Gly Asp Tyr Tyr Leu Ser Met Val Tyr Asn Gly Asp Ile Pro
1325                1330                1335

Thr Ile Asn Tyr Lys Ala Ala Ser Ser Asp Leu Lys Ile Tyr Ile
1340                1345                1350

Ser Pro Lys Leu Arg Ile Ile His Asn Gly Tyr Glu Gly Gln Lys
1355                1360                1365

Arg Asn Gln Cys Asn Leu Met Asn Lys Tyr Gly Lys Leu Gly Asp
1370                1375                1380

Lys Phe Ile Val Tyr Thr Ser Leu Gly Val Asn Pro Asn Asn Ser
1385                1390                1395
```

```
Ser Asn Lys Leu Met Phe Tyr Pro Val Gln Tyr Ser Gly Asn
1400                1405                1410

Thr Ser Gly Leu Asn Gln Gly Arg Leu Leu Phe His Arg Asp Thr
1415                1420                1425

Thr Tyr Pro Ser Lys Val Glu Ala Trp Ile Pro Gly Ala Lys Arg
1430                1435                1440

Ser Leu Thr Asn Gln Asn Ala Ala Ile Gly Asp Asp Tyr Ala Thr
1445                1450                1455

Asp Ser Leu Asn Lys Pro Asp Asp Leu Lys Gln Tyr Ile Phe Met
1460                1465                1470

Thr Asp Ser Lys Gly Thr Ala Thr Asp Val Ser Gly Pro Val Glu
1475                1480                1485

Ile Asn Thr Ala Ile Ser Pro Ala Lys Val Gln Ile Ile Val Lys
1490                1495                1500

Ala Gly Gly Lys Glu Gln Thr Phe Thr Ala Asp Lys Asp Val Ser
1505                1510                1515

Ile Gln Pro Ser Pro Ser Phe Asp Glu Met Asn Tyr Gln Phe Asn
1520                1525                1530

Ala Leu Glu Ile Asp Gly Ser Gly Leu Asn Phe Ile Asn Asn Ser
1535                1540                1545

Ala Ser Ile Asp Val Thr Phe Thr Ala Phe Ala Glu Asp Gly Arg
1550                1555                1560

Lys Leu Gly Tyr Glu Ser Phe Ser Ile Pro Val Thr Leu Lys Val
1565                1570                1575

Ser Thr Asp Asn Ala Leu Thr Leu His His Asn Glu Asn Gly Ala
1580                1585                1590

Gln Tyr Met Gln Trp Gln Ser Tyr Arg Thr Arg Leu Asn Thr Leu
1595                1600                1605

Phe Ala Arg Gln Leu Val Ala Arg Ala Thr Thr Gly Ile Asp Thr
1610                1615                1620

Ile Leu Ser Met Glu Thr Gln Asn Ile Gln Glu Pro Gln Leu Gly
1625                1630                1635

Lys Gly Phe Tyr Ala Thr Phe Val Ile Pro Pro Tyr Asn Leu Ser
1640                1645                1650

Thr His Gly Asp Glu Arg Trp Phe Lys Leu Tyr Ile Lys His Val
1655                1660                1665

Val Asp Asn Asn Ser His Ile Ile Tyr Ser Gly Gln Leu Thr Asp
1670                1675                1680

Thr Asn Ile Asn Ile Thr Leu Phe Ile Pro Leu Asp Asp Val Pro
1685                1690                1695

Leu Asn Gln Asp Tyr His Ala Lys Val Tyr Met Thr Phe Lys Lys
1700                1705                1710

Ser Pro Ser Asp Gly Thr Trp Trp Gly Pro His Phe Val Arg Asp
1715                1720                1725

Asp Lys Gly Ile Val Thr Ile Asn Pro Lys Ser Ile Leu Thr His
1730                1735                1740

Phe Glu Ser Val Asn Val Leu Asn Asn Ile Ser Ser Glu Pro Met
1745                1750                1755

Asp Phe Ser Gly Ala Asn Ser Leu Tyr Phe Trp Glu Leu Phe Tyr
1760                1765                1770

Tyr Thr Pro Met Leu Val Ala Gln Arg Leu Leu His Glu Gln Asn
1775                1780                1785
```

-continued

```
Phe Asp Glu Ala Asn Arg Trp Leu Lys Tyr Val Trp Ser Pro Ser
1790                1795                1800

Gly Tyr Ile Val His Gly Gln Ile Gln Asn Tyr Gln Trp Asn Val
1805                1810                1815

Arg Pro Leu Leu Glu Asp Thr Ser Trp Asn Ser Asp Pro Leu Asp
1820                1825                1830

Ser Val Asp Pro Asp Ala Val Ala Gln His Asp Pro Met His Tyr
1835                1840                1845

Lys Val Ser Thr Phe Met Arg Thr Leu Asp Leu Leu Ile Ala Arg
1850                1855                1860

Gly Asp His Ala Tyr Arg Gln Leu Glu Arg Asp Thr Leu Asn Glu
1865                1870                1875

Ala Lys Met Trp Tyr Met Gln Ala Leu His Leu Leu Gly Asp Lys
1880                1885                1890

Pro Tyr Leu Pro Leu Ser Thr Thr Trp Ser Asp Pro Arg Leu Asp
1895                1900                1905

Arg Ala Ala Asp Ile Thr Thr Gln Asn Ala His Asp Ser Ala Ile
1910                1915                1920

Val Ala Leu Arg Gln Asn Ile Pro Thr Pro Ala Pro Leu Ser Leu
1925                1930                1935

Arg Ser Ala Asn Thr Leu Thr Asp Leu Phe Leu Pro Gln Ile Asn
1940                1945                1950

Glu Val Met Met Asn Tyr Trp Gln Thr Leu Ala Gln Arg Val Tyr
1955                1960                1965

Asn Leu Arg His Asn Leu Ser Ile Asp Gly Gln Pro Leu Tyr Leu
1970                1975                1980

Pro Ile Tyr Ala Thr Pro Ala Asp Pro Lys Ala Leu Leu Ser Ala
1985                1990                1995

Ala Val Ala Thr Ser Gln Gly Gly Gly Lys Leu Pro Glu Ser Phe
2000                2005                2010

Met Ser Leu Trp Arg Phe Pro His Met Leu Glu Asn Ala Arg Gly
2015                2020                2025

Met Val Ser Gln Leu Thr Gln Phe Gly Ser Thr Leu Gln Asn Ile
2030                2035                2040

Ile Glu Arg Gln Asp Ala Glu Ala Leu Asn Ala Leu Leu Gln Asn
2045                2050                2055

Gln Ala Ala Glu Leu Ile Leu Thr Asn Leu Ser Ile Gln Asp Lys
2060                2065                2070

Thr Ile Glu Glu Leu Asp Ala Glu Lys Thr Val Leu Glu Lys Ser
2075                2080                2085

Lys Ala Gly Ala Gln Ser Arg Phe Asp Ser Tyr Gly Lys Leu Tyr
2090                2095                2100

Asp Glu Asn Ile Asn Ala Gly Glu Asn Gln Ala Met Thr Leu Arg
2105                2110                2115

Ala Ser Ala Ala Gly Leu Thr Thr Ala Val Gln Ala Ser Arg Leu
2120                2125                2130

Ala Gly Ala Ala Ala Asp Leu Val Pro Asn Ile Phe Gly Phe Ala
2135                2140                2145

Gly Gly Gly Ser Arg Trp Gly Ala Ile Ala Glu Ala Thr Gly Tyr
2150                2155                2160

Val Met Glu Phe Ser Ala Asn Val Met Asn Thr Glu Ala Asp Lys
2165                2170                2175
```

| | | | | | | | | | | | |
|---|---|---|---|---|---|---|---|---|---|---|---|
|Ile|Ser|Gln|Ser|Glu|Thr|Tyr|Arg|Arg|Arg|Gln|Glu|Trp|Glu|
|2180| | | |2185| | | |2190| | | |
|Ile|Gln|Arg|Asn|Asn|Ala|Glu|Ala|Leu|Lys|Gln|Ile|Asp|Ala|
|2195| | | |2200| | | |2205| | | |
|Gln|Leu|Lys|Ser|Leu|Ala|Val|Arg|Arg|Glu|Ala|Ala|Val|Leu|Gln|
|2210| | | |2215| | | |2220| | | |
|Lys|Thr|Ser|Leu|Lys|Thr|Gln|Gln|Glu|Gln|Thr|Gln|Ser|Gln|Leu|
|2225| | | |2230| | | |2235| | | |
|Ala|Phe|Leu|Gln|Arg|Lys|Phe|Ser|Asn|Gln|Ala|Leu|Tyr|Asn|Trp|
|2240| | | |2245| | | |2250| | | |
|Leu|Arg|Gly|Arg|Leu|Ala|Ala|Ile|Tyr|Phe|Gln|Phe|Tyr|Asp|Leu|
|2255| | | |2260| | | |2265| | | |
|Ala|Val|Ala|Arg|Cys|Leu|Met|Ala|Glu|Gln|Ala|Tyr|Arg|Trp|Glu|
|2270| | | |2275| | | |2280| | | |
|Leu|Asn|Asp|Asp|Ser|Ala|Arg|Phe|Ile|Lys|Pro|Gly|Ala|Trp|Gln|
|2285| | | |2290| | | |2295| | | |
|Gly|Thr|Tyr|Ala|Gly|Leu|Leu|Ala|Gly|Glu|Thr|Leu|Met|Leu|Ser|
|2300| | | |2305| | | |2310| | | |
|Leu|Ala|Gln|Met|Glu|Asp|Ala|His|Leu|Lys|Arg|Asp|Lys|Arg|Ala|
|2315| | | |2320| | | |2325| | | |
|Leu|Glu|Val|Glu|Arg|Thr|Val|Ser|Leu|Ala|Glu|Val|Tyr|Ala|Gly|
|2330| | | |2335| | | |2340| | | |
|Leu|Pro|Lys|Asp|Asn|Gly|Pro|Phe|Ser|Leu|Ala|Gln|Glu|Ile|Asp|
|2345| | | |2350| | | |2355| | | |
|Lys|Leu|Val|Ser|Gln|Gly|Ser|Gly|Ser|Ala|Gly|Ser|Gly|Asn|Asn|
|2360| | | |2365| | | |2370| | | |
|Asn|Leu|Ala|Phe|Gly|Ala|Gly|Thr|Asp|Thr|Lys|Thr|Ser|Leu|Gln|
|2375| | | |2380| | | |2385| | | |
|Ala|Ser|Val|Ser|Phe|Ala|Asp|Leu|Lys|Ile|Arg|Glu|Asp|Tyr|Pro|
|2390| | | |2395| | | |2400| | | |
|Ala|Ser|Leu|Gly|Lys|Ile|Arg|Arg|Ile|Lys|Gln|Ile|Ser|Val|Thr|
|2405| | | |2410| | | |2415| | | |
|Leu|Pro|Ala|Leu|Leu|Gly|Pro|Tyr|Gln|Asp|Val|Gln|Ala|Ile|Leu|
|2420| | | |2425| | | |2430| | | |
|Ser|Tyr|Gly|Asp|Lys|Ala|Gly|Leu|Ala|Asn|Gly|Cys|Glu|Ala|Leu|
|2435| | | |2440| | | |2445| | | |
|Ala|Val|Ser|His|Gly|Met|Asn|Asp|Ser|Gly|Gln|Phe|Gln|Leu|Asp|
|2450| | | |2455| | | |2460| | | |
|Phe|Asn|Asp|Gly|Lys|Phe|Leu|Pro|Phe|Glu|Gly|Ile|Ala|Ile|Asp|
|2465| | | |2470| | | |2475| | | |
|Gln|Gly|Thr|Leu|Thr|Leu|Ser|Phe|Pro|Asn|Ala|Ser|Met|Pro|Glu|
|2480| | | |2485| | | |2490| | | |
|Lys|Gly|Lys|Gln|Ala|Thr|Met|Leu|Lys|Thr|Leu|Asn|Asp|Ile|Ile|
|2495| | | |2500| | | |2505| | | |
|Leu|His|Ile|Arg|Tyr|Thr|Ile|Lys|
|2510| | | |2515| | | |

<210> SEQ ID NO 5
<211> LENGTH: 7560
<212> TYPE: DNA
<213> ORGANISM: Photorabdus luminescens

<400> SEQUENCE: 5
ccatggctaa cgagtccgtc aaggagatcc cagacgtcct caagtcccaa tgcggtttca    60

```
actgcctcac tgacatctcc cacagctcct tcaacgagtt cagacaacaa gtctctgagc    120
acctctcctg gtccgagacc catgacctct accatgacgc tcagcaagct cagaaggaca    180
acaggctcta cgaggctagg atcctcaaga gggctaaccc acaactccag aacgctgtcc    240
acctcgccat cttggctcca aacgctgagt tgattggtta caacaaccag ttctctggca    300
gagctagcca gtacgtggct cctggtacag tctcctccat gttcagccca gccgcttacc    360
tcactgagtt gtaccgcgag gctaggaacc ttcatgcttc tgactccgtc tactacttgg    420
acacacgcag accagacctc aagagcatgg ccctcagcca acagaacatg gacattgagt    480
tgtccaccct ctccttgagc aacgagcttc tcttggagtc catcaagact gagagcaagt    540
tggagaacta caccaaggtc atggagatgc tctccacctt cagaccaagc ggtgcaactc    600
cataccatga tgcctacgag aacgtcaggg aggtcatcca acttcaagac cctggtcttg    660
agcaactcaa cgcttctcca gccattgctg gtttgatgca ccaggcatcc ttgctcggta    720
tcaacgcctc catctctcct gagttgttca acatcttgac tgaggagatc actgagggca    780
acgctgagga gttgtacaag aagaacttcg gcaacattga gccagcctct cttgcaatgc    840
ctgagtacct caagaggtac tacaacttgt ctgatgagga gctttctcaa ttcattggca    900
aggcttccaa cttcggtcaa caggagtaca gcaacaacca gctcatcact ccagttgtga    960
actcctctga tggcactgtg aaggtctacc gcatcacacg tgagtacacc acaaacgcct   1020
accaaatgga tgttgagttg ttcccattcg gtggtgagaa ctacagactt gactacaagt   1080
tcaagaactt ctacaacgcc tcctaccttc ccatcaagtt gaacgacaag agggagcttg   1140
tcaggactga gggtgctcct caagtgaaca ttgagtactc tgccaacatc accctcaaca   1200
cagctgacat ctctcaacca ttcgagattg gtttgaccag agtccttccc tctggctcct   1260
gggcctacgc tgcagccaag ttcactgttg aggagtacaa ccagtactct ttcctcttga   1320
agctcaacaa ggcaattcgt ctcagcagag ccactgagtt gtctcccacc atcttggagg   1380
gcattgtgag gtctgtcaac cttcaacttg acatcaacac tgatgtgctt ggcaaggtct   1440
tcctcaccaa gtactacatg caacgctacg ccatccatgc tgagactgca ctcatcctct   1500
gcaacgcacc catctctcaa cgctcctacg acaaccagcc ttcccagttc gacaggctct   1560
tcaacactcc tctcttgaac ggccagtact ctccactgg tgatgaggag attgacctca   1620
actctggctc cacaggtgac tggagaaaga ccatcttgaa gagggccttc aacattgatg   1680
atgtctctct cttccgtctc ttgaagatca cagatcacga caacaaggat ggcaagatca   1740
agaacaactt gaagaacctt tccaacctct acattggcaa gttgcttgca gacatccacc   1800
aactcaccat tgatgagttg gacctcttgc tcattgcagt cggtgagggc aagaccaacc   1860
tctctgcaat ctctgacaag cagttggcaa ccctcatcag gaagttgaac accatcacct   1920
cctggcttca cacccagaag tggtctgtct tccaactctt catcatgacc agcacctcct   1980
acaacaagac cctcactcct gagatcaaga acctcttgga cacagtctac cacggtctcc   2040
aaggcttcga caaggacaag gctgacttgc ttcatgtcat ggctccctac attgcagcca   2100
ccctccaact ctcctctgag aacgtggctc actctgtctt gctctgggct gacaagctcc   2160
aacctggtga tggtgccatg actgctgaga gttctgggga ctggctcaac accaagtaca   2220
caccaggctc ctctgaggct gttgagactc aaagagcacat tgtgcaatac tgccaggctc   2280
ttgcacagtt ggagatggtc taccactcca ctggcatcaa cgagaacgct ttcagactct   2340
tcgtcaccaa gctgagatg ttcggtgctc ccacaggtgc tgcacctgct catgatgctc   2400
tctccctcat catgttgacc aggttcgctg actgggtcaa cgctcttggt gagaaggctt   2460
```

```
cctctgtctt ggctgccttc gaggccaact ccctcactgc tgagcaactt gctgatgcca    2520
tgaaccttga tgccaacctc ttgctccaag cttccattca agctcagaac caccaacacc    2580
tcccacctgt cactccagag aacgctttct cctgctggac ctccatcaac accatcctcc    2640
aatgggtcaa cgtggctcag caactcaacg tggctccaca aggtgtctct gctttggtcg    2700
gtcttgacta catccagtcc atgaaggaga caccaaccta cgctcaatgg gagaacgcag    2760
ctggtgtctt gactgctggt ctcaactccc aacaggccaa caccctccat gctttcttgg    2820
atgagtctcg ctctgctgcc ctctccacct actacatcag gcaagtcgcc aaggcagctg    2880
ctgccatcaa gtctcgcgat gacctctacc aatacctcct cattgacaac caggtctctg    2940
ctgccatcaa gaccaccagg atcgctgagg ccatcgcttc catccaactc tacgtcaacc    3000
gcgctcttga gaacgttgag gagaacgcca actctggtgt catctctcgc caattcttca    3060
tcgactggga caagtacaac aagaggtact ccacctgggc tggtgtctct caacttgtct    3120
actacccaga gaactacatt gacccaacca tgaggattgg tcagaccaag atgatggatg    3180
ctctcttgca atctgtctcc caaagccaac tcaacgctga cactgtggag gatgccttca    3240
tgagctacct cacctccttc gagcaagttg ccaacctcaa ggtcatctct gcttaccatg    3300
acaacatcaa caacgaccaa ggtctcacct acttcattgg tctctctgag actgatgctg    3360
gtgagtacta ctggagatcc gtggaccaca gcaagttcaa cgatggcaag ttcgctgcaa    3420
acgcttggtc tgagtggcac aagattgact gccctatcaa cccatacaag tccaccatca    3480
gacctgtcat ctacaagagc cgcctctact tgctctggct tgagcagaag gagatcacca    3540
agcaaactgg caactccaag gatggttacc aaactgagac tgactaccgc tacgagttga    3600
agttggctca catccgctac gatggtacct ggaacactcc aatcaccttc gatgtcaaca    3660
agaagatcag cgagttgaag ttggagaaga accgtgctcc tggtctctac tgcgctggtt    3720
accaaggtga ggacaccctc ttggtcatgt tctacaacca gcaagacacc cttgactcct    3780
acaagaacgc ttccatgcaa ggtctctaca tcttcgctga catggcttcc aaggacatga    3840
ctccagagca aagcaacgtc taccgtgaca actcctacca acagttcgac accaacaacg    3900
tcaggcgtgt caacaacaga tacgctgagg actacgagat cccaagctct gtcagctctc    3960
gcaaggacta cggctggggt gactactacc tcagcatggt gtacaacggt gacatcccaa    4020
ccatcaacta caaggctgcc tcttccgacc tcaaaatcta catcagccca agctcagga    4080 tcatccacaa cggctacgag ggtcagaaga ggaaccagtg caacttgatg aacaagtacg    4140
gcaagttggg tgacaagttc attgtctaca cctctcttgg tgtcaaccca acaacagct    4200 ccaacaagct catgttctac ccagtctacc aatactctgg caacacctct ggtctcaacc    4260
agggtagact cttgttccac agggacacca cctacccaag caaggtggag gcttggattc    4320
ctggtgccaa gaggtccctc accaaccaga cgctgccat tggtgatgac tacgccacag    4380
actccctcaa caagcctgat gacctcaagc agtacatctt catgactgac tccaagggca    4440
cagccactga tgtctctggt ccagtggaga tcaacactgc aatcagccca gccaaggtcc    4500
aaatcattgt caaggctggt ggcaaggagc aaaccttcac agctgacaag gatgtctcca    4560
tccagccaag cccatccttc gatgagatga actaccaatt caacgctctt gagattgatg    4620
gttctggcct caacttcatc aacaactctg cttccattga tgtcaccttc actgccttcg    4680
ctgaggatgg ccgcaagttg ggttacgaga gcttctccat cccagtcacc cttaaggttt    4740
ccactgacaa cgcactcacc cttcatcaca acgagaacgg tgctcagtac atgcaatggc    4800
aaagctaccg caccaggttg aacaccctct tcgcaaggca acttgtggcc cgtgccacca    4860
```

```
caggcattga caccatcctc agcatggaga cccagaacat ccaagagcca cagttgggca    4920
agggtttcta cgccaccttc gtcatcccac cttacaacct cagcactcat ggtgatgaga    4980
ggtggttcaa gctctacatc aagcacgtgg ttgacaacaa ctcccacatc atctactctg    5040
gtcaactcac tgacaccaac atcaacatca ccctcttcat cccacttgac gatgtcccac    5100
tcaaccagga ctaccatgcc aaggtctaca tgaccttcaa gaagtctcca tctgatggca    5160
cctggtgggg tccacacttc gtccgtgatg acaagggcat cgtcaccatc aacccaaagt    5220
ccatcctcac ccacttcgag tctgtcaacg ttctcaacaa catctcctct gagccaatgg    5280
acttctctgg tgccaactcc ctctacttct gggagttgtt ctactacaca ccaatgcttg    5340
tggctcaaag gttgctccat gagcagaact tcgatgaggc caacaggtgg ctcaagtacg    5400
tctggagccc atctggttac attgtgcatg gtcaaatcca gaactaccaa tggaacgtca    5460
ggccattgct tgaggacacc tcctggaact ctgacccact tgactctgtg accctgatg    5520 ctgtggctca acatgaccca atgcactaca aggtctccac cttcatgagg accttggacc    5580
tcttgattgc cagaggtgac catgcttacc gccaattgga gagggacacc ctcaacgagg    5640
caaagatgtg gtacatgcaa gctctccacc tcttgggtga caagccatac ctcccactca    5700
gcaccacttg gtccgaccca aggttggacc gtgctgctga catcaccact cagaacgctc    5760
atgactctgc cattgttgct ctcaggcaga acatcccaac tcctgctcca ctctccctca    5820
gatctgctaa caccctcact gacttgttcc tcccacagat caacgaggtc atgatgaact    5880
actggcaaac cttggctcaa agggtctaca acctcagaca caacctctcc attgatggtc    5940
aaccactcta cctcccaatc tacgccacac cagctgaccc aaaggctctt ctctctgctg    6000
ctgtggctac cagccaaggt ggtggcaagc tcccagagtc cttcatgtcc ctctggaggt    6060
tcccacacat gttggagaac gcccgtggca tggtctccca actcacccag ttcggttcca    6120
ccctccagaa catcattgag aggcaagatg ctgaggctct caacgctttg ctccagaacc    6180
aggcagctga gttgatcctc accaacttgt ccatccaaga caagaccatt gaggagcttg    6240
atgctgagaa gacagtcctt gagaagagca aggctggtgc ccaatctcgc ttcgactcct    6300
acggcaagct ctacgatgag aacatcaacg ctggtgagaa ccaggccatg accctcaggg    6360
cttccgcagc tggtctcacc actgctgtcc aagcctctcg cttggctggt gcagctgctg    6420
acctcgttcc aaacatcttc ggtttcgctg gtggtggctc cagatggggt gccattgctg    6480
aggctaccgg ttacgtcatg gagttctctg ccaacgtcat gaacactgag gctgacaaga    6540
tcagccaatc tgagacctac agaaggcgcc gtcaagagtg ggagatccaa aggaacaacg    6600
ctgaggcaga gttgaagcaa atcgatgctc aactcaagtc cttggctgtc agaagggagg    6660
ctgctgtcct ccagaagacc tccctcaaga cccaacagga gcaaacccag tcccagttgg    6720 cttttcctcca aggaagttc tccaaccagg ctctctacaa ctggctcaga ggccgcttgg    6780
ctgccatcta cttccaattc tacgaccttg ctgtggccag gtgcctcatg gctgagcaag    6840
cctaccgctg ggagttgaac gatgactccg ccaggttcat caagccaggt gcttggcaag    6900
gcacctacgc tggtctcctt gctggtgaga ccctcatgct ctccttggct caaatggagg    6960
atgctcacct caagagggac aagagggctt tggaggtgga ggacagtc tcccttgctg    7020 aggtctacgc tggtctccca aaggacaacg gtccattctc ccttgctcaa gagattgaca    7080
agttggtcag ccaaggttct ggttctgctg gttctggtaa caacaacttg gctttcggcg    7140
ctggtactga caccaagacc tccctccaag cctctgtctc cttcgctgac ctcaagatca    7200
gggaggacta cccagcttcc cttggcaaga tcaggcgcat caagcaaatc tctgtcaccc    7260
```

```
tcccagctct cttgggtcca taccaagatg tccaagcaat cctctcctac ggtgacaagg   7320
ctggtttggc gaacggttgc gaggctcttg ctgtctctca tggcatgaac gactctggtc   7380
aattccaact tgacttcaac gatggcaagt tcctcccatt cgagggcatt gccattgacc   7440
aaggcaccct caccctctcc ttcccaaacg cttccatgcc agagaaggga aagcaagcca   7500
ccatgctcaa gaccctcaac gatatcatcc tccacatcag gtacaccatc aagtgagctc   7560
```

<210> SEQ ID NO 6
<211> LENGTH: 7302
<212> TYPE: DNA
<213> ORGANISM: Photorabdus luminescens

<400> SEQUENCE: 6

```
ccatggctga gttgattggt tacaacaacc agttctctgg cagagctagc cagtacgtgg     60
ctcctggtac agtctcctcc atgttcagcc agccgctta cctcactgag ttgtaccgcg    120
aggctaggaa ccttcatgct tctgactccg tctactactt ggacacacgc agaccagacc    180
tcaagagcat ggccctcagc aacagaacaa tggacattga gttgtccacc ctctccttga    240
gcaacgagct tctcttggag tccatcaaga ctgagagcaa gttggagaac tacaccaagg    300
tcatggagat gctctccacc ttcagaccaa gcggtgcaac tccataccat gatgcctacg    360
agaacgtcag ggaggtcatc caacttcaag accctggtct tgagcaactc aacgcttctc    420
cagccattgc tggtttgatg caccaggcat ccttgctcgg tatcaacgcc tccatctctc    480
ctgagttgtt caacatcttg actgaggaga tcactgaggg caacgctgag gagttgtaca    540
agaagaactt cggcaacatt gagccagcct ctcttgcaat gcctgagtac ctcaagaggt    600
actacaactt gtctgatgag gagctttctc aattcattgg caaggcttcc aacttcggtc    660
aacaggagta cagcaacaac cagctcatca ctccagttgt gaactcctct gatggcactg    720
tgaaggtcta ccgcatcaca cgtgagtaca ccacaaacgc ctaccaaatg gatgttgagt    780
tgttcccatt cggtggtgag aactacagac ttgactacaa gttcaagaac ttctacaacg    840
cctcctacct ctccatcaag ttgaacgaca gagggagct tgtcaggact gagggtgctc    900
ctcaagtgaa cattgagtac tctgccaaca tcaccctcaa cacagctgac atctctcaac    960
cattcgagat tggtttgacc agagtccttc cctctggctc ctgggcctac gctgcagcca   1020
agttcactgt tgaggagtac aaccagtact ctttcctctt gaagctcaac aaggcaattc   1080
gtctcagcag agccactgag ttgtctccca ccatcttgga gggcattgtg aggtctgtca   1140
accttcaact tgacatcaac actgatgtgc ttggcaaggt cttcctcacc aagtactaca   1200
tgcaacgcta cgccatccat gctgagactg cactcatcct ctgcaacgca cccatctctc   1260
aacgctccta cgacaaccag ccttcccagt tcgacaggct cttcaacact cctctcttga   1320
acggccagta cttctccact ggtgatgagg agattgacct caactctggc tccacaggtg   1380
actggagaaa gaccatcttg aagagggcct tcaacattga tgatgtctct ctcttccgtc   1440
tcttgaagat cacagatcac gacaacaagg atggcaagat caagaacaac ttgaagaacc   1500
tttccaacct ctacattggc aagttgcttg cagacatcca ccaactcacc attgatgagt   1560
tggacctctt gctcattgca gtcggtgagg gcaagaccaa cctctctgca atctctgaca   1620
agcagttggc aaccctcatc aggaagttga acaccatcac ctcctggctt cacacccaga   1680
agtggtctgt cttccaactc ttcatcatga ccagcacctc ctacaacaag accctcactc   1740
ctgagatcaa gaacctcttg gacacagtct accacggtct ccaaggcttc gacaaggaca   1800
aggctgactt gcttcatgtc atggctccct acattgcagc caccctccaa ctctcctctg   1860
```

-continued

```
agaacgtggc tcactctgtc ttgctctggg ctgacaagct ccaacctggt gatggtgcca    1920
tgactgctga gaagttctgg gactggctca acaccaagta cacaccaggc tcctctgagg    1980
ctgttgagac tcaagagcac attgtgcaat actgccaggc tcttgcacag ttggagatgg    2040
tctaccactc cactggcatc aacgagaacg ctttcagact cttcgtcacc aagcctgaga    2100
tgttcggtgc tgccacaggt gctgcacctg ctcatgatgc tctctccctc atcatgttga    2160
ccaggttcgc tgactgggtc aacgctcttg gtgagaaggc ttcctctgtc ttggctgcct    2220
tcgaggccaa ctccctcact gctgagcaac ttgctgatgc catgaacctt gatgccaacc    2280
tcttgctcca agcttccatt caagctcaga accaccaaca cctcccacct gtcactccag    2340
agaacgcttt ctcctgctgg acctccatca acaccatcct ccaatgggtc aacgtggctc    2400
agcaactcaa cgtggctcca caaggtgtct ctgctttggt cggtcttgac tacatccagt    2460
ccatgaagga cacaccaacc tacgctcaat gggagaacgc agctggtgtc ttgactgctg    2520
gtctcaactc ccaacaggcc aacaccctcc atgctttctt ggatgagtct cgctctgctg    2580
ccctctccac ctactacatc aggcaagtcg ccaaggcagc tgctgccatc aagtctcgcg    2640
atgacctcta ccaatacctc ctcattgaca accaggtctc tgctgccatc aagaccacca    2700
ggatcgctga ggccatcgct tccatccaac tctacgtcaa ccgcgctctt gagaacgttg    2760 aggaaacgc caactctggt gtcatctctc gccaattctt catcgactgg acaagtaca    2820 acaagaggta ctccacctgg gctggtgtct ctcaacttgt ctactaccca gagaactaca    2880
ttgacccaac catgaggatt ggtcagacca agatgatgga tgctctcttg caatctgtct    2940
cccaaagcca actcaacgct gacactgtgg aggatgcctt catgagctac ctcacctcct    3000
tcgagcaagt tgccaacctc aaggtcatct ctgcttacca tgacaacatc aacaacgacc    3060
aaggtctcac ctacttcatt ggtctctctg agactgatgc tggtgagtac tactggagat    3120
ccgtggacca cagcaagttc aacgatggca agttcgctgc aaacgcttgg tctgagtggc    3180
acaagattga ctgccctatc aacccataca agtccaccat cagacctgtc atctacaaga    3240
gccgcctcta cttgctctgg cttgagcaga aggagatcac caagcaaact ggcaactcca    3300
aggatggtta ccaaactgag actgactacc gctacgagtt gaagttggct cacatccgct    3360
acgatggtac ctggaacact ccaatcacct tcgatgtcaa caagaagatc agcgagttga    3420
agttggagaa gaaccgtgct cctggtctct actgcgctgg ttaccaaggt gaggacaccc    3480
tcttggtcat gttctacaac cagcaagaca cccttgactc ctacaagaac gcttccatgc    3540
aaggtctcta catcttcgct gacatggctt ccaaggacat gactccagag caaagcaacg    3600
tctaccgtga caactcctac aacagttcg acaccaacaa cgtcaggcgt gtcaacaaca    3660
gatacgctga ggactacgag atcccaagct ctgtcagctc tcgcaaggac tacggctggg    3720
gtgactacta cctcagcatg gtgtacaacg gtgacatccc aaccatcaac tacaaggctg    3780
cctcttccga cctcaaaatc tacatcagcc caaagctcag gatcatccac aacggctacg    3840
agggtcagaa gaggaaccag tgcaacttga tgaacaagta cggcaagttg ggtgacaagt    3900
tcattgtcta cacctctctt ggtgtcaacc caaacaacag ctccaacaag ctcatgttct    3960
acccagtcta ccaatactct ggcaacacct ctggtctcaa ccagggtaga ctcttgttcc    4020
acagggacac cacctaccca agcaaggtgg aggcttggat tcctggtgcc aagaggtccc    4080
tcaccaacca gaacgctgcc attggtgatg actacgccac agactccctc aacaagcctg    4140
atgacctcaa gcagtacatc ttcatgactg actccaaggg cacagccact gatgtctctg    4200
gtccagtgga gatcaacact gcaatcagcc cagccaaggt ccaaatcatt gtcaaggctg    4260
```

```
gtggcaagga gcaaaccttc acagctgaca aggatgtctc catccagcca agcccatcct    4320
tcgatgagat gaactaccaa ttcaacgctc ttgagattga tggttctggc ctcaacttca    4380
tcaacaactc tgcttccatt gatgtcacct tcactgcctt cgctgaggat ggccgcaagt    4440
tgggttacga gagcttctcc atcccagtca cccttaaggt ttccactgac aacgcactca    4500
cccttcatca aacgagaac ggtgctcagt acatgcaatg gcaaagctac cgcaccaggt    4560
tgaacaccct cttcgcaagg caacttgtgg cccgtgccac cacaggcatt gacaccatcc    4620
tcagcatgga gacccagaac atccaagagc acagttggg caagggtttc tacgccacct    4680
tcgtcatccc accttacaac ctcagcactc atggtgatga gaggtggttc aagctctaca    4740
tcaagcacgt ggttgacaac aactcccaca tcatctactc tggtcaactc actgacacca    4800
acatcaacat caccctcttc atcccacttg acgatgtccc actcaaccag gactaccatg    4860
ccaaggtcta catgaccttc aagaagtctc catctgatgg cacctggtgg ggtccacact    4920
tcgtccgtga tgacaagggc atcgtcacca tcaacccaaa gtccatcctc acccacttcg    4980
agtctgtcaa cgttctcaac aacatctcct ctgagccaat ggacttctct ggtgccaact    5040
ccctctactt ctgggagttg ttctactaca caccaatgct tgtggctcaa aggttgctcc    5100
atgagcagaa cttcgatgag gccaacaggt ggctcaagta cgtctggagc ccatctggtt    5160
acattgtgca tggtcaaatc cagaactacc aatggaacgt caggccattg cttgaggaca    5220
cctcctggaa ctctgaccca cttgactctg tggaccctga tgctgtggct caacatgacc    5280
caatgcacta caaggtctcc accttcatga ggaccttgga cctcttgatt gccagaggtg    5340
accatgctta ccgccaattg gagagggaca ccctcaacga ggcaaagatg tggtacatgc    5400
aagctctcca cctcttgggt gacaagccat acctcccact cagcaccact tggtccgacc    5460
caaggttgga ccgtgctgct gacatcacca ctcagaacgc tcatgactct gccattgttg    5520
ctctcaggca gaacatccca actcctgctc cactctccct cagatctgct aacaccctca    5580
ctgacttgtt cctcccacag atcaacgagg tcatgatgaa ctactggcaa accttggctc    5640
aaagggtcta caacctcaga cacaacctct ccattgatgg tcaaccactc tacctcccaa    5700
tctacgccac accagctgac ccaaaggctc ttctctctgc tgctgtggct accagccaag    5760
gtggtggcaa gctcccagag tccttcatgt ccctctggag gttcccacac atgttggaga    5820
acgcccgtgg catggtctcc caactcaccc agttcggttc caccctccag aacatcattg    5880
agaggcaaga tgctgaggct ctcaacgctt tgctccagaa ccaggcagct gagttgatcc    5940
tcaccaactt gtccatccaa gacaagacca ttgaggagct tgatgctgag aagacagtcc    6000
ttgagaagag caaggctggt gcccaatctc gcttcgactc ctacggcaag ctctacgatg    6060
agaacatcaa cgctggtgag aaccaggcca tgacctcag ggcttccgca gctggtctca    6120
ccactgctgt ccaagcctct cgcttggctg gtgcagctgc tgacctcgtt ccaaacatct    6180
tcggtttcgc tggtggtggc tccagatggg gtgccattgc tgaggctacc ggttacgtca    6240
tggagttctc tgccaacgtc atgaacactg aggctgacaa gatcagccaa tctgagacct    6300
acagaaggcg ccgtcaagag tgggagatcc aaaggaacaa cgctgaggca gagttgaagc    6360
aaatcgatgc tcaactcaag tccttggctg tcagaaggga ggctgctgtc ctccagaaga    6420 cctcctcaa gacccaacag gagcaaaccc agtcccagtt ggctttcctc caaaggaagt    6480
tctccaacca ggctctctac aactggctca gaggccgctt ggctgccatc tacttccaat    6540
tctacgacct tgctgtggcc aggtgcctca tggctgagca agcctaccgc tgggagttga    6600
acgatgactc cgccaggttc atcaagccag gtgcttggca aggcacctac gctggtctcc    6660
```

```
ttgctggtga gaccctcatg ctctccttgg ctcaaatgga ggatgctcac ctcaagaggg   6720
acaagagggc tttggaggtg gagaggacag tctcccttgc tgaggtctac gctggtctcc   6780
caaaggacaa cggtccattc tcccttgctc aagagattga caagttggtc agccaaggtt   6840
ctggttctgc tggttctggt aacaacaact tggctttcgg cgctggtact gacaccaaga   6900
cctccctcca agcctctgtc tccttcgctg acctcaagat cagggaggac tacccagctt   6960
cccttggcaa gatcaggcgc atcaagcaaa tctctgtcac cctcccagct ctcttgggtc   7020
cataccaaga tgtccaagca atcctctcct acggtgacaa ggctggtttg gcgaacggtt   7080
gcgaggctct tgctgtctct catggcatga acgactctgg tcaattccaa cttgacttca   7140
acgatggcaa gttcctccca ttcgagggca ttgccattga ccaaggcacc ctcaccctct   7200
ccttcccaaa cgcttccatg ccagagaagg gaaagcaagc caccatgctc aagaccctca   7260
acgatatcat cctccacatc aggtacacca tcaagtgagc tc                       7302

<210> SEQ ID NO 7
<211> LENGTH: 5561
<212> TYPE: DNA
<213> ORGANISM: Photorabdus luminescens

<400> SEQUENCE: 7
ccatggctaa cgagtccgtc aaggagatcc cagacgtcct caagtcccaa tgcggtttca     60
actgcctcac tgacatctcc cacagctcct tcaacgagtt cagacaacaa gtctctgagc    120
acctctcctg gtccgagacc catgacctct ccatgacgc tcagcaagct cagaaggaca     180
acaggctcta cgaggctagg atcctcaaga gggctaaccc acaactccag aacgctgtcc    240
acctcgccat cttggctcca aacgctgagt tgattggtta caacaaccag ttctctggca    300
gagctagcca gtacgtggct cctggtacag tctcctccat gttcagccca gccgcttacc    360
tcactgagtt gtaccgcgag gctaggaacc ttcatgcttc tgactccgtc tactacttgg    420
acacacgcag accagacctc aagagcatgg ccctcagcca acagaacatg gacattgagt    480
tgtccaccct ctccttgagc aacgagcttc tcttggagtc catcaagact gagagcaagt    540
tggagaacta caccaaggtc atgggagatg ctctccacct tcagaccaag cggtgcaactc    600 cataccatga tgcctacgag aacgtcaggg aggtcatcca acttcaagac cctggtcttg    660
agcaactcaa cgcttctcca gccattgctg gtttgatgca ccaggcatcc ttgctcggta    720
tcaacgcctc catctctcct gagttgttca acatcttgac tgaggagatc actgagggca    780
acgctgagga gttgtacaag aagaacttcg gcaacattga gccagcctct cttgcaatgc    840
ctgagtacct caagaggtac tacaacttgt ctgatgagga gctttctcaa ttcattggca    900
aggcttccaa cttcggtcaa caggagtaca gcaacaacca gctcatcact ccagttgtga    960
actcctctga tggcactgtg aaggtctacc gcatcacacg tgagtacacc acaaacgcct   1020
accaaatgga tgttgagttg ttcccattcg gtggtgagaa ctacagactt gactacaagt   1080
tcaagaactt ctacaacgcc tcctacctct ccatcaagtt gaacgacaag agggagcttg   1140
tcaggactga gggtgctcct caagtgaaca ttgagtactc tgccaacatc accctcaaca   1200
cagctgacat ctctcaacca ttcgagattg gtttgaccag agtccttccc tctggctcct   1260
gggcctacgc tgcagccaag ttcactgttg aggagtacaa ccagtactct ttcctcttga   1320
agctcaacaa ggcaattcgt ctcagcagag ccactgagtt gtctcccacc atcttggagg   1380
gcattgtgag gtctgtcaac cttcaacttg acatcaacac tgatgtgctt ggcaaggtct   1440
tcctcaccaa gtactacatg caacgctacg ccatccatgc tgagactgca ctcatcctct   1500
```

```
gcaacgcacc catctctcaa cgctcctacg acaaccagcc ttcccagttc gacaggctct    1560
tcaacactcc tctcttgaac ggccagtact tctccactgg tgatgaggag attgacctca    1620
actctggctc cacaggtgac tggagaaaga ccatcttgaa gagggccttc aacattgatg    1680
atgtctctct cttccgtctc ttgaagatca cagatcacga caacaaggat ggcaagatca    1740
agaacaactt gaagaacctt tccaacctct acattggcaa gttgcttgca gacatccacc    1800
aactcaccat tgatgagttg gacctcttgc tcattgcagt cggtgagggc aagaccaacc    1860
tctctgcaat ctctgacaag cagttggcaa ccctcatcag gaagttgaac accatcacct    1920
cctggcttca cacccagaag tggtctgtct tccaactctt catcatgacc agcacctcct    1980
acaacaagac cctcactcct gagatcaaga acctcttgga cacagtctac cacggtctcc    2040
aaggcttcga caaggacaag gctgacttgc ttcatgtcat ggctccctac attgcagcca    2100
ccctccaact ctcctctgag aacgtggctc actctgtctt gctctgggct gacaagctcc    2160
aacctggtga tggtgccatg actgctgaga agttctggga ctggctcaac accaagtaca    2220
caccaggctc ctctgaggct gttgagactc aagagcacat tgtgcaatac tgccaggctc    2280
ttgcacagtt ggagatggtc taccactcca ctggcatcaa cgagaacgct ttcagactct    2340
tcgtcaccaa gcctgagatg ttcggtgctg ccacaggtgc tgcacctgct catgatgctc    2400
tctccctcat catgttgacc aggttcgctg actgggtcaa cgctcttggt gagaaggctt    2460
cctctgtctt ggctgccttc gaggccaact ccctcactgc tgagcaactt gctgatgcca    2520
tgaaccttga tgccaacctc ttgctccaag cttccattca agctcagaac caccaacacc    2580
tcccacctgt cactccagag aacgctttct cctgctggac ctccatcaac accatcctcc    2640
aatgggtcaa cgtggctcag caactcaacg tggctccaca aggtgtctct gctttggtcg    2700
gtcttgacta catccagtcc atgaaggaga caccaaccta cgctcaatgg gagaacgcag    2760
ctggtgtctt gactgctggt ctcaactccc aacaggccaa caccctccat gctttcttgg    2820
atgagtctcg ctctgctgcc ctctccacct actacatcag gcaagtcgcc aaggcagctg    2880
ctgccatcaa gtctcgcgat gacctctacc aatacctcct cattgacaac caggtctctg    2940
ctgccatcaa gaccaccagg atcgctgagg ccatcgcttc catccaactc tacgtcaacc    3000
gcgctcttga gaacgttgag gagaacgcca actctggtgt catctctcgc caattcttca    3060
tcgactggga caagtacaac aagaggtact ccacctgggc tggtgtctct caacttgtct    3120
actacccaga gaactacatt gacccaacca tgaggattgg tcagaccaag atgatggatg    3180
ctctcttgca atctgtctcc caaagccaac tcaacgctga cactgtggag gatgccttca    3240
tgagctacct cacctccttc gagcaagttg ccaacctcaa ggtcatctct gcttaccatg    3300
acaacatcaa caacgaccaa ggtctcacct acttcattgg tctctctgag actgatgctg    3360
gtgagtacta ctggagatcc gtggaccaca gcaagttcaa cgatggcaag ttcgctgcaa    3420
acgcttggtc tgagtggcac aagattgact gccctatcaa cccatacaag tccaccatca    3480
gacctgtcat ctacaagagc cgcctctact tgctctggct tgagcagaag gagatcacca    3540
agcaaactgg caactccaag gatggttacc aaactgagac tgactaccgc tacgagttga    3600
agttggctca catccgctac gatggtacct ggaacactcc aatcaccttc gatgtcaaca    3660
agaagatcag cgagttgaag ttggagaaga accgtgctcc tggtctctac tgcgctggtt    3720
accaaggtga ggacaccctc ttggtcatgt tctacaacca gcaagacacc cttgactcct    3780
acaagaacgc ttccatgcaa ggtctctaca tcttcgctga catggcttcc aaggacatga    3840
ctccagagca aagcaacgtc taccgtgaca actcctacca acagttcgac accaacaacg    3900
```

-continued

```
tcaggcgtgt caacaacaga tacgctgagg actacgagat cccaagctct gtcagctctc   3960
gcaaggacta cggctggggt gactactacc tcagcatggt gtacaacggt gacatcccaa   4020
ccatcaacta caaggctgcc tcttccgacc tcaaaatcta catcagccca agctcagga    4080
tcatccacaa cggctacgag ggtcagaaga ggaaccagtg caacttgatg aacaagtacg   4140
gcaagttggg tgacaagttc attgtctaca cctctcttgg tgtcaaccca acaacagct    4200
ccaacaagct catgttctac ccagtctacc aatactctgg caacacctct ggtctcaacc   4260
agggtagact cttgttccac agggacacca cctacccaag caaggtggag cttggattc    4320
ctggtgccaa gaggtccctc accaaccaga acgctgccat ggtgatgac tacgccacag    4380
actccctcaa caagcctgat gacctcaagc agtacatctt catgactgac tccaagggca   4440
cagccactga tgtctctggt ccagtggaga tcaacactgc aatcagccca gccaaggtcc   4500
aaatcattgt caaggctggt ggcaaggagc aaaccttcac agctgacaag gatgtctcca   4560
tccagccaag cccatccttc gatgagatga actaccaatt caacgctctt gagattgatg   4620
gttctggcct caacttcatc aacaactctg cttccattga tgtcaccttc actgccttcg   4680
ctgaggatgg ccgcaagttg ggttacgaga gcttctccat cccagtcacc cttaaggttt   4740
ccactgacaa cgcactcacc cttcatcaca acgagaacgg tgctcagtac atgcaatggc   4800
aaagctaccg caccaggttg aacaccctct cgcaaggca acttgtggcc cgtgccacca    4860
caggcattga caccatcctc agcatggaga cccagaacat ccaagagcca cagttgggca   4920
agggtttcta cgccaccttc gtcatcccac cttacaacct cagcactcat ggtgatgaga   4980
ggtggttcaa gctctacatc aagcacgtgg ttgacaacaa ctcccacatc atctactctg   5040
gtcaactcac tgacaccaac atcaacatca ccctcttcat cccacttgac gatgtcccac   5100
tcaaccagga ctaccatgcc aaggtctaca tgaccttcaa gaagtctcca tctgatggca   5160
cctggtgggg tccacacttc gtccgtgatg acaagggcat cgtcaccatc aacccaaagt   5220
ccatcctcac ccacttcgag tctgtcaacg ttctcaacaa catctcctct gagccaatgg   5280
acttctctgg tgccaactcc ctctacttct gggagttgtt ctactacaca ccaatgcttg   5340
tggctcaaag gttgctccat gagcagaact tcgatgaggc caacaggtgg ctcaagtacg   5400
tctggagccc atctggttac attgtgcatg gtcaaatcca gaactaccaa tggaacgtca   5460
ggccattgct tgaggacacc tcctggaact ctgacccact tgactctgtg gaccctgatg   5520
ctgtggctca acatgaccca atgcactaca gtaggagct c                        5561
```

<210> SEQ ID NO 8
<211> LENGTH: 5816
<212> TYPE: DNA
<213> ORGANISM: Photorhabdus luminescens

<400> SEQUENCE: 8

```
ccatggctaa cgagtccgtc aaggagatcc cagacgtcct caagtcccaa tgcggtttca     60
actgcctcac tgacatctcc cacagctcct tcaacgagtt cagacaacaa gtctctgagc    120
acctctcctg gtccgagacc catgacctct ccatgacgc tcagcaagct cagaaggaca    180
acaggctcta cgaggctagg atcctcaaga gggctaaccc acaactccag aacgctgtcc    240
acctcgccat cttggctcca aacgctgagt tgattggtta caacaaccag ttctctggca    300
gagctagcca gtacgtggct cctggtacag tctcctccat gttcagccca gccgcttacc    360
tcactgagtt gtaccgcgag gctaggaacc ttcatgcttc tgactccgtc tactacttgg    420
acacacgcag accagacctc aagagcatgg ccctcagcca acagaacatg gacattgagt    480
```

```
tgtccaccct ctccttgagc aacgagcttc tcttggagtc catcaagact gagagcaagt      540
tggagaacta caccaaggtc atggagatgc tctccacctt cagaccaagc ggtgcaactc      600
cataccatga tgcctacgag aacgtcaggg aggtcatcca acttcaagac cctggtcttg      660
agcaactcaa cgcttctcca gccattgctg gtttgatgca ccaggcatcc ttgctcggta      720
tcaacgcctc catctctcct gagttgttca acatcttgac tgaggagatc actgagggca      780
acgctgagga gttgtacaag aagaacttcg caacattga gccagcctct cttgcaatgc       840
ctgagtacct caagaggtac tacaacttgt ctgatgagga gctttctcaa ttcattggca      900
aggcttccaa cttcggtcaa caggagtaca gcaacaacca gctcatcact ccagttgtga      960
actcctctga tggcactgtg aaggtctacc gcatcacacg tgagtacacc acaaacgcct     1020
accaaatgga tgttgagttg ttcccattcg gtggtgagaa ctacagactt gactacaagt     1080
tcaagaactt ctacaacgcc tcctacctct ccatcaagtt gaacgacaag agggagcttg     1140
tcaggactga gggtgctcct caagtgaaca ttgagtactc tgccaacatc ccctcaaca     1200 cagctgacat ctctcaacca ttcgagattg gtttgaccag agtccttccc tctggctcct     1260
gggcctacgc tgcagccaag ttcactgttg aggagtacaa ccagtactct ttcctcttga     1320
agctcaacaa ggcaattcgt ctcagcagag ccactgagtt gtctcccacc atcttggagg     1380
gcattgtgag gtctgtcaac cttcaacttg acatcaacac tgatgtgctt ggcaaggtct     1440
tcctcaccaa gtactacatg caacgctacg ccatccatgc tgagactgca ctcatcctct     1500
gcaacgcacc catctctcaa cgctcctacg acaaccagcc ttcccagttc gacaggctct     1560
tcaacactcc tctcttgaac ggccagtact tctccactgg tgatgaggag attgacctca     1620
actctggctc cacaggtgac tggagaaaga ccatcttgaa gagggccttc aacattgatg     1680
atgtctctct cttccgtctc ttgaagatca cagatcacga caacaaggat ggcaagatca     1740
agaacaactt gaagaacctt tccaacctct acattggcaa gttgcttgca gacatccacc     1800
aactcaccat tgatgagttg gacctcttgc tcattgcagt cggtgagggc aagaccaacc     1860
tctctgcaat ctctgacaag cagttggcaa ccctcatcag gaagttgaac accatcacct     1920
cctggcttca cacccagaag tggtctgtct tccaactctt catcatgacc agcacctcct     1980
acaacaagac cctcactcct gagatcaaga acctcttgga cacagtctac cacggtctcc     2040
aaggcttcga caaggacaag gctgacttgc ttcatgtcat ggctccctac attgcagcca     2100
ccctccaact ctcctctgag aacgtggctc actctgtctt gctctgggct gacaagctcc     2160
aacctggtga tggtgccatg actgctgaga agttctggga ctggctcaac accaagtaca     2220
caccaggctc ctctgaggct gttgagactc aagagcacat tgtgcaatac tgccaggctc     2280
ttgcacagtt ggagatggtc taccactcca ctggcatcaa cgagaacgct ttcagactct     2340
tcgtcaccaa gcctgagatg ttcggtgctg ccacaggtgc tgcacctgct catgatgctc     2400
tctccctcat catgttgacc aggttcgctg actgggtcaa cgctcttggt gagaaggctt     2460
cctctgtctt ggctgccttc gaggccaact ccctcactgc tgagcaactt gctgatgcca     2520
tgaaccttga tgccaacctc ttgctccaag cttccattca agctcagaac caccaacacc     2580
tcccacctgt cactccagag aacgctttct cctgctggac ctccatcaac accatcctcc     2640
aatgggtcaa cgtggctcag caactcaacg tggctccaca aggtgtctct gctttggtcg     2700
gtcttgacta catccagtcc atgaaggaga caccaaccta cgctcaatgg gagaacgcag     2760
ctggtgtctt gactgctggt ctcaactccc aacaggccaa caccctccat gctttcttgg     2820
atgagtctcg ctctgctgcc ctctccacct actacatcag gcaagtcgcc aaggcagctg     2880
```

```
ctgccatcaa gtctcgcgat gacctctacc aatacctcct cattgacaac caggtctctg    2940
ctgccatcaa gaccaccagg atcgctgagg ccatcgcttc catccaactc tacgtcaacc    3000
gcgctcttga gaacgttgag gagaacgcca actctggtgt catctctcgc caattcttca    3060
tcgactggga caagtacaac aagaggtact ccacctgggc tggtgtctct caacttgtct    3120
actacccaga gaactacatt gacccaacca tgaggattgg tcagaccaag atgatggatg    3180
ctctcttgca atctgtctcc caaagccaac tcaacgctga cactgtggag gatgccttca    3240
tgagctacct cacctccttc gagcaagttg ccaacctcaa ggtcatctct gcttaccatg    3300
acaacatcaa caacgaccaa ggtctcacct acttcattgg tctctctgag actgatgctg    3360
gtgagtacta ctggagatcc gtggaccaca gcaagttcaa cgatggcaag ttcgctgcaa    3420
acgcttggtc tgagtggcac aagattgact gccctatcaa cccatacaag tccaccatca    3480
gacctgtcat ctacaagagc cgcctctact tgctctggct tgagcagaag gagatcacca    3540
agcaaactgg caactccaag gatggttacc aaactgagac tgactaccgc tacgagttga    3600
agttggctca catccgctac gatggtacct ggaacactcc aatcaccttc gatgtcaaca    3660
agaagatcag cgagttgaag ttggagaaga accgtgctcc tggtctctac tgcgctggtt    3720
accaaggtga ggacaccctc ttggtcatgt tctacaacca gcaagacacc cttgactcct    3780
acaagaacgc ttccatgcaa ggtctctaca tcttcgctga catggcttcc aaggacatga    3840
ctccagagca aagcaacgtc taccgtgaca actcctacca acagttcgac accaacaacg    3900
tcaggcgtgt caacaacaga tacgctgagg actacgagat cccaagctct gtcagctctc    3960
gcaaggacta cggctggggt gactactacc tcagcatggt gtacaacggt gacatcccaa    4020
ccatcaacta caaggctgcc tcttccgacc tcaaaatcta catcagccca agctcagga    4080
tcatccacaa cggctacgag ggtcagaaga ggaaccagtg caacttgatg aacaagtacg    4140
gcaagtgggg tgacaagttc attgtctaca cctctcttgg tgtcaaccca acaacagct    4200
ccaacaagct catgttctac ccagtctacc aatactctgg caacacctct ggtctcaacc    4260
agggtagact cttgttccac agggacacca cctacccaag caaggtggag gcttggattc    4320
ctggtgccaa gaggtccctc accaaccaga acgctgccat ggtgatgac tacgccacag    4380
actccctcaa caagcctgat gacctcaagc agtacatctt catgactgac tccaagggca    4440
cagccactga tgtctctggt ccagtggaga tcaaacactgc aatcagccca gccaaggtcc    4500
aaaatcattgt caaggctggt ggcaaggagc aaaccttcac agctgacaag gatgtctcca    4560
tccagccaag cccatccttc gatgagatga actaccaatt caacgctctt gagattgatg    4620
gttctggcct caacttcatc aacaactctg cttccattga tgtcaccttc actgccttcg    4680
ctgaggatgg ccgcaagttg ggttacgaga gcttctccat cccagtcacc cttaaggttt    4740
ccactgacaa cgcactcacc cttcatcaca acgagaacgg tgctcagtac atgcaatggc    4800
aaagctaccg caccaggttg aacaccctct tcgcaaggca acttgtggcc cgtgccacca    4860
caggcattga caccatcctc agcatggaga cccagaacat ccaagagcca cagttgggca    4920
agggtttcta cgccaccttc gtcatcccac cttacaacct cagcactcat ggtgatgaga    4980
ggtggttcaa gctctacatc aagcacgtgg ttgacaacaa ctcccacatc atctactctg    5040
gtcaactcac tgcacccaac atcaacatca ccctcttcat cccacttgac gatgtcccac    5100
tcaaccagga ctaccatgcc aaggtctaca tgaccttcaa gaagtctcca tctgatggca    5160
cctggtgggg tccacactttc gtccgtgatg acagggcat cgtcaccatc aacccaaagt    5220
ccatcctcac ccacttcgag tctgtcaacg ttctcaacaa catctcctct gagccaatgg    5280
```

-continued

```
acttctctgg tgccaactcc ctctacttct gggagttgtt ctactacaca ccaatgcttg    5340
tggctcaaag gttgctccat gagcagaact tcgatgaggc caacaggtgg ctcaagtacg    5400
tctggagccc atctggttac attgtgcatg gtcaaatcca gaactaccaa tggaacgtca    5460
ggccattgct tgaggacacc tcctggaact ctgacccact tgactctgtg gaccctgatg    5520
ctgtggctca acatgaccca atgcactaca aggtctccac cttcatgagg accttggacc    5580
tcttgattgc cagaggtgac catgcttacc gccaattgga gagggacacc ctcaacgagg    5640
caaagatgtg gtacatgcaa gctctccacc tcttgggtga caagccatac ctcccactca    5700
gcaccacttg gtccgaccca aggttggacc gtgctgctga catcaccact cagaacgctc    5760
atgactctgc cattgttgct ctcaggcaga acatcccaac tcctgctcca ctctcc        5816
```

<210> SEQ ID NO 9
<211> LENGTH: 5301
<212> TYPE: DNA
<213> ORGANISM: Photorhabdus luminescens

<400> SEQUENCE: 9

```
ccatggctga gttgattggt tacaacaacc agttctctgg cagagctagc cagtacgtgg      60
ctcctggtac agtctcctcc atgttcagcc agccgctta cctcactgag ttgtaccgcg     120
aggctaggaa ccttcatgct tctgactccg tctactactt ggacacacgc agaccagacc     180
tcaagagcat ggccctcagc caacagaaca tggacattga gttgtccacc ctctccttga     240
gcaacgagct tctcttggag tccatcaaga ctgagagcaa gttggagaac tacaccaagg     300
tcatggagat gctctccacc ttcagaccaa gcggtgcaac tccataccat gatgcctacg     360
agaacgtcag ggaggtcatc caacttcaag accctggtct tgagcaactc aacgcttctc     420
cagccattgc tggttttgatg caccaggcat ccttgctcgg tatcaacgcc tccatctctc     480
ctgagttgtt caacatcttg actgaggaga tcactgaggg caacgctgag gagttgtaca     540
agaagaactt cggcaacatt gagccagcct ctcttgcaat gcctgagtac ctcaagaggt     600
actacaactt gtctgatgag gagctttctc aattcattgg caaggcttcc aacttcggtc     660
aacaggagta cagcaacaac cagctcatca ctccagttgt gaactcctct gatggcactg     720
tgaaggtcta ccgcatcaca cgtgagtaca ccacaaacgc ctaccaaatg gatgttgagt     780
tgttcccatt cggtggtgag aactacagac ttgactacaa gttcaagaac ttctacaacg     840
cctcctacct ctccatcaag ttgaacgaca gagggagct tgtcaggact gagggtgctc     900
ctcaagtgaa cattgagtac tctgccaaca tcaccctcaa cacagctgac atctctcaac     960
cattcgagat tggtttgacc agagtccttc cctctggctc ctgggcctac gctgcagcca    1020
agttcactgt tgaggagtac aaccagtact cttttcctctt gaagctcaac aaggcaattc    1080
gtctcagcag agccactgag ttgtctccca ccatcttgga gggcattgtg aggtctgtca    1140
accttcaact tgcatcaac actgatgtgc ttggcaaggt cttcctcacc aagtactaca    1200
tgcaacgcta cgccatccat gctgagactg cactcatcct ctgcaacgca cccatctctc    1260
aacgctccta cgacaaccag ccttcccagt tcgacaggtc cttcaacact cctctcttga    1320
acggccagta cttctccact ggtgatgagg agattgacct caactctggc tccacaggtg    1380
actggagaaa gaccatcttg aagagggcct tcaacattga tgatgtctct ctcttccgtc    1440
tcttgaagat cacagatcac gacaacaagg atggcaagat caagaacaac ttgaagaacc    1500
tttccaacct ctacattggc aagttgcttg cagacatcca ccaactcacc attgatgagt    1560
tggacctctt gctcattgca gtcggtgagg gcaagaccaa cctctctgca atctctgaca    1620
```

-continued

```
agcagttggc aaccctcatc aggaagttga acaccatcac ctcctggctt cacacccaga   1680
agtggtctgt cttccaactc ttcatcatga ccagcacctc ctacaacaag accctcactc   1740
ctgagatcaa gaacctcttg gacacagtct accacggtct ccaaggcttc gacaaggaca   1800
aggctgactt gcttcatgtc atggctccct acattgcagc caccctccaa ctctcctctg   1860
agaacgtggc tcactctgtc ttgctctggg ctgacaagct ccaacctggt gatggtgcca   1920
tgactgctga agttctggg actggctca acaccaagta cacaccaggc tcctctgagg     1980
ctgttgagac tcaagagcac attgtgcaat actgccaggc tcttgcacag ttggagatgg   2040
tctaccactc cactggcatc aacgagaacg ctttcagact cttcgtcacc aagcctgaga   2100
tgttcggtgc tgccacaggt gctgcacctg ctcatgatgc tctctccctc atcatgttga   2160
ccaggttcgc tgactgggtc aacgctcttg gtgagaaggc ttcctctgtc ttggctgcct   2220
tcgaggccaa ctccctcact gctgagcaac ttgctgatgc catgaacctt gatgccaacc   2280
tcttgctcca agcttccatt caagctcaga accaccaaca cctcccacct gtcactccag   2340
agaacgcttt ctcctgctgg acctccatca acaccatcct ccaatgggtc aacgtggctc   2400
agcaactcaa cgtggctcca caaggtgtct ctgctttggt cggtcttgac tacatccagt   2460
ccatgaagga gacaccaacc tacgctcaat gggagaacgc agctggtgtc ttgactgctg   2520
gtctcaactc ccaacaggcc aacaccctcc atgctttctt ggatgagtct cgctctgctg   2580
ccctctccac ctactacatc aggcaagtcg ccaaggcagc tgctgccatc aagtctcgcg   2640
atgacctcta ccaataccct ctcattgaca accaggtctc tgctgccatc aagaccacca   2700
ggatcgctga ggccatcgct tccatccaac tctacgtcaa ccgcgctctt gagaacgttg   2760
aggagaacgc caactctggt gtcatctctc gccaattctt catcgactgg gacaagtaca   2820
acaagaggta ctccacctgg gctggtgtct ctcaacttgt ctactaccca gagaactaca   2880
ttgacccaac catgaggatt ggtcagacca agatgatgga tgctctcttg caatctgtct   2940
cccaaagcca actcaacgct gacactgtgg aggatgcctt catgagctac ctcacctcct   3000
tcgagcaagt tgccaacctc aaggtcatct ctgcttacca tgacaacatc aacaacgacc   3060
aaggtctcac ctacttcatt ggtctctctg agactgatgc tggtgagtac tactggagat   3120
ccgtggacca cagcaagttc aacgatggca agttcgctgc aaacgcttgg tctgagtggc   3180
acaagattga ctgccctatc aacccataca agtccaccat cagacctgtc atctacaaga   3240
gccgcctcta cttgctctgg cttgagcaga aggagatcac caagcaaact ggcaactcca   3300
aggatggtta ccaaactgag actgactacc gctacgagtt gaagttggct cacatccgct   3360
acgatggtac ctggaacact ccaatcaccct tcgatgtcaa caagaagatc agcgagttga   3420
agttggagaa gaaccgtgct cctggtctct actgcgctgg ttaccaaggt gaggacaccc   3480
tcttggtcat gttctacaac cagcaagaca cccttgactc ctacaagaac gcttccatgc   3540
aaggtctcta catcttcgct gacatggctt ccaaggacat gactccagag caaagcaacg   3600
tctaccgtga caactcctac aacagttcg acaccaacaa cgtcaggcgt gtcaacaaca   3660
gatacgctga ggactacgag atcccaagct ctgtcagctc tcgcaaggac tacggctggg   3720
gtgactacta cctcagcatg gtgtacaacg gtgacatccc aaccatcaac tacaaggctg   3780
cctcttccga cctcaaaatc tacatcagcc caaagctcag gatcatccac aacgctacg    3840
agggtcagaa gaggaaccag tgcaacttga tgaacaagta cggcaagttg ggtgacaagt   3900
tcattgtcta cacctctctt ggtgtcaacc caaacaacag ctccaacaag ctcatgttct   3960
acccagtcta ccaatactct ggcaacacct ctggtctcaa ccagggtaga ctcttgttcc   4020
```

```
acagggacac cacctaccca agcaaggtgg aggcttggat tcctggtgcc aagaggtccc    4080
tcaccaacca gaacgctgcc attggtgatg actacgccac agactccctc aacaagcctg    4140
atgacctcaa gcagtacatc ttcatgactg actccaaggg cacagccact gatgtctctg    4200
gtccagtgga gatcaacact gcaatcagcc cagccaaggt ccaaatcatt gtcaaggctg    4260
gtggcaagga gcaaaccttc acagctgaca aggatgtctc catccagcca agcccatcct    4320
tcgatgagat gaactaccaa ttcaacgctc ttgagattga tggttctggc ctcaacttca    4380
tcaacaactc tgcttccatt gatgtcacct tcactgcctt cgctgaggat ggccgcaagt    4440
tgggttacga gagcttctcc atcccagtca cccttaaggt ttccactgac aacgcactca    4500
cccttcatca caacgagaac ggtgctcagt acatgcaatg gcaaagctac cgcaccaggt    4560
tgaacaccct cttcgcaagg caacttgtgg cccgtgccac cacaggcatt gacaccatcc    4620
tcagcatgga gacccagaac atccaagagc acagttggg caagggtttc tacgccacct    4680
tcgtcatccc accttacaac ctcagcactc atggtgatga gaggtggttc aagctctaca    4740
tcaagcacgt ggttgacaac aactcccaca tcatctactc tggtcaactc actgacacca    4800
acatcaacat caccctcttc atcccacttg acgatgtccc actcaaccag gactaccatg    4860
ccaaggtcta catgaccttc aagaagtctc catctgatgg cacctggtgg ggtccacact    4920
tcgtccgtga tgacaagggc atcgtcacca tcaacccaaa gtccatcctc acccacttcg    4980
agtctgtcaa cgttctcaac aacatctcct ctgagccaat ggacttctct ggtgccaact    5040
ccctctactt ctgggagttg ttctactaca caccaatgct tgtggctcaa aggttgctcc    5100
atgagcagaa cttcgatgag gccaacaggt ggctcaagta cgtctggagc ccatctggtt    5160
acattgtgca tggtcaaatc cagaactacc aatggaacgt caggccattg cttgaggaca    5220
cctcctggaa ctctgaccca cttgactctg tggaccctga tgctgtggct caacatgacc    5280
caatgcacta caagtgagct c                                              5301

<210> SEQ ID NO 10
<211> LENGTH: 1750
<212> TYPE: DNA
<213> ORGANISM: Photorhabdus luminescens

<400> SEQUENCE: 10
ccatggctca gatctgctaa caccctcact gacttgttcc tcccacagat caacgaggtc      60
atgatgaact actggcaaac cttggctcaa agggtctaca acctcagaca caacctctcc     120
attgatggtc aaccactcta cctcccaatc tacgccacac cagctgaccc aaaggctctt     180
ctctctgctg ctgtggctac cagccaaggt ggtggcaagc tcccagagtc cttcatgtcc     240
ctctggaggt tccacacat gttggagaac gcccgtggca tggtctccca actcacccag     300
ttcggttcca ccctccagaa catcattgag aggcaagatg ctgaggctct caacgctttg     360
ctccagaacc aggcagctga gttgatcctc accaacttgt ccatccaaga caagaccatt     420
gaggagcttg atgctgagaa gacagtcctt gagaagagca aggctggtgc ccaatctcgc     480
ttcgactcct acggcaagct ctacgatgag aacatcaacg ctggtgagaa ccaggccatg     540
accctcaggg cttccgcagc tggtctcacc actgctgtcc aagcctctcg cttggctggt     600
gcagctgctg acctcgttcc aaacatcttc ggtttcgctg gtggtggctc cagatggggt     660
gccattgctg aggctaccgg ttacgtcatg gagttctctg ccaacgtcat gaacactgag     720
gctgacaaga tcagccaatc tgagacctac agaaggcgcc gtcaagagtg ggagatccaa     780
aggaacaacg ctgaggcaga gttgaagcaa atcgatgctc aactcaagtc cttggctgtc     840
```

-continued

```
agaagggagg ctgctgtcct ccagaagacc tccctcaaga cccaacagga gcaaacccag        900
tcccagttgg ctttcctcca aaggaagttc tccaaccagg ctctctacaa ctggctcaga        960
ggccgcttgg ctgccatcta cttccaattc tacgaccttg ctgtggccag gtgcctcatg       1020
gctgagcaag cctaccgctg ggagttgaac gatgactccg ccaggttcat caagccaggt       1080
gcttggcaag gcacctacgc tggtctcctt gctggtgaga ccctcatgct ctccttggct       1140
caaatggagg atgctcacct caagagggac aagagggctt tggaggtgga gaggacagtc       1200
tcccttgctg aggtctacgc tggtctccca aaggacaacg gtccattctc ccttgctcaa       1260
gagattgaca agttggtcag ccaaggttct ggttctgctg gttctggtaa caacaacttg       1320
gctttcggcg ctggtactga caccaagacc tccctccaag cctctgtctc cttcgctgac       1380
ctcaagatca gggaggacta cccagcttcc cttggcaaga tcaggcgcat caagcaaatc       1440
tctgtcaccc tcccagctct cttgggtcca taccaagatg tccaagcaat cctctcctac       1500
ggtgacaagg ctggtttggc gaacggttgc gaggctcttg ctgtctctca tggcatgaac       1560
gactctggtc aattccaact tgacttcaac gatggcaagt tcctcccatt cgagggcatt       1620
gccattgacc aaggcaccct caccctctcc ttcccaaacg cttccatgcc agagaaggga       1680
aagcaagcca ccatgctcaa gaccctcaac gatatcatcc tccacatcag gtacaccatc       1740
aagtgagctc                                                              1750
```

USE OF UNTRANSLATED REGION OF OSMOTIN GENE TO ENHANCE TRANSGENE EXPRESSION IN PLANTS

This application claims the benefit of U.S. Provisional Application No. 60/416,142 filed on Oct. 4, 2002 and is being filed as a Divisional Application of U.S. Ser. No. 10/703,280 filed on Nov. 7, 2003 now abandoned. The present invention relates to plant molecular biology and the application of genetic engineering techniques to plants. More particularly, the present invention provides DNA sequences, constructs and methods that are useful for enhancing the expression of recombinant genes in plants.

FIELD OF THE INVENTION

Background of the Invention

Recombinant DNA technology and genetic engineering have made it routinely possible to introduce desired DNA sequences into plant cells to allow for the expression of proteins of interest. For commercially viable transformation events, however, obtaining desired levels of stable and predictable expression in important crops remains challenging.

One method of expressing heterologous genes at desired levels in crops involves manipulation of the regulatory mechanisms governing expression in plants. The regulation may be transcriptional or post-transcriptional and can include, for example, mechanisms to enhance, limit, or prevent transcription of the DNA, as well as mechanisms that limit or increase the life span of an mRNA after it is produced. The DNA sequences involved in these regulatory processes can be located upstream, downstream or even internally to the structural DNA sequences encoding the protein product of a gene.

To regulate transcription in a transgenic plant, various types of promoters may be employed. Promoters can be used to control the expression of foreign genes in transgenic plants in a manner similar to the expression pattern of the gene from which the promoter was originally derived. Generally, promoters are classified in two categories. "Constitutive" promoters express in most tissues most of the time. Expression from a constitutive promoter is more or less at a steady state level throughout development. Genes encoding proteins with house-keeping functions are often driven by constitutive promoters. Examples of constitutively expressed genes in maize include actin and ubiquitin. (Wilmink et al., *Plant Mol. Biol.*, 28:949-955, 1995). "Regulated" promoters are typically expressed in only certain tissue types (tissue specific promoters) or at certain times during development (temporal promoters).

Further improvements in transcription have been obtained in transgenic plants by placing "enhancer" sequences upstream (5') of the promoter. Enhancer elements are cis-acting and increase the level of transcription of an adjacent gene from its promoter in a fashion that is relatively independent of the upstream position and orientation of the enhancer. Such sequences have been isolated from a variety of sources, including viruses, bacteria and plant genes. One example of a well characterized enhancer sequence is the octopine synthase (ocs) enhancer from the *Agrobacterium tumefaciens*, as described in U.S. Pat. Nos. 5,837,849, 5,710,267 and 5,573,932, assigned to the assignee of the present invention. This short (40 bp) sequence has been shown to increase gene expression in both dicots and monocots, including maize, by significant levels. Tandem repeats of this enhancer have been shown to increase expression of the GUS gene eight-fold in maize. It remains unclear how these enhancer sequences function. Presumably enhancers bind activator proteins and thereby facilitate the binding of RNA polymerase II to the TATA box. WO95/14098 describes testing of various multiple combinations of the ocs enhancer and the mas (mannopine synthase) enhancer which resulted in several hundred fold increase in gene expression of the GUS gene in transgenic tobacco callus.

The use of a specific promoter, with or without one or more enhancers, however, does not necessarily guarantee desired levels of gene expression in plants. In addition to desired transcription levels, other factors such as improper splicing, polyadenylation and nuclear export can affect accumulation of both mRNA and the protein of interest. Therefore, methods of increasing RNA stability and translational efficiency through mechanisms of post-transcriptional regulation are needed in the art.

With regard to post-transcriptional regulation, it is has been demonstrated that certain 5' and 3' untranslated regions (UTRs) of eukaryotic mRNAs play a major role in translational efficiency and RNA stability, respectively. For example, the 5' and 3' UTRs of tobacco mosaic virus (TMV) and alfalfa mosiac virus (AMV) coat protein mRNAs can enhance gene expression 5.4-fold and 3.0 fold in tobacco plants, respectively. (Zeyenko, *FEBS Lett.*, November 14; 354(3):271-3 (1994)). The 5' and 3' UTRs of the maize alcohol dehydrogenase-1 (adh1) gene are required for efficient translation in hypoxic protoplasts. (Bailey-Serres et al., *Plant Physiol.*, October; 112(2):685-95 (1996)).

Experiments with various 5' UTR leader sequences demonstrate that various structural features of a 5'UTR can be correlated with levels translational efficiency. Certain 5' UTRs have been found to contain AUG codons which may interact with 40S ribosomal subunits when it scans for the AUG codon at the initiation site, thus decreasing the rate of translation. (Kozak, *Mol. Cell. Biol.* 7:3438 (1987); Kozak, *J. Cell Biol.* 108, 209 (1989)). Further, the 5'UTR nucleotide sequences flanking the AUG initiation site on the mRNA may have an impact on translational efficiency. If the context of the flanking 5'UTR are not favorable, part of the 40S ribosomal subunits might fail to recognize the translation start site such that the rate of polypeptide synthesis will be slowed. (Kozak, *J. Biol. Chem.* 266, 19867-19870 (1991); Pain, *Eur. J. Biochem.* 236, 747-771 (1996)). Secondary structures of 5'UTRs (e.g., hairpin formation) may also hinder the movement of 40S ribosomal subunits during their scanning process and therefore negatively impact the efficiency of translation. (Sonenberg et al., *Nature* 334:320 (1988); Kozak, *Cell* 44:283-292, (1986)). The relative GC content of a 5' UTR sequence has been shown to be an indicator of the stability of the potential secondary structure, with higher levels of GC indicating instability. (Kozak, *J. Biol. Chem.* 266, 19867-19870 (1991). Longer 5' UTRs may exhibit higher numbers of inhibitory secondary structures. (Sonenberg et al., 1996). Thus, the translational efficiency of any given 5' UTR is highly dependent upon its particular structure, and optimization of the leader sequence has been shown to increase gene expression as a direct result of improved translation initiation efficiency. Furthermore, significant increases in gene expression have been produced by addition of leader sequences from plant viruses or heat shock genes. (Raju et al., *Plant Science* 94: 139-149 (1993)).

In addition to 5' UTR sequences, 3' UTR (trailer) sequences of mRNAs are also involved in gene expression. 3' UTRs (also known as polyadenylation elements or adenylation control elements) are known to control the nuclear export, polyadenylation status, subcellular targeting and rates of translation and degradation of mRNA from RNases. In particular, 3' UTRs may contain one or more inverted repeats that can fold into stem-loop structures which act as a barrier to exoribonucleases, as well as interact with proteins known to promoter RNA stability (e.g., RNA binding proteins). (Barkan et al., *A Look Beyond Transcription: Mechanisms Determining mRNA Stability and Translation in Plants*, American Society of Plant Physiologists, Rockville, Md., pp. 162-213 (1998)). Certain elements found within 3' UTRs may be RNA destabilizing, however. One such example occurring in plants is the DST element, which can be found in small auxin up RNAs (SAURs). (Gil et al., *EMBO J.* 15, 1678-1686 (1996)). A further destabilizing feature of some 3' UTRs is the presence of AUUUA pentamers. (Ohme-Takagi et al., *Pro. Nat. Acad. Sci. USA* 90 11811-11815 (1993)).

3' UTRs have been demonstrated to play a significant role in gene expression of several maize genes. Specifically, a 200 base pair 3' sequence has been shown to be responsible for suppression of light induction of the maize small m3 subunit of the ribulose-1,5-biphosphate carboxylase gene (rbc/m3) in mesophyll cells. (Viret et al., *Proc Natl Acad Sci USA.* 91 (18):8577-81 (1994)). In plants, especially maize, this sequence is not very well conserved. One 3' UTR frequently used in genetic engineering of plants is derived from a nopaline synthase gene (3' nos) (Wyatt et al., *Plant Mol Biol* 22(5):731-49 (1993)).

In certain plant viruses, such as alfalfa mosaic virus (AMV) and tobacco mosaic virus (TMV), the highly structured 3' UTRs are essential for replication and can be folded into either a linear array of stem-loop structures which contain several high-affinity coat protein binding sites, or a tRNA-like site recognized by RNA-dependent RNA polymerases. (Olsthoorn et al., *EMBO J* 1; 18(17):4856-64 (1999); Zeyenko et al., 1994)).

As of the date of the present invention, however, the use of 5' and 3' UTRs to regulate the expression of recombinant nucleic acids in transgenic plants has not been wide-spread, mainly because optimal/optimized UTR sequences have yet to be identified or characterized. Novel methods and compositions of matter for regulating gene expression using optimal/optimized 5' and 3' UTRs are therefore needed in the art.

SUMMARY OF THE INVENTION

The present invention provides methods, vectors and gene constructs for enhancing expression of a recombinant nucleic acid sequence in transgenic plants and plant tissues. According to the present invention, nucleic acid sequences are obtained and/or derived from the 5' and 3' untranslated regions of genes encoding osmotin proteins and engineered to flank respective portions of a selected coding region of a vector. The vector construct may be introduced into plants and/or plant tissues through conventional procedures, resulting in enhanced expression of the selected coding region. In a preferred embodiment, the selected coding region is a chimeric gene or gene fragment expressing one or more proteins known to impart a level of insecticidal activity to a transgenic plant and/or plant tissue.

BRIEF DESCRIPTION OF THE FIGURES

FIG. 4 is a Western blot analysis of Toxin A expression in transgenic *Arabidopsis* plants. (A): Lane 1: Recombinant *E. coli* strain; Lane 2: Transgenic plant with CsVMV-GUS-ORF25 gene construct; Lane 3-10: Transgenic plants with construct pDAB7031. (B): Lane 1: Recombinant *E. coli* strain; Lane 2-6: Transgenic plants with construct pDAB7036. The bands below the A2 protein are the antibody cross-reacted background of *Arabidopsis* plants.

Figure 1:
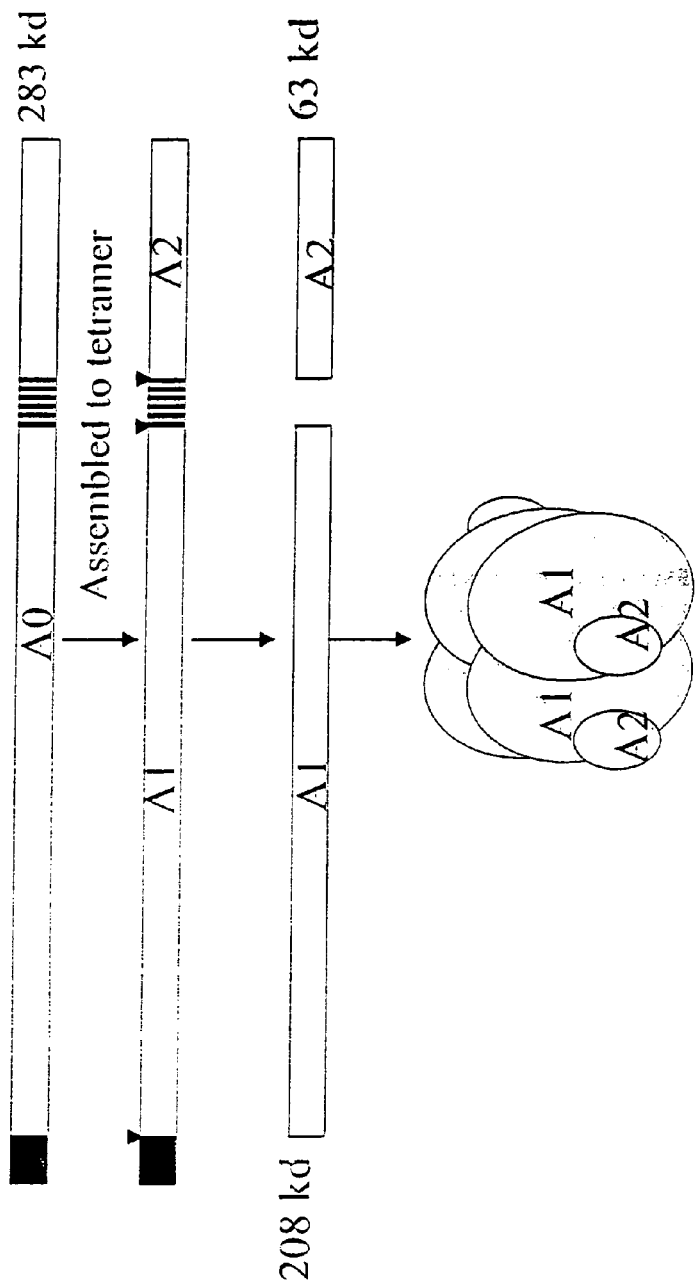
FIG. 1 is a diagram of the putative processing pathway of Toxin A protein and its proposed structure model. The molecular weight for unprocessed A0 protein and cleaved A1 and A2 polypeptides are indicated. (▥): 87 amino acids at N-terminal end; (■): 88 amino acids at C-terminal end of A1 polypeptide.
Figure 2:
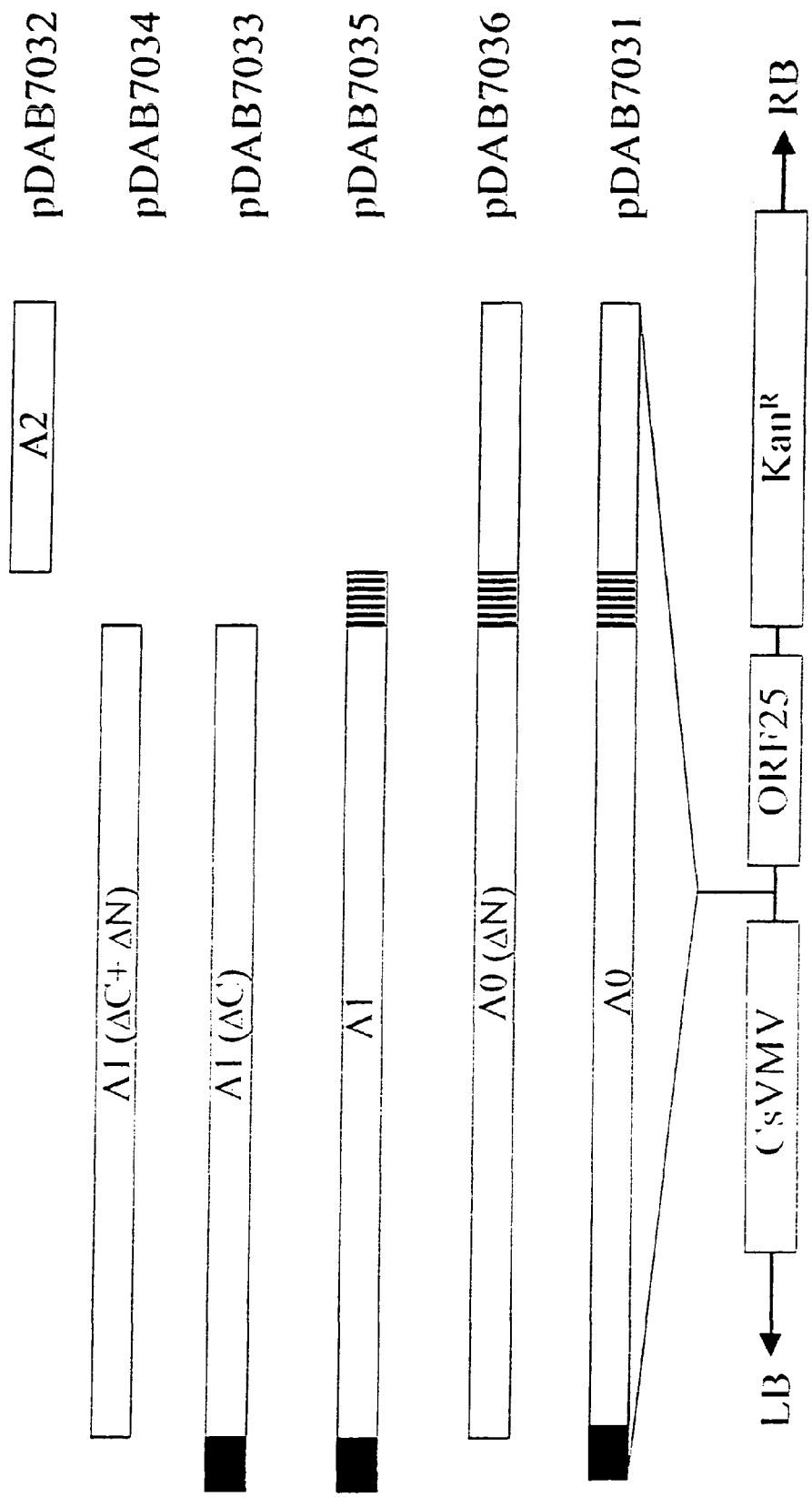
FIG. 2 provides diagrams of the Toxin A gene constructs used for plant transformation. Six different Toxin A gene fragments were inserted between a Cassaya Vein Mosaic Virus (CsVMV) promoter and Ti 15955 plasmid ORF25 3' sequences, respectively. RB: T-DNA right border; LB: T-DNA left border; Kan$^R$: Kanamycin resistance gene. (▥): 87 amino acids at N-terminal end; (■): 88 amino acids at C-terminal end of A1 polypeptide. The designations for each Toxin A gene fragment are shown in diagrams.
Figure 3:
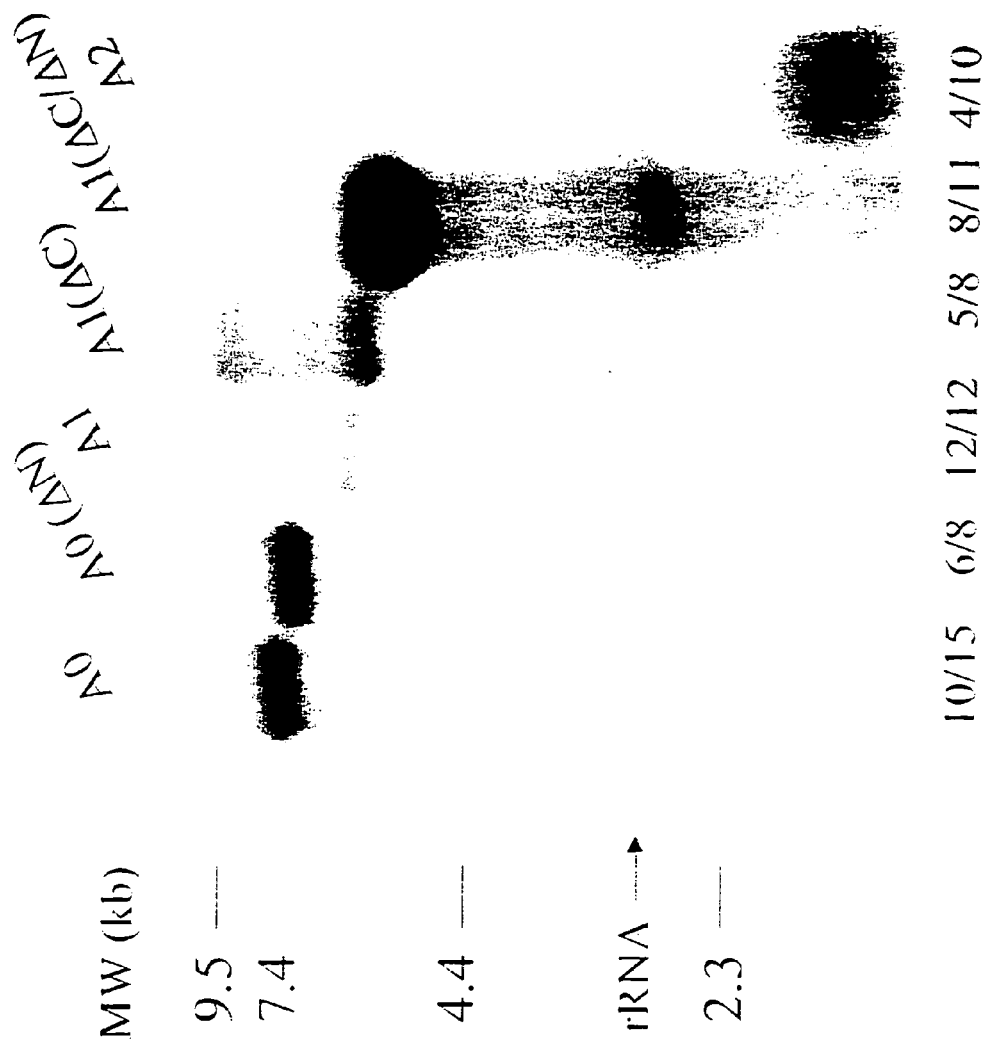
FIG. 3 is a Northern blot analysis showing the RNA expression patterns of transgenic *Arabidopsis* plants carrying six different Toxin A constructs. Above each lane are the names of the Toxin A gene fragments carried by the transgenic plants. The number of the plants with expected RNA expression pattern (as shown in this blot) versus number of examined plants for each construct are indicated below as n/N. MW: molecular weight. The position where non-specific binding of the probe to ribosomal RNA occurs is indicated by an arrow.
Figure 5:
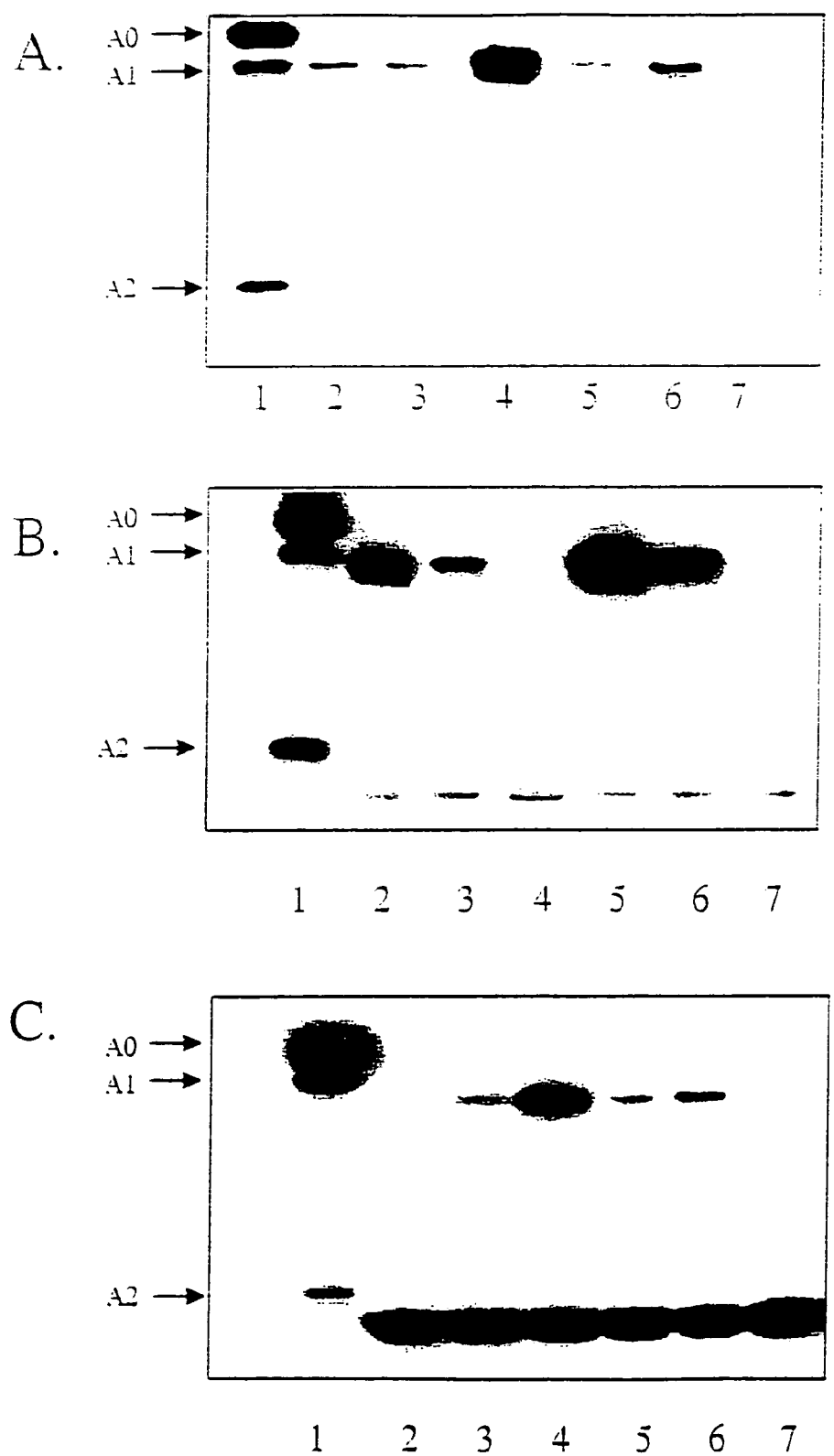
FIG. 5 is a Western blot analysis of A1 protein expression in transgenic *Arabidopsis* plants. (A): Lane 1: Recombinant *E. coli* strain; Lanes 2-6: Transgenic plants with construct pDAB7035; Lane 7: Transgenic plant with GUS gene construct. (B): Lane 1: Recombinant *E. coli* strain; Lanes 2-6: Transgenic plants with construct pDAB7033; Lane 7: Transgenic plant with GUS gene construct. (C): Lane 1: Recombinant *E. coli* strain; Lanes 2-6: Transgenic plants with construct pDAB7034; Lane 7: Transgenic plant with GUS gene construct. The bands below the A2 protein are the antibody cross-reacted background of *Arabidopsis* plants.
Figure 6:
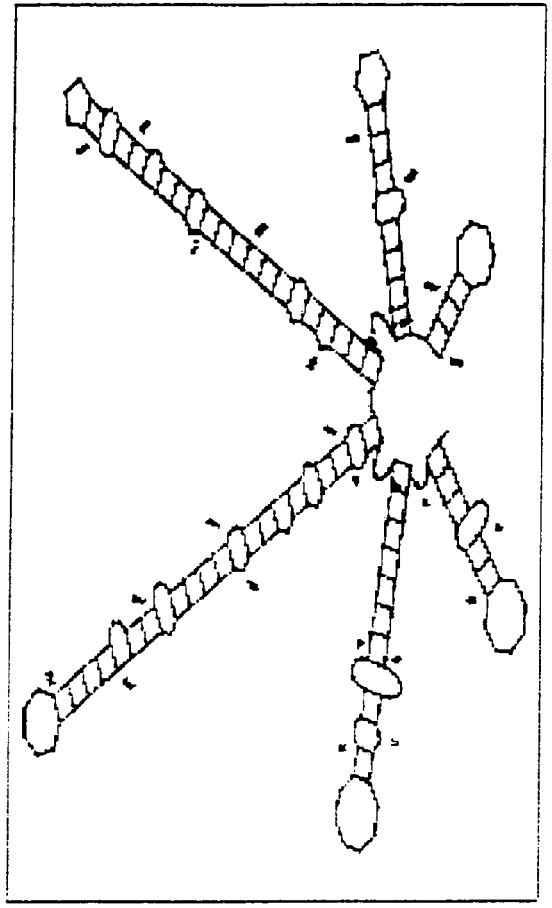
FIG. 6 shows sequences and structural features of 5' and 3' UTRs of the tobacco osmotin gene. (A): DNA sequence of osmotin 5' UTR (SEQ. ID. NO. 1) and its A/T content; (B) Computer-predicted RNA secondary structure of osmotin 3' UTR sequences.
Figure 7:
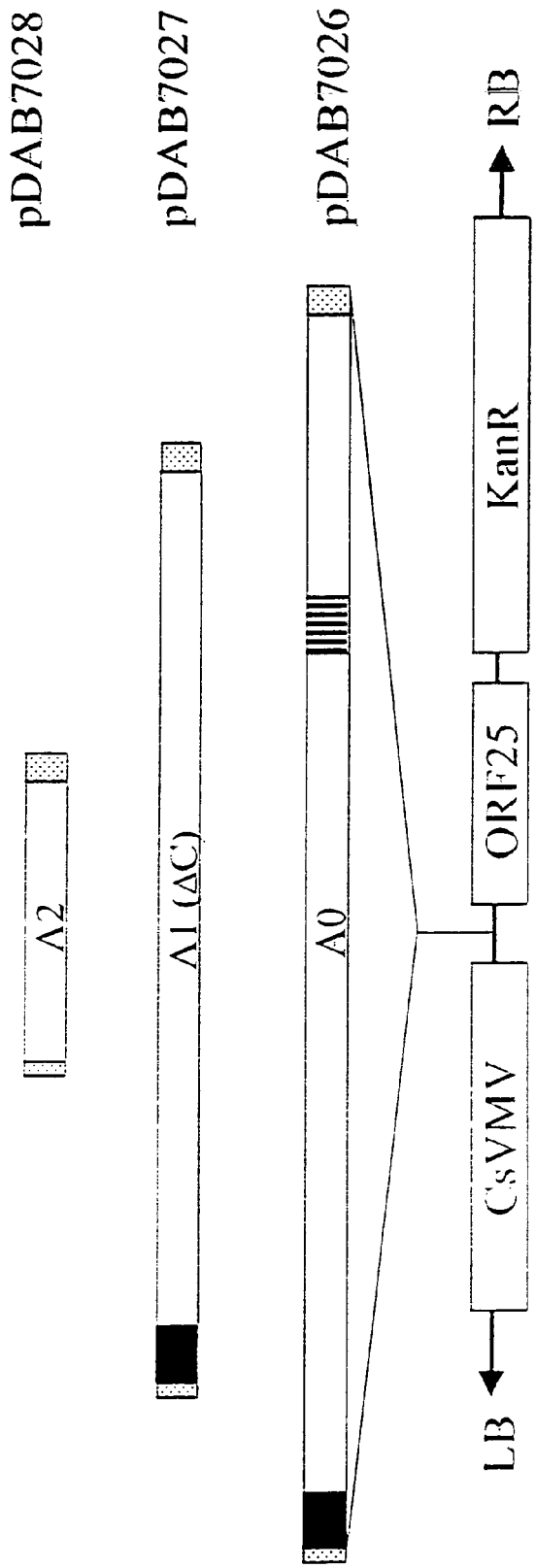
FIG. 7 provides diagrams of the modified Toxin A gene constructs used for plant transformation. The 5' and 3' UTR sequences of tobacco osmotin gene (▨) were added to the both ends of Toxin A genes in constructs pDAB7031, pDAB7033, and pDAB7032 (FIG. 2). The resultant constructs are designated pDAB7026, pDAB7027, and pDAB7028 as indicated on the right. CsVMV: Cassaya Vein Mosaic Virus promoter; ORF 25: ORF25 3' sequences of Ti 15955 plasmid. RB: T-DNA right border; LB: T-DNA left border; Kan$^R$: Kanamycin resistance gene. ■): 87 amino acids at N-terminal end; (▥): 88 amino acids at C-terminal end of A1 polypeptide. The designations for each Toxin A gene fragment are shown in diagrams. The names for each construct are indicated on right.

A "deletion", as used herein, refers to a change in either amino acid or nucleotide sequence in which one or more amino acid or nucleotide residues, respectively, are absent.

A 5' and/or 3' osmotin UTR of the present invention is said to be "functionally linked" to a structural nucleic acid sequence of interest if these elements are situated in relation to another such that the 5' and 3' osmotin UTR influences mRNA stability, translational efficiency of transcription products of the structural nucleic acid sequence of interest.

The term "heterologous gene", as used herein, means a gene encoding a protein, polypeptide, RNA, or a portion of any thereof, whose exact amino acid sequence is not normally found in the host cell, but is introduced by standard gene transfer techniques.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

The terms "identity" and "similarity", as used herein, and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (Computational Molecular Biology, Lesk, A. M., ed., Oxford University Press. New York (1988); Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinje, G., Academic Press (1987); and Sequence Analysis Primer, Gribskov, M. and Devereux, J., eds., M Stockton Press, New York (1991)). Methods commonly employed to determine identity or similarity between two sequences include, but are not limited to those disclosed in Carillo, H., and Lipman, D., SIAM J. Applied Math., 48 : 1073 (1988). Preferred methods to determine identity are designed to give the largest match between the two sequences tested. Methods to determine identity and similarity are codified in computer programs. Typical computer program methods to determine identity and similarity between two sequences include: GCG program package (Devereux, J., et al., Nucleic Acids Research 12 (1): 387 (1984)), BLASTP, BLASTN, FASTA and TFASTA (Atschul, S. F. et al., J. Mol. Biol. 215: 403 (1990)).

An "insertion" or "addition", as used herein, refers to a change in an amino acid or nucleotide sequence resulting in the addition of one or more amino acid or nucleotide residues, respectively, as compared to the naturally occurring molecule.

The term "modified expression", as used herein, means expression in a transgenic plant which is genetically engineered to have one or both of the 5' and 3' osmotin UTRs of the present invention flanking the respective regions of a heterologous structural gene of interest wherein the mRNA levels, protein levels or enzyme specific activity of the structural gene of interest have been altered relative to 1) a native version of the plant, or 2) a transgenic plant harboring the structural gene of interest but not including the one or both of the 5' and 3' osmotin UTRs as flanking regions thereof.

By "non-native phenotype", as used herein, it is meant a trait occurring, or influenced by, expression of recombinant DNA in a plant.

As used herein, the term "recombinant nucleic acid" refers to nucleic acid that has been derived or isolated from any source, that may be subsequently chemically altered, and later introduced into a transgenic plant. An example of recombinant nucleic acid "derived" from a source, would be a DNA or RNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

The term "stringency" is used herein to describe the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (for example, hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (for example, hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

The term "structural nucleic acid sequence of interest", as used herein, means a sequence of DNA, RNA or synthetic nucleotides that code for a protein. The term "structural nucleic acid of interest" is used interchangeably herein with the term "structural gene of interest".

As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

"Nucleic acid sequence", as used herein, refers to a polymer of nucleotides in which the 3' position of one nucleotide sugar is linked to the 5' position of the next by a phosphodiester bridge. In a linear nucleic acid strand, one end typically has a free 5' phosphate group, the other a free 3' hydroxyl group. Nucleic acid sequences may be used herein to refer to oligonucleotides, or polynucleotides, and fragments or portions thereof, and to DNA or RNA of genomic or synthetic origin that may be single- or double-stranded, and represent the sense or antisense strand.

A promoter nucleic acid sequence is said to be "operably linked" to a structural nucleic acid sequence of interest if the two are situated such that the promoter nucleic acid sequence influences the transcription of the structural nucleic acid sequence of interest. For example, if the structural nucleic acid sequence codes for the production of a protein, the promoter nucleic acid sequence would be operably linked to the structural nucleic acid sequence if the promoter nucleic acid sequence affects the expression of the protein product from the structural nucleic acid sequence.

"Transgenic plant", as used herein, refers to a plant that contains a foreign nucleotide sequence inserted into either its nuclear genome or organellar genome.

The term "derivative", as used herein, refers to a modification of the native nucleic acid sequence of a 5' and/or 3' tobacco osmotin UTR. Illustrative of such modifications with regard to a 3' tobacco osmotin UTR, would be the substitution, insertion, and/or deletion of one or more bases relating to a nucleic acid sequence of a 3' tobacco osmotin UTR that preserve, slightly alter, or increase the protective function of one or more stem loop structures of the 3' UTR against RNase degradation. Such derivatives can be readily determined by one skilled in the art, for example, using sequence information to determine inverted repeats and using computer modeling techniques for predicting and optimizing optimal and suboptimal secondary structures, examples of which are discussed herein. A derivative of a 5' tobacco osmotin UTR may, for example, comprise a substitution, insertion, and/or deletion of one or more bases relating to a nucleic acid sequence of a 5' tobacco osmotin UTR that a) increase the AT (or AU) content; b) provide an optimized nucleotide context surround the AUG codon of the 5' end of the gene of interest; and/or c) do not add secondary structures which inhibit the scanning process of 40S ribosomal subunits. The term "derivative" thus also includes nucleic acid sequences having substantial sequence homology with the specifically disclosed regulatory sequences, such that they are able to have the disclosed effect on expression.

Computer modeling techniques for use in predicting/evaluating 5' and 3' UTR derivatives of the present invention include, but are not limited to: MFold version 3.1 available from Genetics Corporation Group, Madison, Wis. (see Zucker et al., Algorithms and Thermodynamics for RNA Secondary Structure Prediction: A Practical Guide. In *RNA Biochemistry and Biotechnology*, 11-43, J. Barciszewski & B. F. C. Clark, eds., NATO ASI Series, Kluwer Academic Publishers, Dordrecht, N L, (1999); Zucker et al., *Expanded Sequence Dependence of Thermodynamic Parameters Improves Prediction of RNA Secondary Structure. J. Mol. Biol.* 288, 911-940 (1999); Zucker et al., RNA Secondary Structure Prediction. In *Current Protocols in Nucleic Acid Chemistry* S. Beaucage, D. E. Bergstrom, G. D. Glick, and R. A. Jones eds., John Wiley & Sons, New York, 11.2.1-11.2.10, (2000)), COVE (RNA structure analysis using covariance models (stochastic context free grammar methods)) v.2.4.2 (Eddy & Durbin, Nucl. Acids Res. 1994, 22: 2079-2088) which is freely distributed as source code and which can be downloaded from the internet, and FOLDALIGN, also freely distributed and available for downloading from the internet (see *Finding the most significant common sequence and structure motifs in a set of RNA sequences*. J. Gorodkin, L. J. Heyer and G. D. Stormo. Nucleic Acids Research, Vol. 25, no. 18 pp 3724-3732, 1997; *Finding Common Sequence and Structure Motifs in a set of RNA Sequences*. J. Gorodkin, L. J. Heyer, and G. D. Stormo. ISMB 5; 120-123, 1997).

Native, optimized, fragmented or otherwise modified versions of the 5' tobacco osmotin UTR may be used to flank the 5' region one or more structural genes of interest in a construct. The native sequence of the 5' tobacco osmotin UTR is as follows: tatccaacaacccaacttgttaaaaaaaatgtccaacaac (SEQ. ID No. 1). (Nelson et al., *Analysis of structure and transcriptional activity of an osmotin gene*. Plant Mol. Bio. 19:577-588 (1992)).

One skilled in the art will readily be able ascertain usable derivations of the native sequence. In one preferred embodiment, exemplified herein, the single "atg" codon has been modified to "att" such that 40S ribosomal subunits will not be hindered by the semblance of an initiation codon in the 5' UTR. According to this embodiment, the nucleic acid sequence of the native 5' tobacco osmotin UTR has been modified to

```
                                          (SEQ. ID No. 2)
tatccaacaacccaacttgttaaaaaaaatttccaacaac where the single base change is shown with
underlining.
```

Native, optimized, fragmented or otherwise modified versions of the 3' tobacco osmotin UTR may also be used to flank the 3' region of one or more structural genes of interest in a construct. The published native sequence of the 3' tobacco osmotin UTR is:

```
                                          (SEQ. ID No. 3)
agtggctatttctgtaataagatccacctttggtcaaatt attctatcgacacgttagtaagacaatctatttgactcgtt tttatagttacgtactttgtttgaagtgatcaagtcatgat
```

```
-continued
ctttgctgtaataaacctaagacctgaataagagtcacatat gtatttttgtcttgatgttatatagatcaataatgcatttgg attatcgttttttatattgtttttcttttgaagttttagtaaa gtcttaagctt.
```

(Nelson et al. (1992).

In most cases, sequences having 95% homology to the 5' and 3' tobacco osmotin UTR sequences specifically disclosed herein will function as equivalents, and in many cases considerably less homology, for example 75% or 80%, will be acceptable. Locating the parts of these sequences that are not critical may be time consuming, but is routine and well within the skill in the art.

To modify the subject 5' and 3' UTR sequences in accordance with the teachings of this invention, exemplary techniques include those for polynucleotide-mediated, site-directed mutagenesis as well as well known techniques for the use of restriction enzymes, PCR amplification and ligase to modify and/or join existing nucleic acid molecules. (See, e.g., Zoller et al., *DNA*, 3:479-488 (1984); Higuchi et al., *Nucl. Acids Res.*, 16:7351-7367 (1988); Ho et al., *Gene*, 77:51-59 (1989); Horton et al., *Gene*, 77:61 (1989); PCR Technology: Principles and Applications for DNA Amplification, (ed.) Erlich (1989); and U.S. Pat. No. 6,271,360 to Metz et al., *Single-stranded oligodeoxynucleotide mutational vectors* (issued Aug. 7, 2001)). In a preferred embodiment of the invention, one or more stem loop structures are added to SEQ. ID. No. 2 to provide further protection against mRNA degradation. In one aspect of this embodiment, the additional stem loop structures are derived through PCR amplification of all or part of SEQ. ID. No. 3. Stem loop structures may also be synthesized independently of SEQ. ID. No. 3. In a further embodiment of the invention, one or more existing stem loop structures within SEQ. ID. No. 3 are deleted, for example, by the use of site-specific restriction enzymes known to those skilled in the art.

Preferably, the 5' and 3' tobacco osmotin UTRs of the present invention are used in conjunction with one another with regard to flanking the appropriate regions of one or more structural genes of interest. The present invention, however, is not so limited. One or both of the 5' or 3' tobacco osmotin UTRs of the present invention may thus be used, for example, in conjunction with a UTR native to the structural gene(s) of interest, heterologous to the structural gene(s) of interest and the tobacco osmotin gene, or in addition to such a native or heterologous UTR.

The 5' and 3' osmotin UTRs for use in the present invention can be isolated from tobacco tissues or cells by means of nucleic acid hybridization techniques known in the art using, for example, the nucleotide sequences disclosed herein or portions thereof as hybridization probes. Such probes may consist of the entire osmotin gene or portions thereof, including the 5' and 3' UTRs identified herein. The subject osmotin 5' and 3' UTRs may also be synthetic and obtained using the above described sequences and nucleic acid synthesis techniques known in the art. Further, osmotin-encoding nucleotide sequences can be obtained from pOC cDNA clones as described by Singh et al., *Plant Physiol.* 90:1096-1101 (1989).

Other plants from which osmotin genes can be isolated are inter alia, millet, soybean cotton, tomato and potato, described by Singh et al (1987), and King et al., *Plant. Mol. Biol.* 10, 401-412 (1988). It is further contemplated that UTRs from genes encoding osmotin-like proteins from other plants than those mentioned above, such as maize, can be used in accordance with the present invention as can reasonably be expected to have similar homology to osmotin UTRs from tobacco.

The structural nucleic acid sequence of interest is operably linked to 5' and/or 3' UTR regions isolated or derived from an osmotin gene by known cloning techniques. The structural nucleic acid sequence of interest may be heterologous or homologous to the genes natively presently in the recipient plant, plant cell(s), or plant tissue. In either case, the 5' and 3' osmotin UTRs of the present invention are useful for regulating the translational efficiency of a nucleic acid sequence of interest so as to: increase the half-life of transcribed mRNA; and/or express the protein encoded by the structural nucleic acid sequence of interest in greater abundance in plant tissue than would be expressed without use of the 5' and/or 3' osmotin UTR(s) of the present invention. It is further specifically contemplated herein that the present invention is used in a gene construct engineered such that the protein encoded by the structural nucleic acid sequence of interest is expressed only in certain preferred tissue of a plant, such as the roots, leaves or stems, and not in the seed.

The present invention is generally applicable to the expression of structural genes of interest in both monocotyledonous and dicotyledonous plants. This invention is thus suitable for any member of the monocotyledonous (monocot) plant family including, but not limited to, maize, rice, barley, oats, wheat, sorghum, rye, sugarcane, pineapple, yams, onion, banana, coconut, and dates. A preferred application of the present invention is in the production of transgenic maize plants. Dicotyledonous (dicot) species for use with the present invention include, but are not limited to, tobacco, tomato, sunflower, cotton, sugarbeet, potato, lettuce, melon, soybean and canola (rapeseed).

The structural nucleic acid sequence of interest used in constructs of the present invention may be any nucleic acid sequence that provides for, or enhances, a beneficial feature of a resultant transgenic plant. Particularly useful nucleic acid sequences are those that encode proteins or antisense RNA transcripts in order to promote increased nutritional values, higher yields, tolerance to herbicides, insects, or diseases, and the like. More preferably, the nucleic acid sequences will be useful genes which are inherently unstable due to their relatively large size (at least 4-5 kb in length), which is known to render the genes more susceptible to physical, chemical, or enzymatic degradation. Genes inherently unstable due to their size include insecticidal genes from *Xenorhabdus* (see U.S. Pat. No. 6,048,838) and Photorabdus (e.g., Toxin A as discussed herein).

In one preferred embodiment of the present invention, one or more structural nucleic acids of interest are flanked by one or more osmotin UTRs of the present invention which have been "stacked" in relation to one another in a particular crop variety. By use of the terms "stacked" or "stacking", it is meant herein that multiple structural genes of interest, each structural gene of interest preferably conferring a commercially desirable trait, have been transgenically introduced into a single crop variety (inbred or hybrid). For example, a corn hybrid with stacked genes might contain genes for the insect resistance (e.g., Cry1F B.t. genes) as well as herbicide resistance genes (e.g., glyphosate resistance genes).

In another preferred embodiment, one or more of the osmotin UTRs of the present invention are functionally linked to a Toxin A gene from Photorabdus, which is then stacked with one or more insecticide and/or herbicide resistance genes in a single crop variety. Preferably, but not necessarily, the insecticide gene(s) will be from a *Bacillus thuringiensis* or *Xenorhabdus* spp., and the herbicide gene(s) will be one or more of a glufosinate, glyphosate, imidazolinone, or 2.4-D or sulfonyl urea resistance genes. Of course, any of the "stacked" insecticide or herbicide genes may be functionally linked to the osmotin UTRs of the present invention.

The structural nucleic acid sequence of interest may be derived in whole or in part from a bacterial genome or episome, eukaryotic genomic, mitochondrial or plastid DNA, cDNA, viral nucleic acid, or chemically synthesized nucleic acid. It is contemplated that the structural nucleic acid sequence of interest may contain one or more modifications in either the coding region which could affect the biological activity or the chemical structure of the expression product, the rate of expression, or the manner of expression control. Such modifications include, but are not limited to, mutations, insertions, deletions, rearrangements and substitutions of one or more nucleotides. The structural nucleic acid sequence of interest may constitute an uninterrupted coding sequence or it may include one or more introns, bounded by the appropriate plant-functional splice junctions. The structural nucleic acid sequence of interest may be a composite of segments derived from a plurality of sources, naturally occurring or synthetic. The structural nucleic acid sequence of interest may also encode a fusion protein, so long as the experimental manipulations maintain functionality in the joining of the coding sequences.

In carrying out the present invention, cloning techniques are employed so as to obtain a vector containing the 5' and/or 3' osmotin UTRs flanking the structural gene of interest for subsequent introduction into desired host cells. The 5' and 3' osmotin UTRs, structural nucleic acid sequence of interest, and any desired promoters, enhancers, selectable markers, etc. may thus be isolated and cloned into vectors using standard cloning procedures in the art, such as those described by J. Sambrook et al., *Molecular Cloning: A Laboratory Manual*, Cold Spring Harbor Laboratory Press (2d ed., 1989), and Ausubel, F. M. et al. (1989) *Current Protocols in Molecular Biology*, John Wiley & Sons, New York, N.Y. both of which are hereby incorporated by reference.

A wide variety of cloning vectors are available, or can be prepared, where the cloning vector includes a gene construct functional in a desired plant species. Illustrative vectors include, for example, pBR322, pUC series, pACYC184, Bluescript series (Stratagene), and the like. Such vectors are thus commercially available or can be readily prepared for transformation of plant cells. In general, plasmid or viral vectors will contain nucleic acid sequences necessary for both maintenance and expression of a heterologous DNA sequence in a given host. Selection of appropriate elements to optimize expression in any particular species is a matter of ordinary skill in the art utilizing the teachings of this disclosure. Suitable DNA components, selectable marker genes, reporter genes, enhancers, introns, and the like are described by K. Weising et al., *Ann. Rev. Genetics*, 22, 421 (1988).

Typically, the structural nucleic acid sequence of interest and 5' and/or 3' tobacco osmotin UTRs are inserted into an appropriate cloning vector at appropriate restriction site(s) such that the structural gene of interest is operably linked to a desired promoter and the 5' and/or 3' tobacco osmotin UTRs are functionally linked to the structural nucleic acid sequence of interest. In preparing the gene constructs of this invention, the various nucleic acid fragments may be manipulated, so as to provide for the nucleic acid sequences in the proper orientation and, as appropriate, in the proper reading frame. Of course, adapters or linkers may be employed for joining nucleic acid fragments or other manipulations may be involved to provide for convenient restriction sites, removal of superfluous DNA, removal of restriction sites, or the like.

The expression of structural genes employed in the present invention may be driven by any number of promoters. Although the endogenous promoter of a structural gene of interest may be utilized herein for transcriptional regulation of the gene, preferably, the promoter is a foreign regulatory sequence. For plant expression vectors, suitable viral promoters include the Cassaya Vein Mosaic Virus promoter (Verdaguer et al., *Plant Mol. Biol.* 31(6):1129-39 (1996); 35S RNA and 19S RNA promoters of Cauliflower Mosaic Virus (CaMV) (Brisson et al., *Nature* 310:511 (1984); Odell et al., *Nature,* 313:810 (1985); the enhanced and double enhanced CaMV35S promoter (Kay et al., *Science* 236:1299-1302 (1987); the full-length transcript promoter from Figwort Mosaic Virus (FMV) (Gowda et al., *J. Cell Biochem.,* 13D: 301, 1989) and the coat protein promoter from TMV (Takamatsu et al., *EMBO J.* 6:307, 1987). Other useful promoters include the light-inducible promoter from the small subunit ribulose 1,5-bisphosphate carboxylase oxygenase (ss-RUBISCO) (Coruzzi et al., *EMBO J.,* 3:1671 (1984); Broglie, et al., *Science* 224:838 (1984); rice actin promoter (McElroy et al., *Plant Cell.* 2(2):163-71 (1990); and Adh1 promoter (Dennis et al., *Nucleic Acids Res.* 12(9):3983-4000 (1984)); mannopine synthase promoter (Velten et al., *EMBO J.,* 3:2723, 1984); nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., *Mol. Cell. Biol.* 6:559 (1986); Severin et al., *Plant Mol. Biol.* 15:827, (1990)).

Analysis of the cloning steps are typically conducted and may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Once the cloning steps have been completed, various techniques exist which allow for the introduction, plant regeneration, stable integration, and expression of foreign recombinant vectors containing heterologous genes of interest in plant cells. One such technique involves acceleration of microparticles coated with genetic material directly into plant cells (U.S. Pat. No. 4,945,050 to Cornell; U.S. Pat. No. 5,141,131 to DowElanco; and U.S. Pat. Nos. 5,538,877 and 5,538,880, both to Dekalb). This technique is commonly referred to as "microparticle bombardment" or "biolistics". Plants may also be transformed using *Agrobacterium* technology (U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149, 645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba-Geigy, U.S. Pat. Nos. 5,463,174 and 4,762,785 both to Calgene, and U.S. Pat. Nos. 5,004,863 and 5,159,135 both to Agracetus). Another transformation method involves the use of elongated needle-like microfibers or "whiskers" to transform maize cell suspension cultures (U.S. Pat. Nos. 5,302,523 and 5,464,765 both to Zeneca). In addition, electroporation technology has been used to transform plant cells from which fertile plants have been obtained (WO 87/06614 to Boyce Thompson Institute; U.S. Pat. Nos. 5,472,869 and 5,384,253 both to Dekalb;

U.S. Pat. Nos. 5,679,558, 5,641,664, WO9209696 and WO9321335 to Plant Genetic Systems).

Still further techniques for the transformation of plant cells include: direct DNA uptake mechanisms (see Mandel and Higa, *J. Mol. Biol.,* 53:159-162 (1972); Dityatkin et al., *Biochimica et Biophysica Acta,* 281:319-323 (1972); Wigler et al., *Cell,* 16:77 (1979); and Uchimiya et al., In: Proc. *5th Intl. Cong. Plant Tissue and Cell Culture,* A. Fujiwara (ed.), Jap. Assoc. for Plant Tissue Culture, Tokyo, pp. 507-508 (1982)); fusion mechanisms (see Uchidaz et al., In: *Introduction of Macromolecules Into Viable Mammalian Cells,* Baserga et al. (eds.) Wistar Symposium Series, 1:169-185 (1980)); site specific recombination (see WO/9109957), and various infectious agents (see Fraley et al., *CRC Crit Rev. Plant Sci.,* 4: 1-46 (1986); and Anderson, *Science,* 226:401-409 (1984)).

The appropriate procedure to transform a selected plant cell may be chosen in accordance with the plant cell used. Based on the experience to date, there appears to be little difference in the expression of genes, once inserted into cells, attributable to the method of transformation itself. Rather, the activity of the foreign gene inserted into plant cells is dependent upon the influence of endogenous plant DNA adjacent the insert. Generally, the insertion of heterologous genes appears to be random using any transformation technique; however, technology currently exists for producing plants with site specific recombination of DNA into plants cells (see WO91/09957.

The particular methods used to transform such plant cells are not critical to this invention, nor are subsequent steps, such as regeneration of such plant cells, as necessary. Any method or combination of methods resulting in the expression of the desired sequence or sequences under the regulatory control of one or more of the subject 5' and/or 3' UTRs is acceptable.

Once introduced into the plant tissue, the expression of the structural gene may be assayed in a transient expression system, or it may be determined after selection for stable integration within the plant genome.

Any number of selection systems may be used to recover transformed cell lines. These include, but are not limited to, the herpes simplex virus thymidine kinase (Wigler et al., *Cell* 11:223 (1977)) and adenine phosphoribosyltransferase (Lowy et al., *Cell* 22:817 (1980)) genes that can be employed in tk⁻ or aprt⁻ cells, respectively. Also, antimetabolite, antibiotic, or herbicide resistance can be used as the basis for selection; for example, dhfr, which confers resistance to methotrexate (Wigler et al., *Proc. Natl. Acad. Sci.,* 77:3567 (1980)); npt, which confers resistance to the aminoglycosides neomycin and G-418 (Colbere-Garapin et al., *J. Mol. Biol.,* 150:1)(1981)); and ALS (U.S. Pat. No. 5,378,824 to Bedbrook) or PAT (Wehrmann et al., *Nat Biotechnol* 14(10): 1274-8 (1996)), which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan, *Proc. Natl. Acad. Sci.,* 85:8047 (1988)). More recently, the use of visible markers has gained popularity with such markers as GFP, anthocyanins, α-glucuronidase and its substrate GUS, luciferase and its substrate luciferin, being widely used not only to identify transformants, but also to quantify the amount of transient or stable protein expression attributable to a specific vector system (Rhodes et al., *Methods Mol. Biol.,* 55:121 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences encoding the polypeptide can be identified by the absence of marker gene function. Alternatively, a marker gene can be placed in tandem with a sequence encoding the polypeptide under the control of a single promoter. Expression of the marker gene in response to induction or selection usually indicates expression of the tandem gene as well.

Alternatively, host cells that contain the nucleic acid sequence encoding the polypeptide of interest (for example, a polypeptide encoded by a nucleic acid of the present invention) and express the polypeptide may be identified by a variety of procedures known to those of skill in the art. These procedures include, but are not limited to, DNA-DNA or DNA-RNA hybridizations and protein bioassay or immunoassay techniques that include membrane, solution, or chip based technologies for the detection and/or quantification of nucleic acid or protein.

The presence of polynucleotide sequences encoding a polypeptide of interest (for example, a polypeptide encoded by a nucleic acid of the present invention) can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences encoding the polypeptide to detect transformants containing DNA or RNA encoding the polypeptide. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, that can be used as a probe or amplimer.

A variety of protocols for detecting and measuring the expression of a polypeptide (for example, a polypeptide encoded by a nucleic acid of the present invention), using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al., *Serological Methods, a Laboratory Manual,* APS Press, St Paul, Minn. (1990), and Maddox et al., *J. Exp. Med.,* 158:1211 (1983).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, that may be used, include radionuclides, enzymes, fluorescent, chemiluminescent, or chromogenic agents as well as substrates, cofactors, inhibitors, magnetic particles, and the like.

Figure 8:
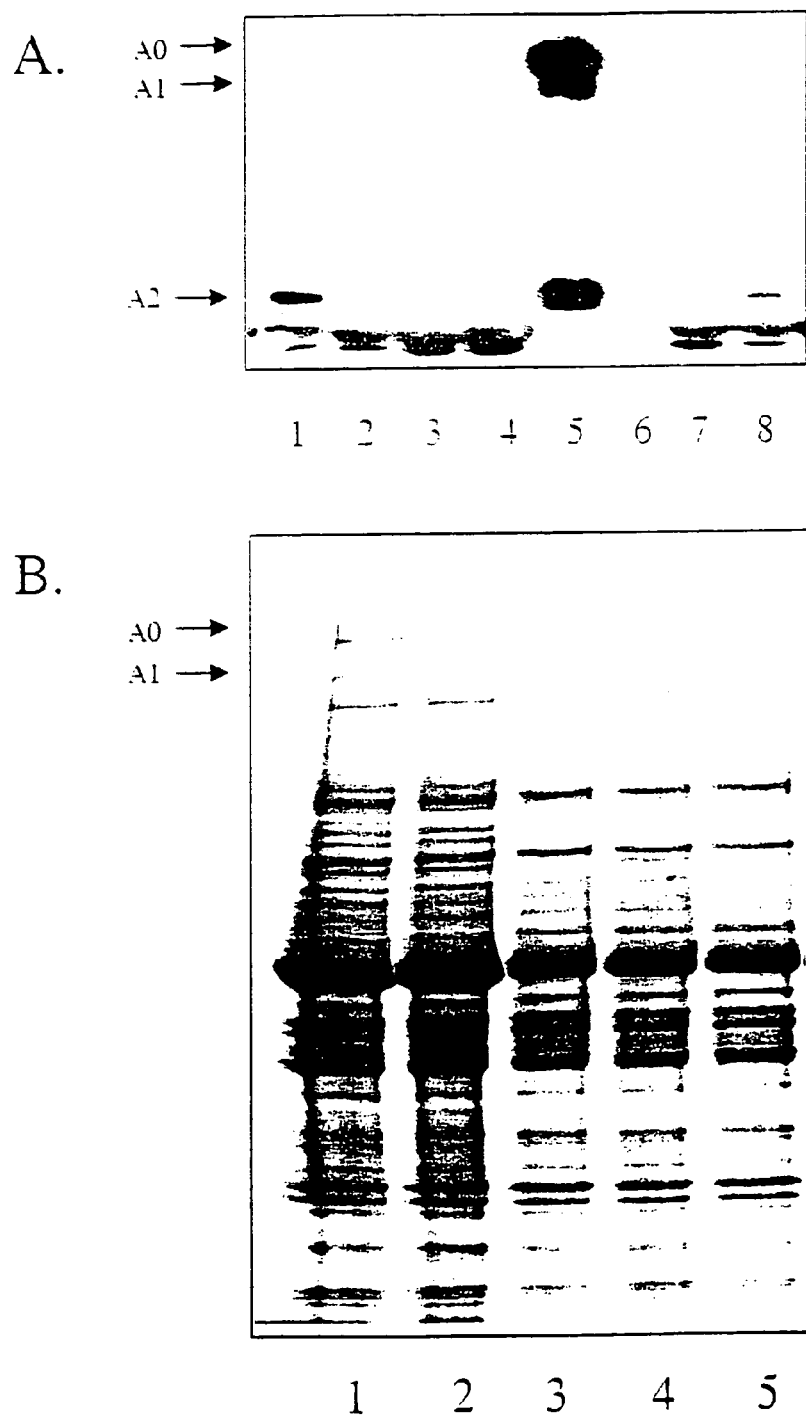
FIG. 8 provides an analysis of Toxin A expression of transgenic *Arabidopsis* plants: (A) Western blot analysis of A2 protein expression in transgenic plants with construct pDAB7028. Lanes 1-4, and Lanes 6-8: transgenic plants; Lane 5: recombinant *E. coli* strain. (B) SDS-PAGE gel analysis of Toxin A expression in transgenic plants with construct pDAB7026. Lane 1: high expresser of Toxin A gene; Lanes 2-4: three low expressers of Toxin A gene; Lane 5: Transgenic plants with GUS gene construct. The positions of A0 and A1 proteins are indicated by arrows. Ten ug of total leaf protein were loaded into each lane.

Techniques are known for the in vitro culture of plant tissue, and, in a number of cases, for regeneration into whole plants. The appropriate procedure to produce mature transgenic plants may be chosen in accordance with the plant species used. Regeneration varies from species to species of plants. Efficient regeneration will depend upon the medium, on the genotype, and on the history of the culture. Once whole plants have been obtained, they can be sexually or clonally reproduced in such a manner that at least one copy of the sequence is present in the cells of the progeny. Seed from the regenerated plants can be collected for future use, and plants grown from this seed. Procedures for transferring the introduced gene from the originally transformed plant into commercially useful cultivars are known to those skilled in the art.

Particular embodiments of this invention are further exemplified in the Examples. However, those skilled in the art will readily appreciate that the specific experiments detailed are only illustrative of the invention as described more fully in the claims which follow thereafter.

The preferred gene of interest for use in the present invention is the Toxin A gene from *Photorabadus luminescens* (hereinafter "*Photorabadus*" or "*p. luminescens*").

EXAMPLES

Experimental Design

*Photorhabdus luminescens* is a gram-negative bacterium that forms entomopathogenic symbioses with *Heterorhabditis* spp. soil nematodes. (ffrench-Constant et al., *Cell Mol Life Sci* 57(5):828-33 (2000); ffrench-Constant et al. *Curr Opin Microbiol.* 2(3):284-8 (1999)). Nematodes harboring this bacterium have long been used as biological control agents for insect infestation. After the nematode invades the insect host, the bacteria are released into the insect haemocoel where they produce toxins and proteases that kill the insect host and render the host cadaver into a ready source of nutrients for both bacteria and nematode growth.

Several groups of toxin complexes have been purified from *P. luminescens* and their corresponding genes have been cloned. (Bowen et al., *Science* 280:2129-32 (1998); Merlo et al., GenBank Accession No. AF188483 (1999)). In previously conducted work, it was found that the fermentation broth of *P. luminescens* strain W-14 contains at least two potent proteins, Toxin A and Toxin B, which independently contribute to the insecticidal activity against Southern corn rootworm (SCR; *Diabrotica undecimpunctata howardi*) and tobacco hornworm (THW; *Manduca sexta*). (Gou et al., *J. Biol. Chem.* 274(14):9836-42 (1999)). The activities of these two proteins differ dramatically in toploaded artificial diet assays. $LD_{50}$ values (lethal dose for 50% of insects) against SCR are 5 ng/$cm^2$ diet and 87 ng/$cm^2$ diet for Toxin A and Toxin B, respectively.

The 283 kD Toxin A protein (SEQ. ED. No. 4) (designated A0 protein herein) of *P. luminescens* strain W-14 is encoded by a single open reading frame (designated tcdA) of 7548 bp. (GenBank Accession No. AF188483; Gou, 1999). In the bacterial fermentation broth, native Toxin A exists in a large complex (>860 kD) consistent in size with a homotetramer (Verdaguer et al., *Plant Mol. Biol.* 31 (6):1129-39 (1996)). Isolation and characterization (N-terminal sequencing and MALDI-TOF/QTOF analyses) of the proteins comprising the Toxin A complex revealed that the N-terminal 88 amino acids of the A0 primary gene product are removed, and the remaining peptide is cleaved into two large polypeptides, designated A1 (5.8 kb) and A2 (1.7 kb) herein. During this processing step, another 88 internal amino acids are lost. (See FIG. 1). The order of these cleavage steps, and the significance of the N-terminal and internal deletions relative to toxin activity are believed to be unknown in the art at the time of this disclosures. It has also previously been unclear as to whether the A1 polypeptide alone is responsible for the insecticidal activity of Toxin A.

To assess the potential use of various forms of the Toxin A gene for pest control, its insecticidal activity was tested in transgenic *Arabidopsis* plants as follows.

Six plant transformation vectors (pDAB7031-pDAB7036) were constructed which contained various forms of the Toxin A gene under the control of a constitutive Cassaya Vein Mosaic Virus promoter (CsVMV). (See FIG. 2). These Toxin A gene fragments included: 1) full-length A0 gene (A0, 7.5 kb) (SEQ. ID. No. 5) in construct pDAB7031, 2) A0 gene with N-terminal truncation (A0/ΔN, 7.3 kb) (SEQ. ID. No. 6) in construct pDAB7032, 3) full-length A1 gene (A1, 5.8 kb) (SEQ. ID. No. 7) in construct pDAB7033, 4) A1 gene with C-terminal truncation (A1/ΔC, 5.6 kb) (SEQ. ID. No. 8) in construct pDAB7034, 5) A1 gene with both N- and C-terminal truncations (A1/ΔN+ΔC, 5.4) (SEQ. ID. No. 9) in construct pDAB7035, and 6) full-length A2 gene (A2, 1.7 kb) (SEQ. ID. No. 10) in construct pDAB7036. These six constructs were transformed into *Arabidopsis* plants via *Agrobacterium*-mediated transformation. Transgenic plants were selected based on the phenotype of kanamycin resistance.

As a strategy to enhance the expression of Toxin A in plant cells, additional gene constructs were also engineered such that three of Toxin A gene fragments A0 (SEQ. ID. No. 5), A1/ΔC (SEQ. ID. No. 8), and A2 (SEQ. ID. No. 10) were flanked on respective ends by 5' and 3' UTR sequences (SEQ. ID. Nos. 2 and 3, respectively) isolated from a tobacco osmotin gene. The resulting constructs were designated pDAB7026, in pDAB7027, pDAB7028, respectively (see FIG. 7). The protein expression levels of pDAB7026, pDAB7027 and pDAB7028 (hereinafter, the "osmotin UTR-Toxin A constructs") were then compared with Toxin A constructs not containing the osmotin UTRS—pDAB7031 through pDAB7036 (see FIG. 2) (hereinafter, the "non-osmotin UTR-Toxin A constructs").

Plasmid Construction

Unless otherwise noted herein, standard methods of DNA purification, restriction enzyme digestion, agarose gel analysis, DNA fragment isolation, ligation and transformation may be used as described in Sambrook et al., *Molecular Cloning: A Laboratory Manual*, Cold Spring Harbor Laboratory Press (2d ed., 1989)) and Ausubel et al., *Current Protocols in Molecular Biology* (New York: John Wiley and Sons) (1987).

The 7548 bp DNA sequence of the native Toxin A gene ORF used in this work was determined from a gene cloned in this laboratory from *P. luminescens* strain W-14. (GenBank Accession No. AF188483). An alanine codon was added at the second position of the ORF to accommodate an Nco I recognition site spanning the start codon. The resulting nucleic acid sequence, which coded for essentially the same protein, was subsequently designed according to parameters outlined in Adang et al., *Plant Mol. Biol.* 21 (1993). Synthesis of gene fragments and assembly into an intact coding region were performed by Operon Technologies (Alameda, Calif.). Rebuilding of the Toxin A gene removed putative RNA instability sequences (ATTTAA), potential intron splice signals, and potential polyadenylation signal sequences, and adjusted codon usage to accommodate expression in both monocot and dicot plant species ("plant optimized") (see PCT Application WO 01/11029, hereby incorporated by reference herein in its entirety). Unique Nco I and Sac I sites were added to the 5' and 3' ends of the coding region, respectfully. Various gene derivatives with corresponding Nco I and Sac I sites were generated from the basic tcdA coding region using PCR methods: A0/ΔN gene (SEQ ID. No. 6), A1 gene (SEQ ID. No. 7), A1/ΔC gene (SEQ ID. No. 8), A1/ΔN+ΔC gene (SEQ ID. No. 9) and A2 gene (SEQ ID. No. 10). All Toxin A gene fragments were thus placed under the expression control of the CsVMV promoter and a 3'UTR/polyadenylation signal sequence derived from the intergenic region between ORFs25/26 of Ti plasmid pTi-15955 (Barker et al., *Plant Mol. Biol.* 2, 335 (1983)). Each Toxin A gene expression cassette was excised (Asc I and Pme I) and cloned between the T-DNA borders on binary vector PDAB1542 (FIG. 12), which contains a kanamycin resistance gene as selectable marker for plant transformation. The resultant constructs (pDAB7031 through pDAB7036) are further described herein and diagrammed in FIG. 2.

A control plant transformation vector (pDAB7029) containing a CsVMV-GUS-ORF25 expression cassette (Jefferson, *Plant Molec. Biol. Rep.* 5, 387 (1987)) was constructed using the same strategy. The GUS gene was first excised from plasmid pKA882 (FIG. 13) by Nco I and Sac I enzymes and inserted in the place of the PAT gene in plasmid pDAB7013 (FIG. 14). The CsVMV-GUS-ORF25 cassette was then moved into binary vector pDAB1542 (FIG. 12) using enzymes Asc I and Pme 1.

To generate osmotin-Toxin A gene constructs, a pair of complementary oligonucleotides encoding the 40 bp 5' UTR sequence of a tobacco osmotin gene (SEQ. ID No. 1) was chemically synthesized according to the published sequence (Nelson et al., 1992) except for a modification which changed a single "atg" codon to "att" so as to remove a putative initiation codon from the 5' UTR sequence (resulting in SEQ. ID No. 2). During the synthesis, Bgl II and Nco I sites were added to 5' and 3' ends. The resulting 5' UTR sequence was then inserted into the same site between CsVMV promoter and PAT gene in vector pDAB7013 (FIG. 14), resulting in plasmid pDAB7020 (FIG. 15). The 3' UTR sequences of the same tobacco osmotin gene (SEQ. ID No. 3) were PCR amplified from an osmotin cDNA clone (Liu et al., *Proc. Natl. Acad. Sci. U.S.A.* 91:1888-1892 (1994); a kind gift from Dr. Ray Bressan, Purdue University). During the PCR amplification, Sac I and Xho I sites were added to the 5' and 3' ends, respectively. The amplified osmotin 3' UTR sequence (SEQ. ID. No. 3) was then used to replace the ORF25/26 3' sequence on pDAB6001 (FIG. 16, giving rise to plasmid pDAB7002 (FIG. 17). The PAT gene and osmotin 3' UTR were the excised from pDAB7002 with Nco I and Xho I and used to replaced the GUS gene on pDAB7020, resulting plasmid pDAB7021 (FIG. 18), which contains CsVMV-OSM (osmotin) 5' UTR/PAT/OSM 3' UTR-ORF25/26 expression cassette. The coding regions of three Toxin A gene fragments, A0 (SEQ. ID. No. 5), A1/ΔC (SEQ. ID. No. 5), A1/ΔC (SEQ. ID. No. 8), and A2 (SEQ. ID. No. 10), were then used to replace the PAT gene on pDAB7021 (FIG. 18). Finally, the expression cassettes containing the modified coding region fragments under control of the CxVMV promoter and ORF25/26 3' UTR were cloned separately into binary vector pDAB1542 (FIG. 12).

A map of a plant transformation vector containing the full-length A0 gene with ostmotin 5' and 3' UTR (pDAB7026) is shown in FIG. 19. Using a similar strategy, a control plant transformation vector containing CsVMV-OSM 5'UTR/GUS/OSM 3'UTR-ORF 25/26 was also constructed.

In addition to the vector embodiments described above, one of skill in the art will recognize that a generic vector can readily be created which will allow any gene of interest to be cloned adjacent the 5' and 3' tobacco osmotin UTSs of the present invention. As a non-limiting example, the plant expression vector pBI121 (Clontech Laboratories, Palo Alto, Calif.) contains an expression cassette of the GUS reporter gene driven by a CaMV 35S promoter and terminated by NOS terminator. (Jefferson, *Nature* 342:837-838, 1989). There are three restriction sites, Xba I, BamH I, and Sma I, between the CaMV 35S promoter and GUS reporter gene. Vector pBI121 also has a Sst I site between the GUS gene and its NOS terminator sequence. A 5' osmotin UTR sequence of the present invention may be chemically synthesized with Xba I and BamH I sites on its 5' and 3' ends using standard techniques, and then readily inserted into the Xba I and BamH I sites on pBI121. To insert the osmotin 3' UTR sequence into vector pBI121, PCR amplification procedures can be used to isolate the osmotin 3' UTR from osmotin cDNA cone with the addition of Sma I and Sst I sites to its 5' and 3' ends. This osmotin 3'UTR sequence then can be inserted into the Sma I and Sst I sites on pBI121, which will replace the GUS coding region. This cloning step creates an expression cassette of CaMV 35S-OSM 5'UTR/OSM 3'UTR-NOS on the resultant plasmid. In this expression cassette, there will be two restriction sites, BamHI and SmaI, between osmotin 5' UTR and 3' UTR sequence. Thus, using BamH I and Sma I restriction enzymes and the appropriate restriction sites on the gene of interest, an gene of interest may be cloned into pBI121 for expression in transgenic plants.

Plant Growth and Transformation

*Arabidopsis* plants (Columbia ecotype) were grown at 22° C. with a lighting cycle of 16 hours light and 8 hours dark. All plant transformation constructs were transformed into *Agrobacterium* strain C58 (Z707) (ATCC 33970) using either electroporation (Mattanovich et al., Efficient transformation of *Agrobacterium* spp. by electroporation. *Nucleic Acids Research* 17(16) pp 6747 (1989); Mersereau et al., Efficient transformation of *Agrobacterium tumefaciens* by electroporation. *Gene* (90) pps 149-151 (1990)) or freeze-thaw methods (Hofgen and Willmitzer, Storage of competent cells for *Agrobacterium* transformation. *Nucleic Acids Research,* 16:9877 (1998). Plant transformations were performed using the vacuum infiltration method (Bechtold et al., *Mol. Biol. Genet.* 316: 1194-1199 (1993)). Transgenic plants were selected based on the phenotype of kanamycin resistance.

Northern Hybridization

Total RNA was extracted from 150 mg mature leaf tissues using RNeasy Mini Plant Kit (QIAGEN, Inc, Valencia, Calif.). For RNA blot analysis, 5 ug of total RNA was loaded onto 1.5% agarose gels containing formaldehyde and processed for Northern analysis. Hybridizations were performed at 42° for 4 hours in a UL TRAhyb solution (Ambion, Inc., Austin, Tex.). After hybridization, membranes were washed twice with 2×SSPE, 0.5% SDS for 15 min, then twice with 0.1×SSPE, 0.1% SDS. The first three washes were at room temperature, and the final wash was at 42° C.

Bioassay of Transgenic Plants Against THW

Tobacco hornworm (THW, *Manduca sexta*) eggs were received from the North Carolina State University insectary. Eggs were incubated in lighted chambers (Percival, Boone, Iowa) at 22° or 28° C. for 2 to 3 days in 90 mm Petri dishes with agar solution. The morning of the bioassay, any larvae that hatched overnight were removed from the plates, and only fresh larvae were used in the bioassay (less than 6 hours old, preferably). 128-well CD International (Pitman, N.J.) bioassay trays were prepared by placing 0.5 ml of a 2% agar solution into each well. *Arabidopsis* leaves were taken from 5-week-old plants. For each plant, leaf tissues were distributed evenly among 8 wells. A single neonate hornworm larva was placed into each well. Wells were covered with perforated sticky lids and the insects were allowed to feed for three days (72 hr) in a chamber at 28° C. and 16:8 light:dark cycle. After 72 hours, insect mortality and weight scores were recorded. Mortality index was determined from the number of dead larvae out of the total number for any given plant. Two control (GUS) plants were used for every 16 transgenic plants with the Toxin A gene construct. Data analysis was performed on insect mortality scores by comparing the percent insect mortality on experimental versus control plants. Mortality scores were transformed and a z-test was used. Plants that showed "moderate to high" Toxin A protein levels and significantly higher mortality than the controls (at p=0.05) were considered "active." If the Toxin A protein level was low, but mortality was high (usually >50%), plants were re-tested (usually in the next generation, but the original plant may be re-sampled). To reveal any potential growth inhibition effects, individual insect weights were analyzed by ANOVA, comparing transformed plants with controls.

Experimental Results

Non-Osmotin UTR-Toxin A Constructs

Northern hybridization experiments indicated that 67% of the $T_0$ plants examined (43 of 64) showed a single Toxin A RNA species of the expected size (FIG. 2). So far as we are aware, the full-length tcdA transcript is the largest transgenic RNA produced in plants to date. RNA expression levels varied from line to line (data not shown). Immunoblot (western) analysis was performed to examine the protein expression patterns in plants for each construct. Purified Toxin A protein produced from a recombinant *E. coil* strain, which exhibited three bands (A0, A1/ΔC, and A2 proteins) on SDS-PAGE gel, was used as a positive standard. Plants transformed with the CsVMV-GUS-ORF25 construct (pDAB7029) served as the negative control. The results (FIGS. 3A and 3B) showed that plants carrying construct pDAB7031 (full-length tcdA) (FIG. 20) produced three protein bands which aligned with the positive control (FIG. 3A). In pDAB7036 plants, only a single protein band was observed, whose molecular weight was slightly smaller than the full-length A0 protein due to the N-terminal truncation of 88 amino acids (FIG. 3B). The absence of detectable A1/ΔC, and A2 proteins suggests that the 88 amino acids at the N-terminus of the A0 protein act as a control signal for internal processing between the two large subunits. From plants carrying the three A1 gene constructs, single A1 protein bands with the expected molecular sizes were found (FIG. 3C). The A1 protein in pDAB7035 plants was the same size as that of the standard (FIG. 3A), while A1 proteins from pDAB7033 and pDAB7034 plants had slightly smaller sizes due to the truncations at the C-terminus or both ends (FIGS. 5B and 5C). In contrast, no A2 protein was detected in 32 examined plants transformed with construct pDAB7032 (data not shown), even though A2 RNA was properly produced (FIG. 2). These results suggest that either the translation efficiency of A2 RNA is extremely low, the A2 protein is very unstable in plants, or the A2 protein is not extracted by the methodology used.

Protein accumulation levels were further quantified for each primary transformant using an ELISA procedure (FIG. 28—Table 1). For construct pDAB7031 (FIG. 20), all the positive lines except lines 7031-43 and 7031-25 contained Toxin A protein at levels lower than 200 ppm (parts per million; in this work, 1,000 ppm is equal to 0.1% of total extractable protein).

The $T_1$ selfed progeny from three pDAB7031 lines (7031-043, 025, and 041) were tested for Toxin A protein accumulation and for resistance to THW feeding. All progeny analyzed in this work were pre-selected on kanamycin-containing medium to ensure the presence of transgenes. Parents of these three lines had shown Toxin A protein levels of 1056, 349, and 134 ppm, respectively, at the $T_0$ generation. However, none of the progeny from lines 7031-025 and 7031-041 produced Toxin A protein. For line 7031-043, 9 out of 32 progeny showed very low levels of Toxin A protein (<80 ppm); none of the others showed detectable Toxin A. Apparently, Toxin A gene expression was silenced in these progeny plants. As a consequence, none of these plants showed resistance to THW (data not shown).

These data prompted a larger scale examination of primary transformants ($T_0$ plants) for insecticidal activity and Toxin A accretion levels. For this purpose, another 280 transgenic lines were generated with construct pDAB7031 (FIG. 20). Among these 280 transformants, only one line (7031-240) showed significantly high insecticidal activity (100% insect mortality) (FIG. 29—Table 2). This plant had a Toxin A protein level of 788 ppm, and was the highest expresser among these 280 lines. Toxin A protein production and insect activity of 32 of its $T_1$ progeny were determined. The results showed that 11 progeny had undetectable levels of Toxin A protein and insecticidal activity, while the other 21 plants retained the high to very high levels of Toxin A protein production (739-7023 ppm) and showed 100% insect mortality. Insect mortality for the control plants transformed with construct CsVMV-GUS-ORF25 was 18.7%.

The above results indicated that when Toxin A accumulation reached a threshold level in plants (about 700 ppm), it could confer complete resistance to THW. However, it was noticed that the frequency of recovering insect-resistant lines was very low (1 out of 340 or 0.3%). This was probably due to the overall low expression of the large Toxin A gene from transformation vector pDAB7031 (FIG. 20), even though a strong constitutive promoter was used.

Osmotin UTR-Toxin A Constructs

To enhance expression of the Toxin A gene in plants, new constructs were produced by adding 5' and 3' UTR sequences (SEQ. ID. Nos. 2 and 3) from a tobacco osmotin gene to the corresponding ends of the Toxin A coding regions as described herein. To determine if these osmotin UTR structural elements would improve Toxin A gene expression levels, their effects were tested in three Toxin A gene constructs: pDAB7026 (full-length A0 gene) (SEQ. ID. No. 5), pDAB7027 (A1/ΔC gene) (SEQ. ID. No. 8), and pDAB7028 (A2 gene) (SEQ. ID. No. 10). (See FIG. 7).

RNA expression patterns were examined in transgenic plants transformed with these three osmotin-Toxin A gene constructs. Northern blot analyses indicated 20 out of 30 examined plants, which covered all three constructs, showed a single species of Toxin A RNA with the expected molecular size (data not shown). These results were therefore the same as those observed from analogous non-osmotin UTR-Toxin A constructs. Toxin A protein levels of these osmotin-Toxin A constructs were compared with their nonosmotin-Toxin A counterparts (FIG. 29—Table 2). Of 340 total pDAB7031 plants, only 23% had detectable levels of Toxin A protein, and the average Toxin A accumulation level of expressing plants was 67 ppm. For the 273 pDAB7026 transgenic plants, 39% contained Toxin A protein, and the average level of the expressing plants was 390 ppm. Therefore, there was about a 6-fold difference between these two constructs. If all plants examined were included in the statistical analysis (i.e. expressers and non-expressers), the average Toxin A production levels were 15 ppm for the pDAB7031 plants, and 150 ppm for the pDAB7026 plants (10-fold difference). In addition to an increase in overall Toxin A producers and Toxin A accumulation, there was a also difference in the number of high expressers (Toxin A protein >700 ppm) for each construct. Among the pDAB7031 plants, there were 2 high expressers (0.6%), whereas in the pDAB7026 plant group, there were 13 high expressers (4.7%). For some high expressers with construct pDAB7026 (>2,000 ppm), the accumulation of Toxin A protein in plant cells could be easily observed in an SDS-PAGE gel (FIG. 8B).

For plants carrying construct pDAB7033, 58% produced the truncated A1 proteins, and the average A1 protein level of expressing plants was 251 ppm. For pDAB7028 transgenic plants, 90% of examined plants showed A1 protein, and the average level of accumulation was 1131 ppm (4.5-fold increase). The effect of the osmotin flanking sequences was also observed in transgenic plants carrying constructs designed to produce the A2 protein. There was no detectable A2 protein in any of the 32 pDAB7032 plants examined (Table 1). However, in the 25 plants carrying construct pDAB7028, 40% (10 plants) produced a single band of A2 protein (FIG. 29—Table 2 and FIG. 8A), although the overall expression level was not high. These data clearly demonstrate that tobacco osmotin UTR sequences can greatly enhance Toxin A gene expression in transgenic *Arabidopsis* plants.

The increase in the overall accumulation of Toxin A protein also increased the chances of recovering insect-resistant lines. Bioassays were performed directly on 259 primary pDAB7026 transformants. Among these $T_0$ plants, 9 lines (not including line 7026-011, see below) showed 100% insect mortality (FIG. 30—Table 3). Except for line 7026-127, all these lines had Toxin A levels higher than 1,000 ppm. The bioactivity and high level accumulation of the Toxin A protein were coordinately transmitted into the next generation. At least 32 progeny were examined for each of these 9 lines as well as line 7026-011 (FIG. 30—Table 3). Although bioassays were not done on the $T_0$ plant of line 7026-011, its $T_1$ progeny were included in this study because the T0 plant had a high level of Toxin A protein. For line 7026-011, all except one of the 71 $T_1$ progeny showed 100% insect mortality. The remaining plant showed 87.5% mortality (1 of 8 insects survived), which was nevertheless significantly higher than the control mortality (19%) (Table 6). In contrast, for line 7026-195, none of its 32 $T_1$ progeny showed Toxin A accumulation or insecticidal activity. For the other lines, the percentage of progeny that showed high levels of Toxin A protein and insecticidal activity ranged from 90% to 18% (FIG. 30—Table 3). In total, 333 $T_1$ progeny for these 10 lines were analyzed, and 214 were found to retain a high level of Toxin A protein. Among these $T_1$ high expressers, 211 (98%) had significantly high insecticidal activity when compared to the control group (FIG. 30—Table 3). FIG. 31—Table 4 shows the average insect mortality of the high expressers and the low or non-expressers among the $T_1$ progeny for each line. These results further confirmed that the high level of accumulation of Toxin A protein was responsible for the plants' insecticidal activity against THW.

During the screening for insect-resistant lines amongst $T_0$ pDAB7026 plants, four lines were found that had very low or no Toxin A accumulation, yet showed a significantly high insecticidal activity. Sixteen $T_1$ progeny from each of these four lines were examined. None of these plants showed any Toxin A protein or insect activity (data not shown), suggesting that these four lines were false positives in the insect bioassays. The earlier bioassay results on the $T_0$ plants were probably due to variations in test insect viability or to some undetermined artifacts resulting from the transformation processes.

In contrast, we also identified four lines that showed high level accumulation of Toxin A protein, but no significant insect mortality. To determine if these could be false negative results, 32 progeny from each of these lines were analyzed. Except for line 7026-101, in which none of the progeny showed any Toxin A protein or insect activity, the other three lines, with a total 11 progeny, showed high level expression of the Toxin A gene (FIG. 32—Table 5). The average insect mortality shown by these $T_1$ high expressers was 98.2% while the control group was 14.0%. These results confirmed that the non-significant activity observed on these lines at the $T_0$ generation could have been escapes of the current bioassay procedure. These aberrant results underscore the need to examine transgenic progeny, rather than solely T0 plants, in assessing gene function.

In summary, from 274 pDAB7026 transgenic lines analyzed at the $T_1$ generation, 12 lines (4.4%) were identified with heritable high levels of Toxin A production and insect activity (FIG. 29—Table 2), even though the degree of heritability varied from 3% (line 7026-101) to 100% (line 7026-011). These results demonstrate that the enhanced accumulation of the Toxin A protein by the osmotin UTR sequences increased the recovery frequency of insect-resistant lines from 0.3% to 4.4% (FIG. 29—Table 2).

Figure 9:
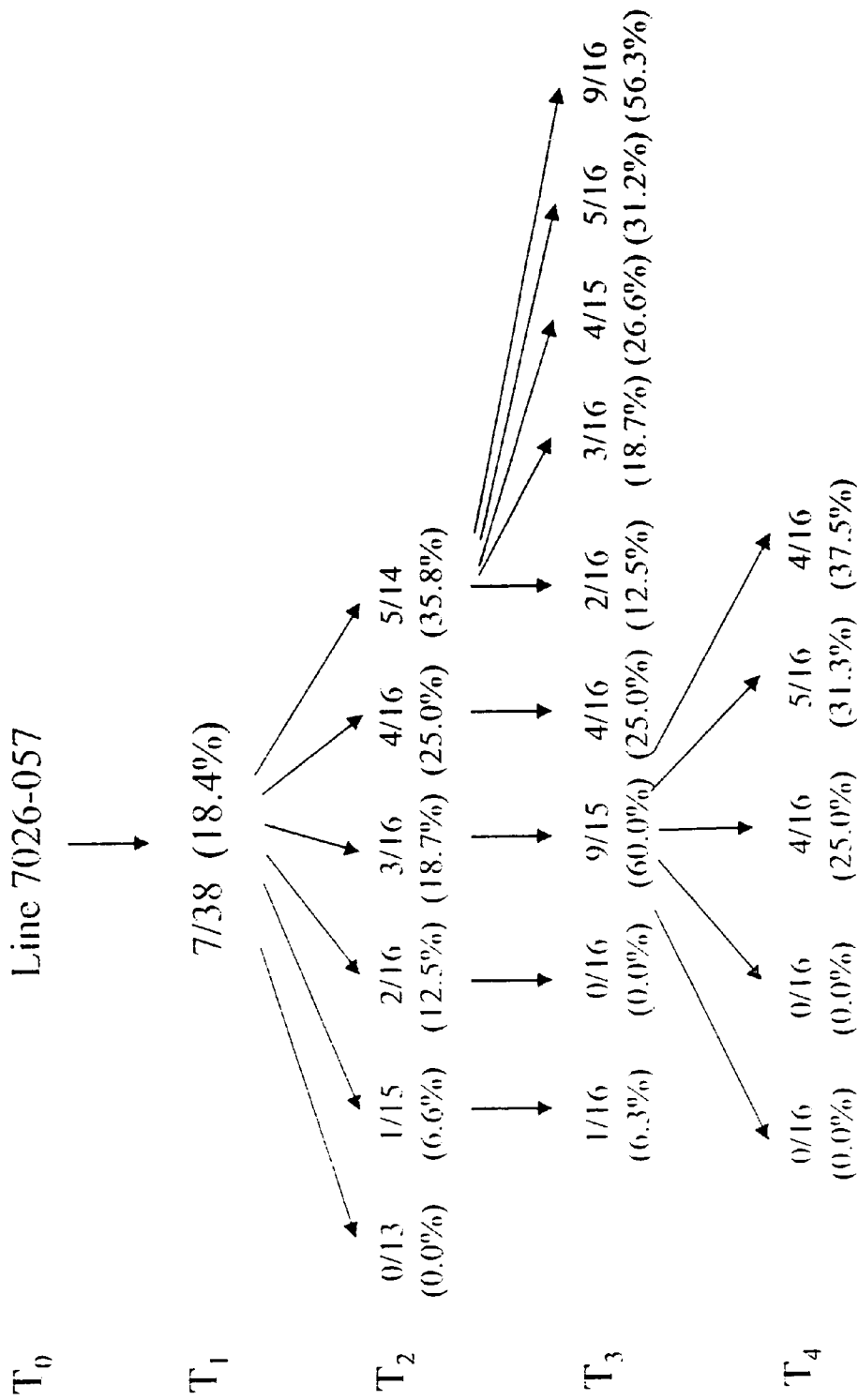
FIG. 9 provides multi-generation analyses of insect resistance in transgenic line 7026-057. The number of active plants in each given progeny family are indicated as n/N (active plants/total examined plants) and as percentage of total examined plants (shown in parenthesis). All the active plants shown here were high expressers and had 100% insect mortality. The number of generation for each progeny family is indicated on left.
Figure 10:
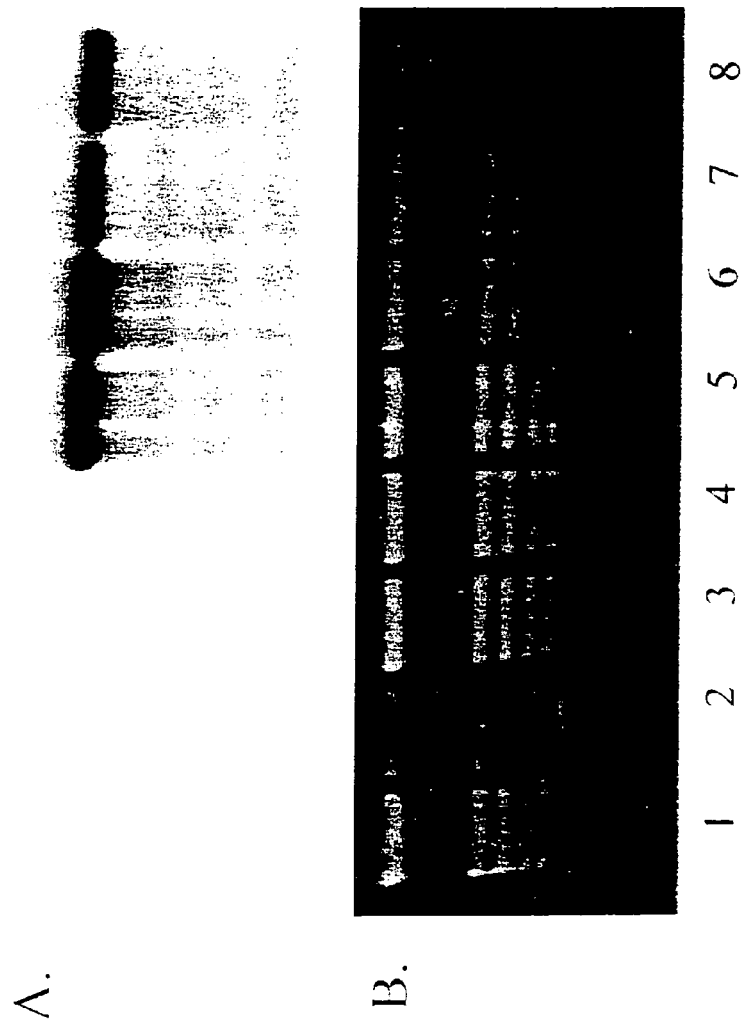
FIG. 10 is a comparative analysis of Toxin A RNA expression between high and low expressers of T1 progeny of line 7026-190. (A) Northern analysis of Toxin A RNA expression. Lanes 1-4: four $T_1$ plants with low Toxin A expression level (<50 ppm). Lanes 5-8: four $T_1$ plants with high Toxin A expression level (>1,400 ppm). (B) Ethidium bromide staining of RNA gel.
Figure 11:
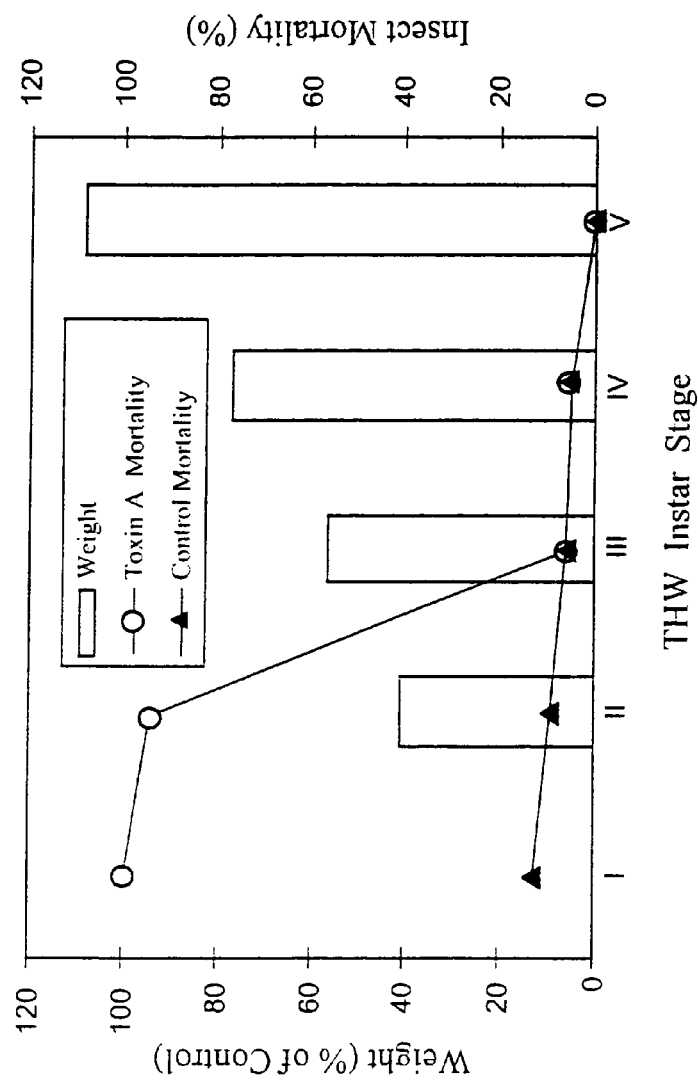
FIG. 11 illustrates the activity of Toxin A-expressing transgenic plants against THW with different ages. S The term "chimeric gene construct", as used herein, means a recombinant nucleic acid comprising genes or portions thereof from more than one organism.
Figure 12:
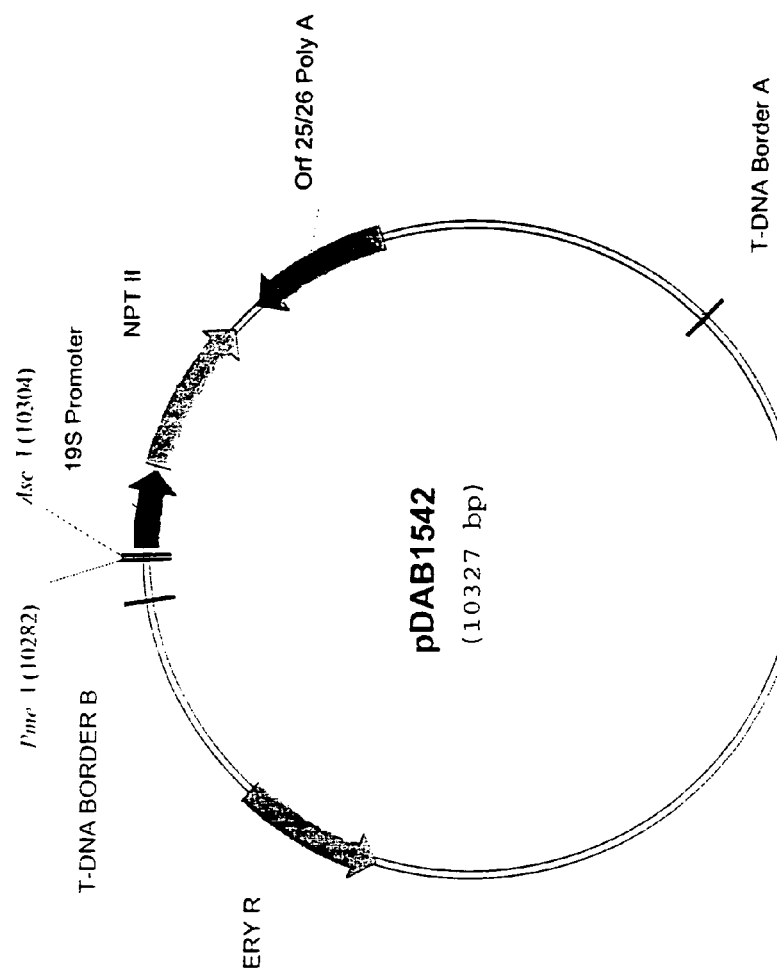
Figure 13:
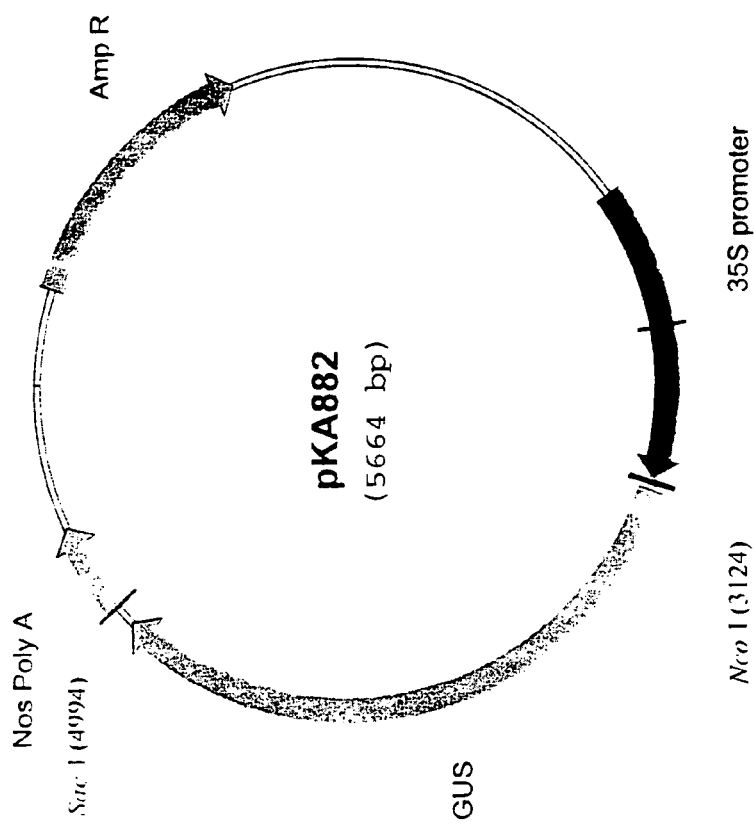
Figure 14:
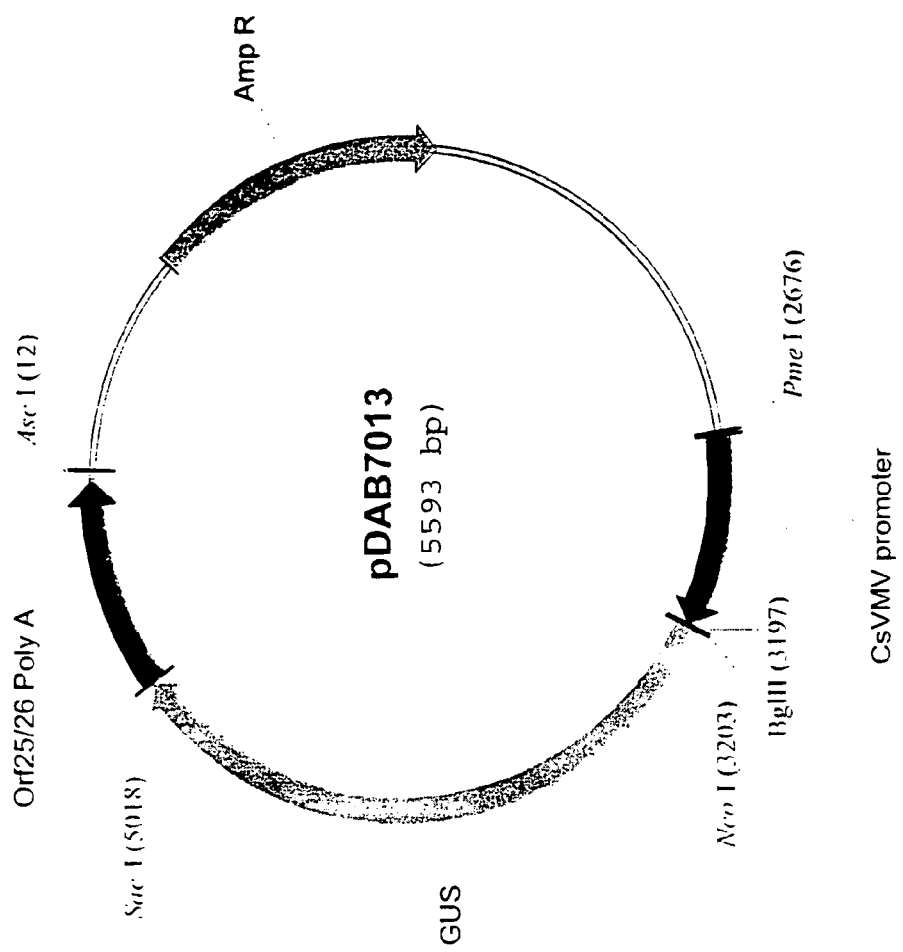
Figure 15:
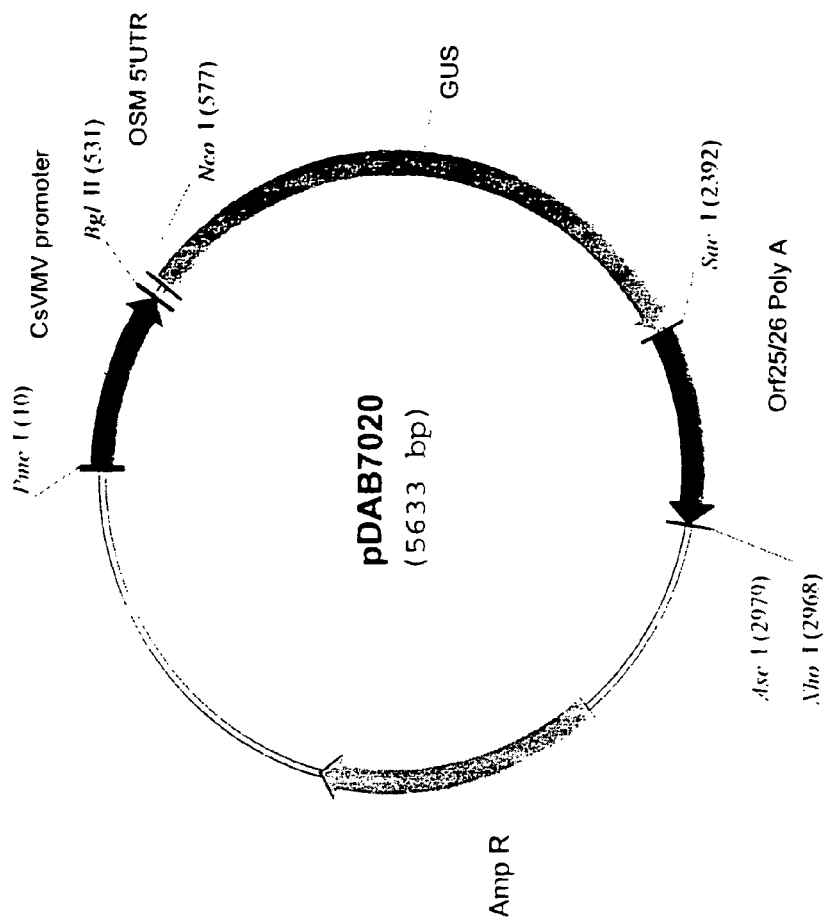
Figure 16:
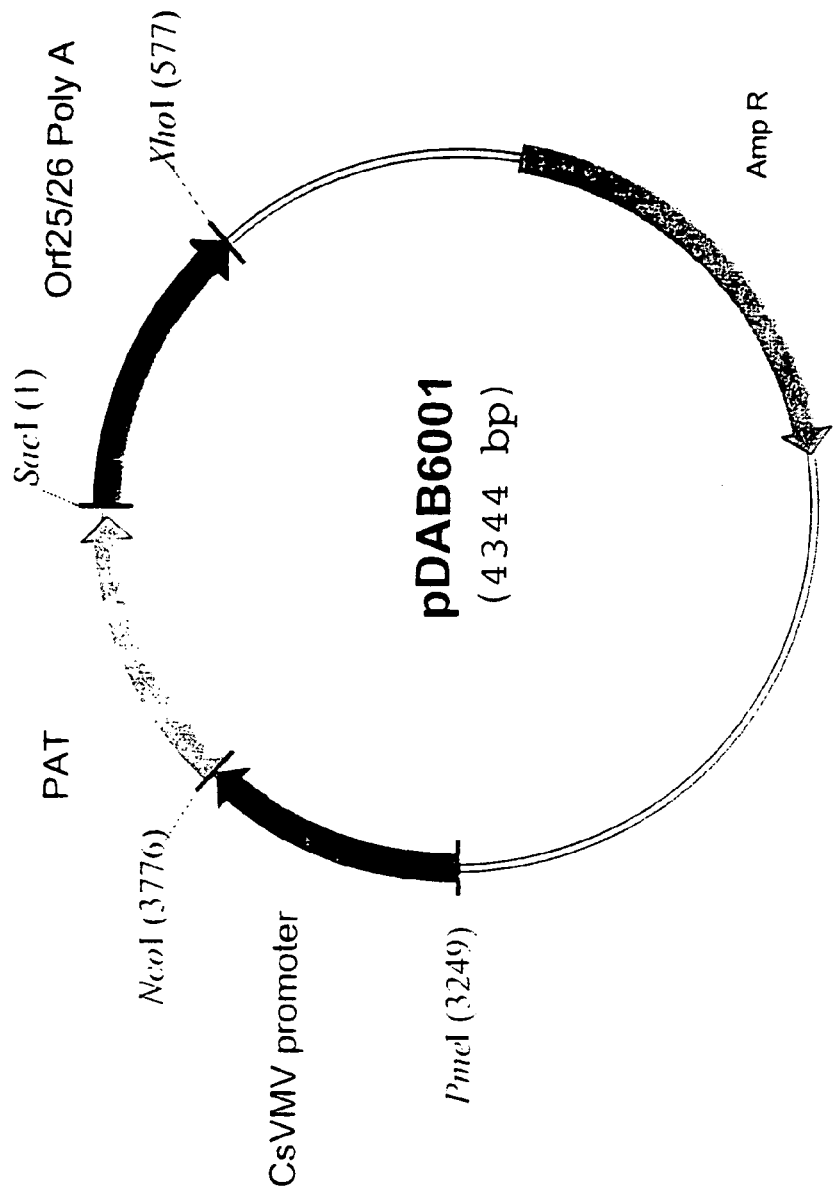
Figure 17:
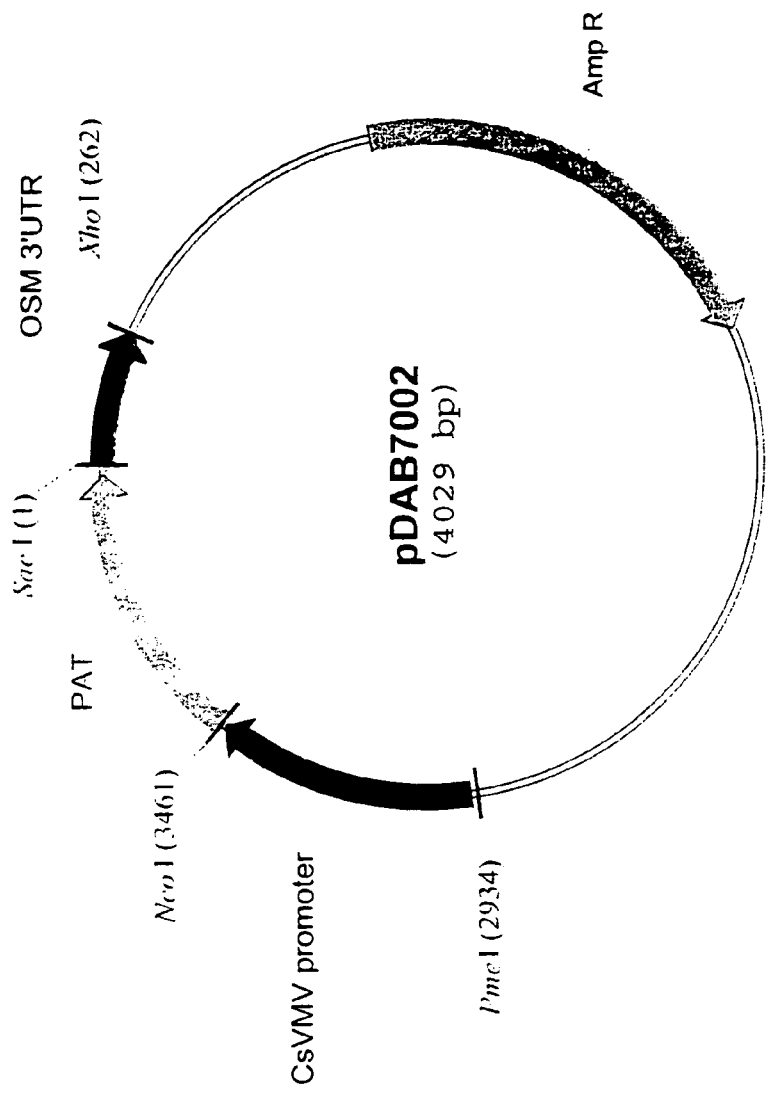
Figure 18:
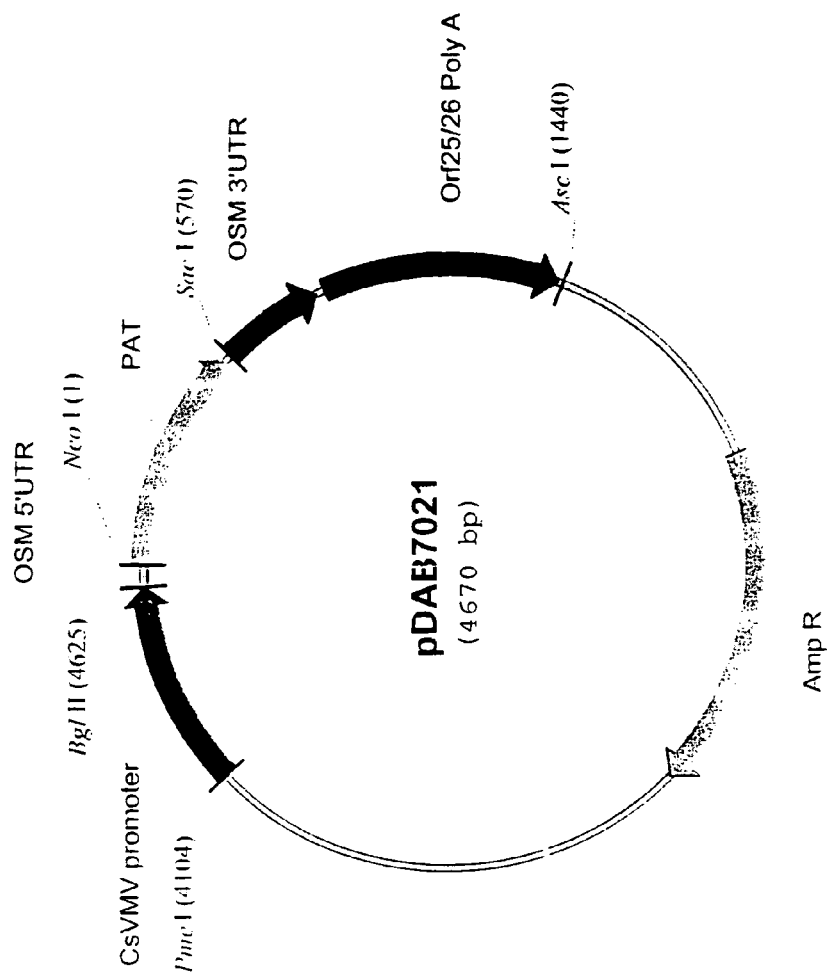
Figure 19:
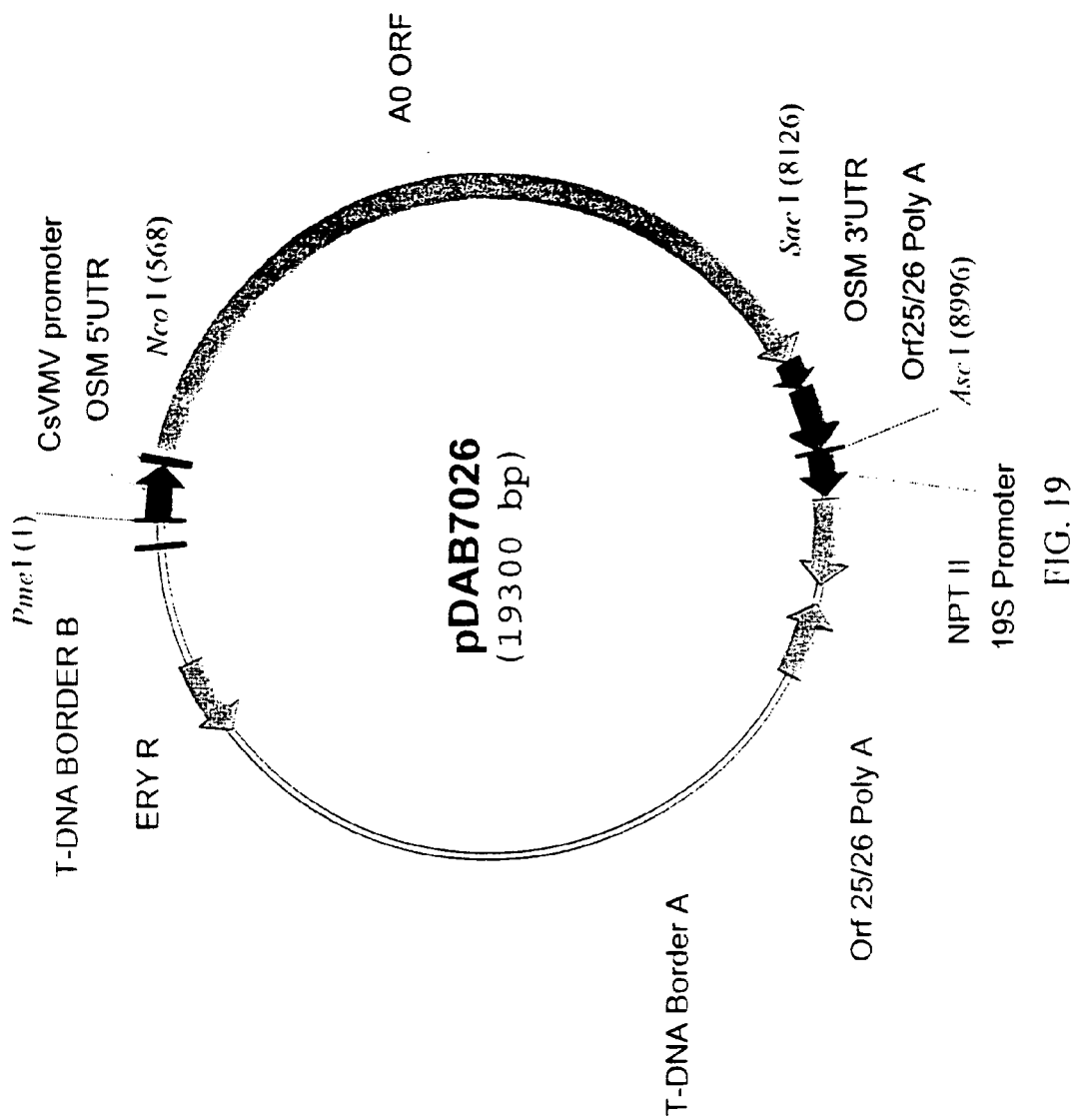

Lines 7026-011 and 7026-057 were further followed to their fifth generations ($T_4$ plants) to determine the stability of Toxin A gene expression and associated insecticidal activity. For line 7026-011, the overexpression of Toxin A and insecticidal activity were stably maintained in all progeny for five generations (FIG. 33—Table 6). However, the heritability pattern for line 7026-057 was more complicated (FIG. 9). Thirty-eight $T_1$ progeny were examined, and all 15 $T_1$ plants homozygous for the transgenes had lost Toxin protein production as well as insect activity. Only 7 of the remaining 23 hemizygous progeny retained both high level accumulation of Toxin A and 100% insect mortality (FIG. 29—Table 2). A $T_2$ generation was derived from 6 of the 7 insect active hemizygous $T_1$ plants (FIG. 9). The percentage of active plants for each $T_2$ family ranged from 0% to 35%.

Examination of $T_4$ progeny identified one $T_3$ family in which 60% of family members were high expressers and were insect active. One interesting question was to determine, for this family, if the average percentage of active plants in the $T_4$ generation would increase over the $T_3$ generation. Apparently, this was not the case. Similar results were also seen for the progeny of five $T_3$ families, which were derived from a single $T_2$ family, in which 35.8% family members were active plants.

According to the structural model of the Toxin A complex (FIG. 1), a question addressable by these transgenic materials was whether the A2 polypeptide is an indispensable part of the complex's activity. Transgenic plants carrying constructs pDAB7033, 7034, and 7035, which produce only A1 proteins at relatively high levels, were further studied. From the screening of 146 $T_1$ progeny, 12 high expressers were identified which covered all three A1 constructs. Bioassay results showed that none of these plants showed significantly higher insect mortality compared to the control plants (data not shown). This indicated that the A1 protein alone in *Arabidopsis* is not sufficient for insecticidal activity against THW.

Discussion

In this work, we first analyzed the expression of a plant-optimized *P. luminescens* strain W-14 tcdA gene in transgenic *Arabidopsis* plants. The results provided some important insights about the behaviors of Toxin A protein in plants: 1) the full length tcdA gene can produce Toxin A protein whose final products mimic those observed from the native *P. luminescens* strain W-14 and from a recombinant *E. coli* strain, indicating that Toxin A protein is appropriately processed in plant cells; 2) the N-terminal 88 amino acids of the A0 protein seem to serve as a signal peptide for protein cleavage, since the deletion of these amino acids prevents the cleavage of the TcdA protein into the A1 and A2 polypeptides; 3) The N-terminus and C-terminus of the A1 protein were not further processed in plants cells, otherwise, the A1 proteins encoded by three different A1 gene constructs would have the same molecular weights.

Figure 20:
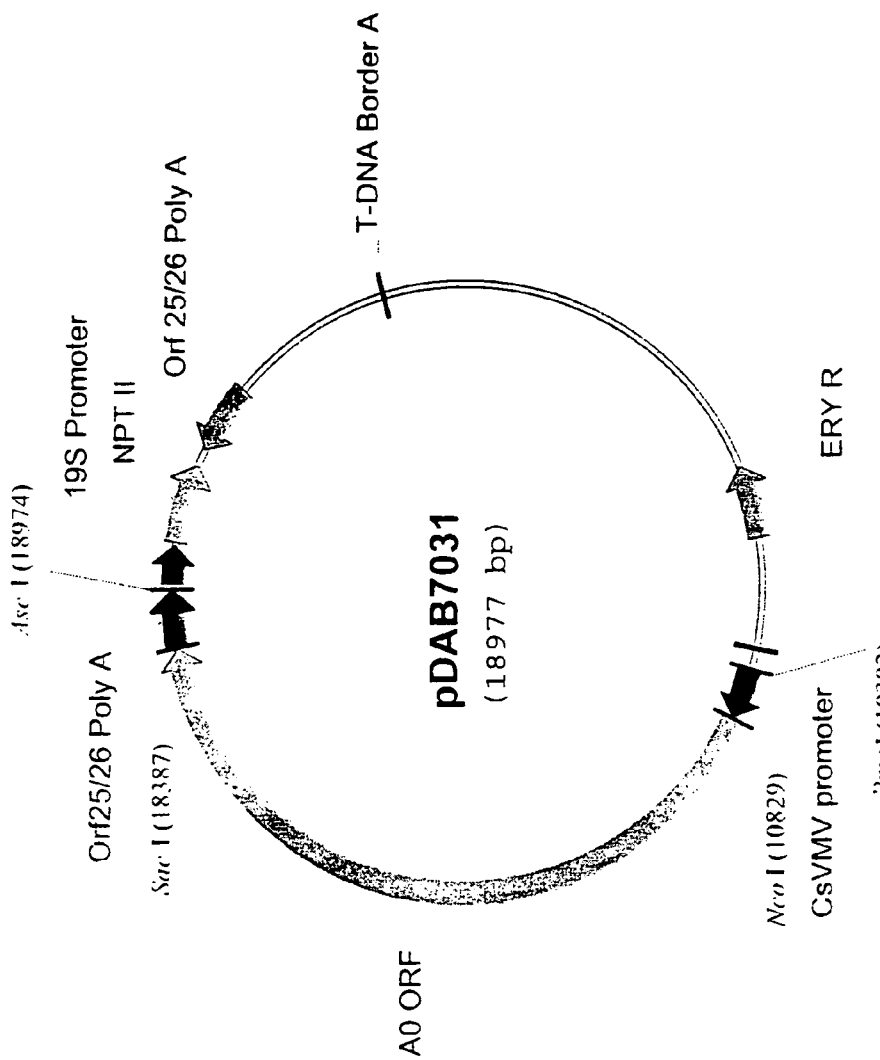

In the early stages of this work with construct pDAB7031 (FIG. 20), it was observed that the overall accumulation of Toxin A protein in transgenic plants was very low. The overall low expression also resulted in a low frequency of recovering insect-resistant lines (0.3% of transgenics). In the particular case of construct pDAB7032, A2 protein was not observed in the transgenic plants, even though the A2 mRNA was easily detected. Poor transgene expression in plants can be attributed to many factors, especially when using a gene from heterologous sources. Use of a strong promoter does not necessarily guarantee a high level of gene expression. In addition to low transcriptional activity due to integration position effects, features such as improper splicing, incomplete polyadenylation, inefficient nuclear export, mRNA instability, and poor translation efficiency all can result in low level accumulation of both mRNA and protein. Elimination of these potential pitfalls was attempted through complete redesign and synthesis of the plant-optimized Toxin A coding region. Further, Toxin A gene expression was enhanced by adding 5' and 3' UTR flanking sequences from a tobacco osmotin gene to the Toxin A gene. Structural features of the osmotin mRNA 5' and 3' UTRs are consistent with the criteria of a stable, highly expressed plant mRNA: i) the 5' UTR sequence is highly AT-rich, allowing ribosomes to easily scan to the start codon to initiate translation, and ii) the 3' UTR sequences can form a strong stem-loop secondary structure that may effectively block degradation from RNase. (Kozie, 1996). Indeed, after the osmotin 5' and 3' UTR sequences were added to the corresponding ends of the Toxin A gene(s), the overall production of the A1 and A0 proteins increased 5-10 fold. As a consequence, the recovery frequency for insect-resistant lines transformed with tcdA genes increased from 0.3% to 4.4%. Also, for the first time, accumulation of the A2 protein could be detected in 40% of plants examined that were transformed with the A2 gene alone.

Importantly, it was demonstrated that overexpression of tcdA in transgenic *Arabidopsis* plants can render the plants completely toxic to feeding THW. For the first time, it has been clearly shown that the presence of the A2 subunit is associated with Toxin A's insecticidal activity, as plants containing only the large A1 subunit were inactive. In our analysis of about 2,500 individual plants, insecticidal activity was always associated with high level accumulation of the Toxin A protein. These results indicate that the Toxin A gene is an excellent candidate for crop protection in agriculture, since Toxin A also has strong activity against SCR. The Toxin A gene and other *P. luminescens* toxin genes may open new routes for pest control in agriculture. Until now, transgenic crop insect control has heavily relied on the use of Bt toxin genes, and the *P. luminescens* toxin genes can help reduce the problem of development of resistance of pests to Bt plants. Stacking the Toxin A gene into plants which already contain a Bt gene may also increase the efficacy of insect toxicity in terms of potency and pest spectrum.

SUMMARY

The analysis of protein expression of three Toxin A coding regions in transgenic *Arabidopsis* plants is provided in Table 1. In plants carrying the A0 gene construct with no osmotin UTR flanks, only 23% of the 340 examined plants showed detectable protein expression. The average Toxin A protein level of expression plants was 67 PPM (parts per million, ng per mg soluble protein). However, for the 273 transgenic plants examined that carried the osmotin UTR-A0 gene construct, 39% showed protein expression, and the average Toxin A protein level of the expressing plants was 390 PPM. Therefore, osmotin UTR-A0 constructs are expressed about 6-fold higher as compared to non-osmotin A0 constructs. When all plants examined are included in the statistical analysis, the average Toxin A expression level for the A0 construct was 15 ppm, while the average Toxin A expression level for the osmotin UTR-A0 plants was 150 PPM. Thus, the difference in average Toxin A production between these two constructs is about 10 fold. The number of high expressers for each construct (Toxin A protein >700 PPM) was also calculated. Among the A0 plants, there were 2 high expressers (0.6%), whereas in the osmotin UTR-A0 plant group, 13 high expressers (4.7%) were found.

For transgenic plants carrying the A1/ΔC gene construct, 58% expressed the truncated A1 proteins, and the average A1 protein expression level of expressing plants was 251 ppm. For transgenic plants carrying the osmotin UTR-A1/ΔC construct, 90% of examined plants showed A1 protein expression, and the average level of expression was 1131 PPM (a 4.5-fold increase). For transgenic plants carrying the A2 gene, A2 protein expression could not be detected in any of the 32 examined plants. However, in 25 osmotin-A2 plants, 10 plants (40%) were found that expressed the A2 protein, and the average level for expression was 31 pp. These data clearly show that tobacco osmotin UTR sequences can greatly enhance foreign gene expression in transgenic *Arabidopsis* plants with three different gene constructs.

The insecticidal activity of the transgenic plants carrying full-length Toxin A gene constructs was also evaluated. For non-osmotin/A0 plants, only one line (0.3%) showed complete resistance (100% mortality) against tobacco hornworm (THW) at the T0 generation, and its activity was confirmed at the next generation. For the plant group with the osmotin UTR-A0 gene, 10 lines (3.6%) were found with heritable resistance to THW.

Having thus described in detail preferred embodiments of the present invention, it is to be understood that the various described embodiments are merely exemplary of the present invention and that many apparent variations thereof are possible without departing from the spirit or scope thereof. Accordingly, one skilled in the art will readily recognize that the present invention is not limited to the specific embodiments described herein.

What is claimed is:

1. A method for recombinantly producing a peptide or protein comprising:
   functionally linking a heterologous promoter and a nucleic acid sequence consisting of an isolated osmotin UTR element selected from the group consisting of SEQ. ID No. 1 and SEQ. ID No. 2 with a structural gene of interest.

2. A method of increasing expression of a gene in a plant cell comprising:
   functionally linking at least heterologous promoter and one nucleic acid sequence consisting of an isolated osmotin UTR element selected from the group consisting of SEQ. ID No. 1 and SEQ. ID No. 2 with a structural gene of interest to create a nucleic acid construct; transforming the plant cell with the nucleic acid construct; and growing the transformed cell under conditions in which the structural gene of interest is expressed.

3. The method of claim 1, wherein the at least one structural gene of interest comprises a gene capable of conferring a non-native phenotype in a plant.

4. The method of claim 1, wherein the at least one structural gene of interest comprises a gene capable of conferring insecticide or herbicide resistance in a plant.

5. The method of claim 1, wherein the at least one structural gene of interest comprises SEQ. ID. No. 5.

6. The method of claim 2, wherein the at least one structural gene of interest comprises a gene capable of conferring a non-native phenotype in a plant.

7. The method of claim 2, wherein the at least one structural gene of interest comprises a gene capable of conferring insecticide or herbicide resistance in a plant.

8. The method of claim 2, wherein the at least one structural gene of interest comprises SEQ. ID. No. 5.

* * * * *